(12) United States Patent
Blumenkopf et al.

(10) Patent No.: US 7,192,963 B2
(45) Date of Patent: *Mar. 20, 2007

(54) PYRROLO[2,3-D]PYRIMIDINE COMPOUNDS

(75) Inventors: Todd A. Blumenkopf, Old Lyme, CT (US); Mark E. Flanagan, Gales Ferry, CT (US); Michael J. Munchhof, Salem, CT (US)

(73) Assignee: Pfizer Inc, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 11/112,307

(22) Filed: Apr. 21, 2005

(65) Prior Publication Data

US 2005/0197349 A1    Sep. 8, 2005

Related U.S. Application Data

(63) Continuation of application No. 10/463,724, filed on Jun. 16, 2003, now Pat. No. 6,962,993.

(51) Int. Cl.
| C07D 487/04 | (2006.01) |
| A61K 31/519 | (2006.01) |
| A61K 17/06 | (2006.01) |
| A61K 37/06 | (2006.01) |
| A61P 19/02 | (2006.01) |

(52) U.S. Cl. .................. 514/265.1; 544/280; 546/216; 546/223; 546/249; 546/350

(58) Field of Classification Search ............. 514/265.1
See application file for complete search history.

(56) References Cited

U.S. PATENT DOCUMENTS

| 3,670,079 | A | * | 6/1972 | Patanelli et al. ............. 514/172 |
| 4,456,464 | A | * | 6/1984 | Lee et al. .................... 504/195 |
| 4,526,608 | A | * | 7/1985 | Lee ............................. 504/259 |
| 4,590,282 | A | * | 5/1986 | Henrick ....................... 549/453 |
| 4,879,309 | A | * | 11/1989 | Doll et al. ................... 514/513 |
| 4,933,339 | A | * | 6/1990 | Sharma .................... 514/235.5 |
| 4,997,936 | A | * | 3/1991 | Christensen et al. ........ 540/350 |
| 5,134,123 | A | * | 7/1992 | Branca et al. ................ 514/18 |
| 5,356,903 | A | * | 10/1994 | Eissenstat et al. .......... 514/311 |
| 5,389,509 | A |   | 2/1995 | Maskasky |
| 5,686,457 | A |   | 11/1997 | Traxler et al. |
| 6,080,747 | A |   | 6/2000 | Uckun et al. |
| 6,136,595 | A |   | 10/2000 | Ihle et al. |
| 6,180,636 | B1 |   | 1/2001 | Traxler et al. |
| 6,187,552 | B1 |   | 2/2001 | Roberds et al. |
| 6,506,762 | B1 | * | 1/2003 | Horvath et al. .......... 514/259.4 |
| 6,552,192 | B1 | * | 4/2003 | Hanus et al. ................ 544/280 |
| 6,610,847 | B2 | * | 8/2003 | Blumenkopf et al. ....... 544/280 |
| 6,627,754 | B2 | * | 9/2003 | Blumenkopf et al. ....... 544/280 |
| 2003/0073719 | A1 | * | 4/2003 | Wilcox et al. .............. 514/317 |
| 2004/0242600 | A1 | * | 12/2004 | Bold et al. ................ 514/265.1 |
| 2006/0211678 | A1 | * | 9/2006 | Ahmed et al. ........... 514/210.21 |

FOREIGN PATENT DOCUMENTS

| EP | 0795556 | 9/1997 |
| EP | 0682027 | 10/1997 |
| WO | WO 9519774 | 7/1995 |
| WO | WO 9713771 | 10/1995 |
| WO | WO 9802437 | 7/1996 |
| WO | WO 9802438 | 7/1996 |
| WO | WO 9640142 | 12/1996 |
| WO | WO 9702262 | 1/1997 |
| WO | WO 9702266 | 1/1997 |
| WO | WO 9718212 | 5/1997 |
| WO | WO 9727199 | 7/1997 |
| WO | WO 9728161 | 8/1997 |
| WO | WO 9732879 | 9/1997 |
| WO | WO 9749706 | 12/1997 |
| WO | WO 9807726 | 2/1998 |
| WO | WO 9823613 | 6/1998 |
| WO | WO 9833798 | 8/1998 |
| WO | WO 9951599 | 10/1999 |
| WO | WO 9961428 | 12/1999 |
| WO | WO 9965908 | 12/1999 |
| WO | WO 9965909 | 12/1999 |

(Continued)

OTHER PUBLICATIONS

The MDAdvice.com entry for Asthma http://www.mdadvice.com/topics/asthma/info/1.htm downloaded from the Internet Mar. 5, 2003.*

(Continued)

Primary Examiner—Mark L. Berch
(74) Attorney, Agent, or Firm—Gregg C. Benson; Christopher J. Verni

(57) ABSTRACT

A compound of the formula

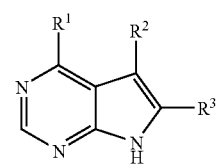

wherein $R^1$, $R^2$ and $R^3$ are as defined above, useful as inhibitors of protein kinases, such as the enzyme Janus Kinase 3.

48 Claims, No Drawings

FOREIGN PATENT DOCUMENTS

| | | |
|---|---|---|
| WO | WO 0000202 | 1/2000 |
| WO | WO 0010981 | 3/2000 |
| WO | WO 0017203 | 3/2000 |
| WO | WO 0142246 | 6/2001 |

OTHER PUBLICATIONS

The Medline Medical Encyclopedia entry for Psoriasis http://www.nlm.nih.gov/medlineplus/ency/article/000434.htm downloaded from the Internet Mar. 5, 2003.*

Illustrated Health Encyclopedia entry for Crohn's disease Prevention http://www.austin360.com/shared/health/adam/ency/article/000249prv.html downloaded from the Internet Mar. 5, 2003.*

Columbia University College of P & S Complete Home Medical Guide entry for Arthritis PREVENTION http://cpmcnet.columbia.edu/texts/guide/hmg25_0006.html downloaded from the Internet Mar. 5, 2003.*

Bolen, Ann. Rev. Immunology 15: 371 (1997).*

J. J. O'Shea, et al., *Phosphorylation and activation of the Jak-3 Janus Kinase in response to Interleukin-2*, Nature, 370, 151 (1994).

S. M. Russell, et al., *Interaction of IL-2Rβ and γc Chains with Jak1 and Jak3: Implications for XSCID and XCID*, Science, 266, 1042 (1994).

J. N. Ihle, *The Janus Protein Tyrosine Kinase Family and Its Role in Cytokine Signaling*, Adv. Immunology, 60, 1, (1995).

J. N. Ihle, *The Janus Protein Tyrosine Kinases in hematopoietic cytokine signaling*, Semin. Immunology, 7, 247, (1995).

T. Musso, et al., *Regulation of JAK3 Expression in Human Monocytes: Phosphorylation in Response to Interleukings 2, 4, and 7*, J. Exp. Med., 181, 1425 (1995).

R. A. Kirken, et al., *Activation of JAK3, but not JAK1, is critical for IL-2-induced proliferation and STAT5 Recruitment by a COOH-terminal region of the IL-2 receptor β-chain*, Cytokine, 7 689, (1995).

M. G. Malabarba, et al., *Activation of JAK3, but not JAK1, is Critical to Interleukin-4 (IL4) Stimulated Proliferation and Requires a Membrane-proximal Region of IL4 Receptor α\**, J. Biol. Chem., 270, 9630, (1995).

J. H. Hanke, B. A. Pollok, and P. S. Changelian, *Role of tyrosine kinases in lymphocyte activation: Targets for drug intervention*, Inflamm. Res., 44, 357, (1995).

E.E. Eynon, et al., *Disruption of Cytokine Signaling in Lymphoid Development: Unique Contributions of the Common Cytokine Gamma Chain and the JAK3 Kinase*, J. Interferon Cytokine Res., 16, 677, (1996).

S. A. Oakes, et al., *Signaling via IL-2 and IL-4 in JAK#-Deficient Severe Combined Immunodeficiency Lymphocytes: JAK3-Dependent and Independent Pathways*, Immunity, 5, 605 (1996).

L. D. Norangelo, et al, *Severe Combined Immune Deficiency due to Defects of the JAK3 Tyrosine Kinase*, Prog. Immunodeficiency, 6, 61, (1996).

D. C. Thomis, et al., *Peripheral Expression of JAK3 is Required to Maintain T Lymphocyte Function*, J. Exp. Med., 185, 197, (1997).

B. H. Nelson, et al., *Requirement for an initial signal from the membrane-proximal region of the interleukin 2 receptor γc chain for Janus kinase activation leading to T cell proliferation*, Proc. Natl. Acad. Sci. USA, 94, 1878, (1997).

A. M. Baird, et al., *T Cell development and activation in Jak3-deficient mice*, J. Leukocyte Biol., 63, 669, (1998).

K. D. Liu, et al., *JAK/STAT signaling by cytokine receptors*, Curr. Opin. Immunol.

W. J. Leonard and J. J. O'Shea, *JAKS and STATS: Biological Implications*, Annu. Rev. Immunol., 16, 293, (1998).

F. Candotti, et al., *Severe combined immune deficiencies due to defects in the common γ chain-JAK3 signaling pathway*, Springer Semin. Immuopathol., 19, 401, (1998).

R. Malaviya, et al., *Targeting Janus Kinase 3 in Mast Cells Prevents Immediate Hypersensitivity Reactions and Anaphylaxis*, J. Biol. Chem., 274, 27028 (1999).

D. C. Thomis, et al., *The Jak Family Tyrosine Kinase Jak3 is Required for IL-2 Synthesis by Naive/Resting CD4+ T Cells*, J. Immunol., 163, 5411 (1999).

E. Chen, et al., *Advances in Cytokine Signaling: The Role of Jaks and STATs*, Transplantation Proc., 31, 1482, (1999).

R. Moriggi, et al., *Stat5 Activation is Uniquely Associated with Cytokine Signaling in Peripheral T Cells*, Immunity, 11, 225 (1995).

L. H. Wang, et al., *JAK3, STAT, and MAPK Signaling Pathways as Novel Molecular Targets for the Tyrphostin AG-490 Regulation of IL-2-Mediated T Cell Response*, J. Immunol., 162, 3897, (1999).

E. A. Sudbeck, et al., *Structure-based Design of Specific Inhibitors of Janus Kinase 3 as Apoptosis-inducing Antileukemic Agents*, Clin. Cancer Res., 5, 1569, (1999).

F. M. Uckun, et al., *In Vivo Toxicity and Pharmacokinetic Features of the Janus Kinase 3 Inhibitor WHI-P131 [ 40(4'-Hydroxyphenyl)-Amino-6,7-Dimethosyquinazoline]*, Clin. Cancer Research, 5, 2954, (1999).

E. A. Sudbeck and F. M. Uckun, *Recent Advances in JAK3 kinase inhibitors*, IDrugs, 2, 1026, (1999).

R. Malaviya, et al., *Genetic and Biochemical Evidence for a Critical Role of Janus Kinase (JAK)-3 in Mast Cell-Mediated Type I Hypersensitivity Reactions*, Biochem. Biophys., Res. Commun., 257, 807, (1999).

V. N. Trieu, et al., *A Specific Inhibitor of Janus Kinase-3 Increases Survival in a Transgenic Mouse Model of Amyotrophic Lateral Sclerosis*, Biochem. Biophys. Res. Commun., 267, 22, (2000).

X. C. Li, et al., *Blocking the Common γ-Chain of Cytokine Receptors Induces T Cell Apoptosis and Long-Term Islet Allograft Survival*, J. Immunol., 164, 1193 (2000)/.

R. Malaviya, et al., *Treatment of allergic asthma by targeting Janus kinase 3-dependent leukotriene synthesis in mast cells with 4-(3',4'-Dibromo-4'hydroxyphenyl)amino-6,7-dimethoxyquinazoline (WHI-P97)*, J. Pharmacol. Exp. Ther., 295, 912 (2000).

S. Ghosh, et al., *4- 93-Bromo-4-hydroxypheynl)amino 6,7-dimethoxyquinazolin-1-ium chloride methanol solvate and 4-(3-hydroxyphenyl)amino0-6,7-dimethoxy-1-quinazolinium chloride*. Acta Crystallogr., C: Cryst. Struct. Commun., C57, 76 (2001).

E. A. Skudbeck, et. al. *An inhibitor of janus kinase 3: 4-(4-hydroxyphenylamino)-6,7-dimethoxyquinazolin-1-ium chloride*, Acta Crystallogr., SectC: Cryst. Struct. Commun., C56, 1282 (2000).

Traxler, P. M., et al., *Protein tyrosine kinase inhibitors in cancer treatment*, Exp. Opin. Ther. Patents, (1997), 7 (6): 571-588.

Traxler, P. M., et al., *4-(phenylamino)pyrrolopyrimidine: Potent and Selective, ATP Site Directed Inhibitors of the EGF-Receptor Protein Tyrosine Kinase*, J. Med. Chem., (1996), 39, 2285-2292.

\* cited by examiner

PYRROLO[2,3-D]PYRIMIDINE COMPOUNDS

CROSS-REFERENCE TO RELATED APPLICATIONS

This is a continuation application based upon and claiming priority under 35 § U.S.C. 120 to U.S. patent application Ser. No. 10/463,724 filed Jun. 16, 2003, now U.S. Pat. No. 6,962,993, which in turn claims priority under 35 U.S.C. § 120 to U.S. patent application Ser. No. 09/891,028 filed Jun. 25, 2001, now U.S. Pat. No. 6,696,567, which in turn claims the benefit of priority under 35 U.S.C. § 119(e) to U.S. provisional patent application No. 60/214,287, filed Jun. 26, 2000.

BACKGROUND OF THE INVENTION

The present invention relates to pyrrolo[2,3-d]pyrimidine compounds which are inhibitors of protein kinases, such as the enzyme Janus Kinase 3 (hereinafter also referred to as JAK3) and as such are useful therapy as immunosuppressive agents for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

This invention also relates to a method of using such compounds in the treatment of the above indications in mammals, especially humans, and the pharmaceutical compositions useful therefor.

JAK3 is a member of the Janus family of protein kinases. Although the other members of this family are expressed by essentially all tissues, JAK3 expression is limited to hematopoetic cells. This is consistent with its essential role in signaling through the receptors for IL-2, IL-4, IL-7, IL-9 and IL-15 by non-covalent association of JAK3 with the gamma chain common to these multichain receptors. XSCID patient populations have been identified with severely reduced levels of JAK3 protein or with genetic defects to the common gamma chain, suggesting that immunosuppression should result from blocking signaling through the JAK3 pathway. Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

SUMMARY OF THE INVENTION

The present invention relates to a compound of the formula

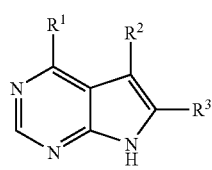

I or the pharmaceutically acceptable salt thereof; wherein $R^1$ is a group of the formula

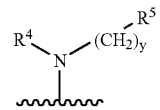

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_{1-C6})$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is $(C_2-C_9)$heterocycloalkyl wherein the heterocycloalkyl groups must be substituted by one to five groups consisting of carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, amino$(C_1-C_6)$alkyl, hydroxy $(C_1-C_6)$alkyl, $(C_1C_6)$alkoxy$(C_1-C_6)$alkyl, $(C_1-C_6)$acyloxy $(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$ alkyl, $(C_1C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino $(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $(C_1-C_6)$alkyl-$S(O)_m$, $R^{15}R^{16}NS(O)_m$, $R^{15}R^{16}NS(O)_m$ $(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl; and a group of the formula

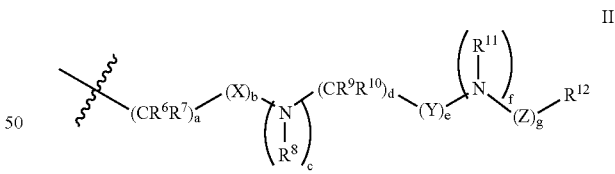

II wherein a is 0, 1, 2, 3 or 4;

b, c, e, f and g are each independently 0 or 1;

d is 0, 1, 2, or 3;

X is $S(O)_n$ wherein n is 0, 1 or 2; oxygen, carbonyl or —C(=N-cyano)-;

Y is $S(O)_n$ wherein n is 0, 1 or 2; or carbonyl; and

Z is carbonyl, C(O)O—, C(O)NR— wherein R is hydrogen or $(C_1-C_6)$alkyl; or Z is $S(O)_n$ wherein n is 0, 1 or 2;

$R^6$, $R^7$, $R^8$, $R^9$, $R^{10}$ and $R^{11}$ are each independently selected from the group consisting of hydrogen or $(C_1-C_6)$ alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano ($C_1$–$C_6$)alkyl, trifluoromethyl($C_1$–$C_6$)alkyl, nitro, nitro($C_1$–$C_6$)alkyl or ($C_1$–$C_6$)acylamino;

$R^{12}$ is ($C_6$–$C_{10}$)aryl, ($C_2$–$C_9$)heteroaryl, ($C_3$–$C_{10}$)cycloalkyl or ($C_2$–$C_9$)heterocycloalkyl, wherein the aryl, heteroaryl, cycloalkyl and heterocycloalkyl groups are optionally substituted by one to four groups consisting of hydrogen, deuterium, amino, halo, oxo, hydroxy, nitro, carboxy, ($C_2$–$C_6$)alkenyl, ($C_2$–$C_6$)alkynyl, trifluoromethyl, trifluoromethoxy, ($C_1$–$C_6$)alkyl, ($C_1$–$C_6$)alkoxy, ($C_3$–$C_{10}$)cycloalkyl, ($C_1$–$C_6$)alkyl-CO—NH—, ($C_1$–$C_6$)alkoxy-CO—NH—, ($C_1$–$C_6$)alkyl-CO—NH—($C_1$–$C_6$)alkyl, ($C_1$–$C_6$)alkoxy-CO—NH—($C_1$–$C_6$)alkyl, ($C_1$–$C_6$)alkoxy-CO—NH—($C_1$–$C_6$)alkoxy, carboxy, carboxy($C_1$–$C_6$)alkyl, carboxy($C_1$–$C_6$)alkoxy, benzyloxycarbonyl($C_1$–$C_6$)alkoxy, ($C_1$–$C_6$)alkoxycarbonyl($C_1$–$C_6$)alkoxy, ($C_6$–$C_{10}$)aryl, amino, amino($C_1$–$C_6$)alkyl, ($C_1$–$C_6$)alkoxycarbonylamino, ($C_6$–$C_{10}$)aryl($C_1$–$C_6$)alkoxycarbonylamino, ($C_1$–$C_6$)alkylamino, (($C_1$–$C_6$)alkyl)$_2$amino, ($C_1$–$C_6$)alkylamino($C_1$–$C_6$)alkyl, (($C_1$–$C_6$)alkyl)$_2$amino($C_1$–$C_6$)alkyl, hydroxy, ($C_1$–$C_6$)alkoxy, carboxy, carboxy($C_1$–$C_6$)alkyl, ($C_1$–$C_6$)alkoxycarbonyl, ($C_1$–$C_6$)alkoxycarbonyl($C_1$–$C_6$)alkyl, ($C_1$–$C_6$)alkoxy-CO—NH—, ($C_1$–$C_6$)alkyl-CO—NH—, cyano, ($C_5$–$C_9$)heterocycloalkyl, amino-CO—NH—, ($C_1$–$C_6$)alkylamino-CO—NH—, (($C_1$–$C_6$)alkyl)$_2$amino-CO—NH—, ($C_6$–$C_{10}$)arylamino-CO—NH—, ($C_5$–$C_9$)heteroarylamino-CO—NH—, ($C_1$–$C_6$)alkylamino-CO—NH—($C_1$–$C_6$)alkyl, (($C_1$–$C_6$)alkyl)$_2$amino-CO—NH—($C_1$–$C_6$)alkyl, ($C_6$–$C_{10}$)arylamino-CO—NH—($C_1$–$C_6$)alkyl, ($C_5$–$C_9$)heteroarylamino-CO—NH—($C_1$–$C_6$)alkyl, ($C_1$–$C_6$)alkylcyano, ($C_1$–$C_6$)alkylcarboxy($C_1$–$C_6$)alkoxy, ($C_1$–$C_6$)alkylcarboxy, sulfonylamino, aminosulfonyl, sulfonylamino($C_1$–$C_6$)alkyl, sulfonylaminocarboxy($C_1$–$C_6$)alkyl, ($C_1$–$C_6$)alkylsulfonyl, ($C_1$–$C_6$)alkylsulfonylamino, ($C_1$–$C_6$)alkylsulfonylamino($C_1$–$C_6$)alkyl, ($C_6$–$C_{10}$)arylsulfonyl, ($C_6$–$C_{10}$)arylsulfonylamino, ($C_6$–$C_{10}$)arylsulfonylamino($C_1$–$C_6$)alkyl, ($C_1$–$C_6$)alkylsulfonylamino, ($C_1$–$C_6$)alkylsulfonylamino($C_1$–$C_6$)alkyl, ($C_3$–$C_{10}$)cycloalkyl, ($C_3$–$C_{10}$)cycloalkoxy, ($C_1$–$C_6$)alkylamino, (($C_1$–$C_6$)alkyl)$_2$amino, ($C_6$–$C_{10}$)arylamino, ($C_1$–$C_6$)alkylthio, ($C_6$–$C_{10}$)arylthio, ($C_1$–$C_6$)alkylsulfinyl, ($C_6$–$C_{10}$)arylsulfinyl, ($C_1$–$C_6$)alkylsulfonyl, ($C_6$–$C_{10}$)arylsulfonyl, ($C_1$–$C_6$)acyl, ($C_1$–$C_6$)alkoxy-CO—NH—, ($C_1$–$C_6$)alkyamino-CO—, ($C_5$–$C_9$)heteroaryl, ($C_2$–$C_9$)heterocycloalkyl or ($C_6$–$C_{10}$)aryl wherein the heteroaryl, heterocycloalkyl and aryl groups which are optionally substituted on $R^{12}$ may be further substituted by one to three groups consisting of halo, ($C_1$–$C_6$)alkyl, ($C_1$–$C_6$)alkyl-CO—NH—, ($C_1$–$C_6$)alkoxy-CO—NH—, ($C_1$–$C_6$)alkyl-CO—NH—($C_1$–$C_6$)alkyl, ($C_1$–$C_6$)alkoxy-CO—NH—($C_1$–$C_6$)alkyl, ($C_1$–$C_6$)alkoxy-CO—NH—($C_1$–$C_6$)alkoxy, carboxy, carboxy($C_1$–$C_6$)alkyl, carboxy($C_1$–$C_6$)alkoxy, benzyloxycarbonyl($C_1$–$C_6$)alkoxy, ($C_1$–$C_6$)alkoxycarbonyl($C_1$–$C_6$)alkoxy, ($C_6$–$C_{10}$)aryl, amino, amino($C_1$–$C_6$)alkyl, ($C_1$–$C_6$)alkoxycarbonylamino, ($C_6$–$C_{10}$)aryl($C_1$–$C_6$)alkoxycarbonylamino, ($C_1$–$C_6$)alkylamino, (($C_1$–$C_6$)alkyl)$_2$amino, ($C_1$–$C_6$)alkylamino($C_1$–$C_6$)alkyl, (($C_1$–$C_6$)alkyl)$_2$amino($C_1$–$C_6$)alkyl, hydroxy, ($C_1$–$C_6$)alkoxy, carboxy, carboxy($C_1$–$C_6$)alkyl, ($C_1$–$C_6$)alkoxycarbonyl, ($C_1$–$C_6$)alkoxycarbonyl($C_1$–$C_6$)alkyl, ($C_1$–$C_6$)alkoxy-CO—NH—, ($C_1$–$C_6$)alkyl-CO—NH—, cyano, ($C_5$–$C_9$)heterocycloalkyl, amino-CO—NH—, ($C_1$–$C_6$)alkylamino-CO—NH—, (($C_1$–$C_6$)alkyl)$_2$amino-CO—NH—, ($C_6$–$C_{10}$)arylamino-CO—NH—, ($C_5$–$C_9$)heteroarylamino-CO—NH—, ($C_1$–$C_6$)alkylamino-CO—NH—($C_1$–$C_6$)alkyl, (($C_1$–$C_6$)alkyl)$_2$amino-CO—NH—($C_1$–$C_6$)alkyl, ($C_6$–$C_{10}$)arylamino-CO—NH—($C_1$–$C_6$)alkyl, ($C_5$–$C_9$)heteroarylamino-CO—NH—($C_1$–$C_6$)alkyl, ($C_1$–$C_6$)alkylsulfonyl, ($C_1$–$C_6$)alkylsulfonylamino, ($C_1$–$C_6$)alkylsulfonylamino($C_1$–$C_6$)alkyl, ($C_6$–$C_{10}$)arylsulfonyl, ($C_6$–$C_{10}$)arylsulfonylamino, ($C_6$–$C_{10}$)arylsulfonylamino($C_1$–$C_6$)alkyl, ($C_1$–$C_6$)alkylsulfonylamino, ($C_1$–$C_6$)alkylsulfonylamino($C_1$–$C_6$)alkyl, ($C_5$–$C_9$)heteroaryl and ($C_2$–$C_9$)heterocycloalkyl;

$R^2$ and $R^3$ are each independently selected from the group consisting of hydrogen, deuterium, amino, halo, hydroxy, nitro, carboxy, ($C_2$–$C_6$)alkenyl, ($C_2$–$C_6$)alkynyl, trifluoromethyl, trifluoromethoxy, ($C_1$–$C_6$)alkyl, ($C_1$–$C_6$)alkoxy, ($C_3$–$C_{10}$)cycloalkyl wherein the alkyl, alkoxy or cycloalkyl groups are optionally substitued by one to three groups selected from halo, hydroxy, carboxy, amino($C_1$–$C_6$)alkylthio, ($C_1$–$C_6$)alkylamino, (($C_1$–$C_6$)alkyl)$_2$amino, ($C_5$–$C_9$)heteroaryl, ($C_2$–$C_9$)heterocycloalkyl, ($C_3$–$C_9$)cycloalkyl or ($C_6$–$C_{10}$)aryl; or $R^2$ and $R^3$ are each independently ($C_3$–$C_{10}$)cycloalkyl, ($C_3$–$C_{10}$)cycloalkoxy, ($C_1$–$C_6$)alkylamino, (($C_1$–$C_6$)alkyl)$_2$amino, ($C_6$–$C_{10}$)arylamino, ($C_1$–$C_6$)alkylthio, ($C_6$–$C_{10}$)arylthio, ($C_1$–$C_6$)alkylsulfinyl, ($C_6$–$C_{10}$)arylsulfinyl, ($C_1$–$C_6$)alkylsulfonyl, ($C_6$–$C_{10}$)arylsulfonyl, ($C_1$–$C_6$)acyl, ($C_1$–$C_6$)alkoxy-CO—NH—, ($C_1$–$C_6$)alkyamino-CO—, ($C_5$–$C_9$)heteroaryl, ($C_2$–$C_9$)heterocycloalkyl or ($C_6$–$C_{10}$)aryl wherein the heteroaryl, heterocycloalkyl and aryl groups are optionally substituted by one to three halo, ($C_1$–$C_6$)alkyl, ($C_1$–$C_6$)alkyl-CO—NH—, ($C_1$–$C_6$)alkoxy-CO—NH—, ($C_1$–$C_6$)alkyl-CO—NH—($C_1$–$C_6$)alkyl, ($C_1$–$C_6$)alkoxy-CO—NH—($C_1$–$C_6$)alkyl, ($C_1$–$C_6$)alkoxy-CO—NH—($C_1$–$C_6$)alkoxy, carboxy, carboxy($C_1$–$C_6$)alkyl, carboxy($C_1$–$C_6$)alkoxy, benzyloxycarbonyl($C_1$–$C_6$)alkoxy, ($C_1$–$C_6$)alkoxycarbonyl($C_1$–$C_6$)alkoxy, ($C_6$–$C_{10}$)aryl, amino, amino($C_1$–$C_6$)alkyl, ($C_1$–$C_6$)alkoxycarbonylamino, ($C_6$–$C_{10}$)aryl($C_1$–$C_6$)alkoxycarbonylamino, ($C_1$–$C_6$)alkylamino, (($C_1$–$C_6$)alkyl)$_2$amino, ($C_1$–$C_6$)alkylamino($C_1$–$C_6$)alkyl, (($C_1$–$C_6$)alkyl)$_2$amino($C_1$–$C_6$)alkyl, hydroxy, ($C_1$–$C_6$)alkoxy, carboxy, carboxy($C_1$–$C_6$)alkyl, ($C_1$–$C_6$)alkoxycarbonyl, ($C_1$–$C_6$)alkoxycarbonyl($C_1$–$C_6$)alkyl, ($C_1$–$C_6$)alkoxy-CO—NH—, ($C_1$–$C_6$)alkyl-CO—NH—, cyano, ($C_5$–$C_9$)heterocycloalkyl, amino-CO—NH—, ($C_1$–$C_6$)alkylamino-CO—NH—, (($C_1$–$C_6$)alkyl)$_2$amino-CO—NH—, ($C_6$–$C_{10}$)arylamino-CO—NH—, ($C_5$–$C_9$)heteroarylamino-CO—NH—, ($C_1$–$C_6$)alkylamino-CO—NH—($C_1$–$C_6$)alkyl, (($C_1$–$C_6$)alkyl)$_2$amino-CO—NH—($C_1$–$C_6$)alkyl, ($C_6$–$C_{10}$)arylamino-CO—NH—($C_1$–$C_6$)alkyl, ($C_5$–$C_9$)heteroarylamino-CO—NH—($C_1$–$C_6$)alkyl, ($C_1$–$C_6$)alkylsulfonyl, ($C_1$–$C_6$)alkylsulfonylamino, ($C_1$–$C_6$)alkylsulfonylamino($C_1$–$C_6$)alkyl, ($C_6$–$C_{10}$)arylsulfonyl, ($C_6$–$C_{10}$)arylsulfonylamino, ($C_6$–$C_{10}$)arylsulfonylamino($C_1$–$C_6$)alkyl, ($C_1$–$C_6$)alkylsulfonylamino, ($C_1$–$C_6$)alkylsulfonylamino($C_1$–$C_6$)alkyl, ($C_5$–$C_9$)heteroaryl or ($C_2$–$C_9$)heterocycloalkyl;

with the proviso that $R^5$ must be substituted by the group of formula II.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The term "Oxone®" is a name of a monopersulfate compound used in this invention, having the formula 2 $KHSO_5 \cdot KHSO_4 K_2SO_4$, and sold by Aldrich Chemical Company, P.O. Box 2060, Milwaukee, Wis. 53201, USA.

The term "alkyl", as used herein, unless otherwise indicated, includes saturated monovalent hydrocarbon radicals having straight or branched moieties or combinations thereof.

The term "alkoxy", as used herein, includes O-alkyl groups wherein "alkyl" is defined above.

The term "halo", as used herein, unless otherwise indicated, includes fluoro, chloro, bromo or iodo.

The compounds of this invention may contain double bonds. When such bonds are present, the compounds of the invention exist as cis and trans configurations and as mixtures thereof.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Unless otherwise indicated, halogen includes fluorine, chlorine, bromine, and iodine.

$(C_2-C_9)$Heterocycloalkyl when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said $(C_2-C_9)$heterocycloalkyl rings is through a carbon or a $sp^3$ hybridized nitrogen heteroatom.

$(C_2-C_9)$Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2, 3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said $(C_2-C_9)$heterocycloalkyl rings is through a carbon atom or a $sp^3$ hybridized nitrogen heteroatom.

$(C_6-C_{10})$aryl when used herein refers to phenyl or naphthyl.

Compounds of formula (I) may be administered in a pharmaceutically acceptable form either alone or in combination with one or more additional agents which modulate a mammalian immune system or with antiinflammatory agents. These agents may include but are not limited to cyclosporin A (e.g. Sandimmune® or Neoral®, rapamycin, FK-506 (tacrolimus), leflunomide, deoxyspergualin, mycophenolate (e.g. Cellcept®), azathioprine (e.g. Imuran®), daclizumab (e.g. Zenapax®. OKT3 (e.g. Orthoclone®), AtGam, aspirin, acetaminophen, ibuprofen, naproxen, piroxicam, and antiinflammatory steroids (e.g. prednisolone or dexamethasone). These agents may be administered as part of the same or separate dosage forms, via the same or different routes of administration, and on the same or different administration schedules according to standard pharmaceutical practice.

The compounds of this invention include all conformational isomers (e.g., cis and trans isomers. The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. In this regard, the invention includes both the E and Z configurations. The compounds of formula I may also exist as tautomers. This invention relates to the use of all such tautomers and mixtures thereof.

This invention also encompasses pharmaceutical compositions containing prodrugs of compounds of the formula I. This invention also encompasses methods of treating or preventing disorders that can be treated or prevented by the inhibition of protein kinases, such as the enzyme Janus Kinase 3 comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of formula I through the carbonyl carbon prodrug sidechain.

Preferred compounds of formula I include those wherein $R^5$ is $(C_2-C_9)$heterocycloalkyl optionally substituted by one to three groups selected from deuterium, hydroxy, $(C_1-C_6)$alkyl, halo, $(C_1-C_6)$alkoxy and a group of formula II.

Other preferred compounds of formula I include those wherein a is 0; b is 1; X is carbonyl; c is 0; d is 0; e is 0; f is 0; and g is 0.

Other preferred compounds of formula I include those wherein a is 0; b is 1; X is carbonyl; c is 0; d is 1; e is 0; f is 0, and g is 0.

Other preferred compounds of formula I include those wherein a is 0; b is 1; X is carbonyl; c is 1; d is 0; e is 0; f is 0; and g is 0.

Other preferred compounds of formula I include those wherein a is 0; b is 1; X is —C(=N=cyano)-; c is 1; d is 0; e is 0; f is 0; and g is 0.

Other preferred compounds of formula I include those wherein a is 0; b is 0; c is 0; d is 0; e is 0; f is 0; g is 1; and Z is —C(O)—O—.

Other preferred compounds of formula I include those wherein a is 0; b is 1; X is S(O)$_n$; n is 2; c is 0; d is 0; e is 0; f is 0; and g is 0.

Other preferred compounds of formula I include those wherein a is 0; b is 1; X is S(O)$_n$; n is 2; c is 0; d is 2; e is 0; f is 1; g is 1; and Z is carbonyl.

Other preferred compounds of formula I include those wherein a is 0; b is 1; X is S(O)$_n$; n is 2; c is 0; d is 2; e is 0; f is 1; and g is 0.

Other preferred compounds of formula I include those wherein a is 0; b is 1; X is carbonyl; c is 1; d is 0; e is 1; Y is S(O)$_n$; n is 2; f is 0; and g is 0.

Other preferred compounds of formula I include those wherein a is 0; b is 1; X is S(O)$_n$; n is 2; c is 1; d is 0; e is 0; f is 0; and g is 0.

Other preferred compounds of formula I include those wherein a is 1; b is 1; X is carbonyl; c is 1; d is 0; e is 0; f is 0; and g is 0.

Other preferred compounds of formula I include those wherein a is 0; b is 1; X is S(O)$_n$; c is 0; d is 1; e is 1; Y is S(O)$_n$; n is 2; f is 0; and g is 0.

Other preferred compounds of formula I include those wherein a is 0; b is 1; X is S(O)$_n$; c is 0; d is 1; e is 1; Y is S(O)$_n$; n is 2; f is 1; and g is 0.

Other preferred compounds of formula I include those wherein a is 0; b is 1; X is oxygen; c is 0; d is 1; e is 1; Y is S(O)$_n$; n is 2; f is 1; and g is 0.

Other preferred compounds of formula I include those wherein a is 0; b is 1; X is oxygen; c is 0; d is 1; e is 1; Y is S(O)$_n$; n is 2; f is 0; and g is 0.

Other preferred compounds of formula I include those wherein a is 0; b is 1; X is carbonyl; c is 1; d is 1; e is 1; Y is S(O)$_n$; f is 0; and g is 0.

Other preferred compounds of formula I include those wherein a is 0; b is 1; X is carbonyl; c is 1; d is 1; e is 1; Y is S(O)$_n$; n is 2; f is 1; and g is 0.

Other preferred compounds of formula I include those wherein $R^{12}$ is (C$_6$–C$_{10}$)aryl or (C$_2$–C$_9$)heteroaryl wherein the aryl or heteroaryl group is optionally substituted by one to four groups consisting of hydrogen, halo, hydroxy, carboxy, trifluormethyl, (C$_1$–C$_6$)alkyl, (C$_1$–C$_6$)alkoxy, (C$_1$–C$_6$)alkyl-CO—NH—, amino, amino(C$_1$–C$_6$)alkyl, (C$_1$–C$_6$)alkylamino, ((C$_1$–C$_6$)alkyl)$_2$amino, cyano, amino-CO—NH—, (C$_1$–C$_6$)alkylamino-CO—NH—, ((C$_1$–C$_6$)alkyl)$_2$amino-CO—NH—, (C$_5$–C$_9$)heteroarylamino-CO—NH—, (C$_1$–C$_6$)alkylsulfonyl, (C$_1$–C$_6$)alkylsulfonylamino, (C$_6$–C$_{10}$)arylsulfonylamino, (C$_1$–C$_6$)alkylsulfonylamino, and (C$_1$–C$_6$)alkoxy-CO—NH—.

Specific preferred compounds of formula I include those wherein said compound is selected from the group consisting of:

4-{4-Methyl-3-[methyl-(7H-pyrrolo[2,3-d]pyrimidin-4-yl)-amino]-piperidin-1-ylmethyl}-benzenesulfonamide;

4-Methyl-3-[methyl-(7H-pyrrolo[2,3-d]pyrimidin-4-yl)-amino]-piperidine-1-carboxylic acid (4-sulfamoyl-phenyl)-amide;

4-Methyl-3-[methyl-(7H-pyrrolo[2,3-d]pyrimidin-4-yl)-amino]-piperidine-1-carboxylic acid (4-nitro-phenyl)-amide;

-{4-Methyl-3-[methyl-(7H-pyrrolo[2,3-d]pyrimidin-4-yl)-amino]-piperidin-1-yl}-2-tetrazol-1-yl-ethanone;

4-Methyl-3-[methyl-(7H-pyrrolo[2,3-d]pyrimidin-4-yl)-amino]-piperidine-1-carboxylic acid (4-methylsulfamoyl-phenyl)-amide;

(3-Hydroxy-pyrrolidin-1-yl)-{4-methyl-3-[methyl-(7H-pyrrolo[2,3-d]pyrimidin-4-yl)-amino]-piperidin-1-yl}-methanone;

[2-({4-Methyl-3-[methyl-(7H-pyrrolo[2,3-d]pyrimidin-4-yl)-amino]-piperidine-1-carbonyl}-amino)-thiazol-4-yl]-acetic acid;

Methyl-(4-methyl-5'-nitro-3,4,5,6-tetrahydro-2H-[1,2']bipyridinyl-3-yl)-(7H-pyrrolo[2,3-d]pyrimidin-4-yl)-amine;

5-(2-{4-Methyl-3-[methyl-(7H-pyrrolo[2,3-d]pyrimidin-4-yl)-amino]-piperidin-1-yl}-2-oxo-ethyl)-thiazolidine-2,4-dione;

{4-Methyl-3-[methyl-(7H-pyrrolo[2,3-d]pyrimidin-4-yl)-amino]-piperidin-1-yl}-thiazolidin-3-yl-methanone;

Methyl-[4-methyl-1-(5-nitro-thiazol-2-yl)-piperidin-3-yl]-(7H-pyrrolo[2,3-d]pyrimidin-4-yl)-amine;

[2-({4-Methyl-3-[methyl-(7H-pyrrolo[2,3-d]pyrimidin-4-yl)-amino]-piperidine-1-carbonyl}-amino)-thiazol-4-yl]-acetic acid ethyl ester;

4-Methyl-3-[methyl-(7H-pyrrolo[2,3-d]pyrimidin-4-yl)-amino]-piperidine-1-carboxylic acid (4-methanesulfonyl-phenyl)-amide;

4-Methyl-3-[methyl-(7H-pyrrolo[2,3-d]pyrimidin-4-yl)-amino]-piperidine-1-carboxylic acid thiazol-2-ylamide;

4-Methyl-3-[methyl-(7H-pyrrolo[2,3-d]pyrimidin-4-yl)-amino]-piperidine-1-carboxylic acid (4-cyano-phenyl)-amide;

{4-Methyl-3-[methyl-(7H-pyrrolo[2,3-d]pyrimidin-4-yl)-amino]-piperidin-1-yl}-pyrrolidin-1-yl-methanone;

Furan-2-carboxylic acid (2-{4-methyl-3-[methyl-(7H-pyrrolo[2,3-d]pyrimidin-4-yl)-amino]-piperidine-1-sulfonyl}-ethyl)-amide;

{4-Methyl-3-[methyl-(7H-pyrrolo[2,3-d]pyrimidin-4-yl)-amino]-piperidin-1-yl}(tetrahydro-furan-3-yl)-methanone;

4-Methyl-3-[methyl-(7H-pyrrolo[2,3-d]pyrimidin-4-yl)-amino]-piperidine-1-carboxylic acid isoxazol-3-ylamide;

4-Methyl-3-[methyl-(7H-pyrrolo[2,3-d]pyrimidin-4-yl)-amino]-piperidine-1-carboxylic acid (6-cyano-pyridin-3-yl)-amide;

4-Methyl-3-[methyl-(7H-pyrrolo[2,3-d]pyrimidin-4-yl)-amino]-3,4,5,6-tetrahydro-2H-[1,2']bipyridinyl-5'-carbonitrile 4-Methyl-3-[methyl-(7H-pyrrolo[2,3-d]pyrimidin-4-yl)-amino]-piperidine-1-carboxylic acid (4-methyl-thiazol-2-yl)-amide;

2-Cyclopropyl-1-{4-methyl-3-[methyl-(7H-pyrrolo[2,3-d]pyrimidin-4-yl)-amino]-piperidin-1-yl}-ethanone;

Cyclopentyl-{4-methyl-3-[methyl-(7H-pyrrolo[2,3-d]pyrimidin-4-yl)-amino]-piperidin-1-yl}-Methanone;

4-Methyl-3-[methyl-(7H-pyrrolo[2,3-d]pyrimidin-4-yl)-amino]-piperidine-1-carboxylic acid (3-methyl-isoxazol-4-yl)-amide;

[4-({4-Methyl-3-[methyl-(7H-pyrrolo[2,3-d]pyrimidin-4-yl)-amino]-piperidine-1-carbonyl}-amino)-phenyl]-acetic acid;

[1-(5-Amino-thiazol-2-yl)-4-methyl-piperidin-3-yl]-methyl-(7H-pyrrolo[2,3-d]pyrimidin-4-yl)-amine;

4-Methyl-3-[methyl-(7H-pyrrolo[2,3-d]pyrimidin-4-yl)-amino]-piperidine-1-carboxylic acid (3-methyl-isothiazol-5-yl)-amide;

3-{4-Methyl-3-[methyl-(7H-pyrrolo[2,3-d]pyrimidin-4-yl)-amino]-piperidine-1-carbonyl}-cyclopentanone;

4-Methyl-3-[methyl-(7H-pyrrolo[2,3-d]pyrimidin-4-yl)-amino]-piperidine-1-carboxylic acid benzyl-methyl-amide; and 4-Methyl-3-[methyl-(7H-pyrrolo[2,3-d]pyrimidin-4-yl)-amino]-piperidine-1-carboxylic acid dimethylamide.

The present invention also relates to a pharmaceutical composition for (a) treating or preventing a disorder or condition selected from organ transplant rejection, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia, and other autoimmune diseases or (b) the inhibition of protein kinases or Janus Kinase 3 (JAK3) in a mammal, including a human, comprising an amount of a compound of formula I or a pharmaceutically acceptable salt thereof, effective in such disorders or conditions and a pharmaceutically acceptable carrier.

The present invention also relates to a method for the inhibition of protein tyrosine kinases or Janus Kinase 3 (JAK3) in a mammal, including a human, comprising administering to said mammal an effective amount of a compound of formula I or a pharmaceutically acceptable salt thereof.

The present invention also relates to a method for treating or preventing a disorder or condition selected from organ transplant rejection, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia, and other autoimmune diseases in a mammal, including a human, comprising administering to said mammal an amount of a compound of formula I or a pharmaceutically acceptable salt thereof, effective in treating such a condition.

DETAILED DESCRIPTION OF THE INVENTION

The following reaction Schemes illustrate the preparation of the compounds of the present invention. Unless otherwise indicated $R^2$, $R^3$, $R^4$ and $R^5$ in the reaction Schemes and the discussion that follow are defined as above.

PREPARATION A

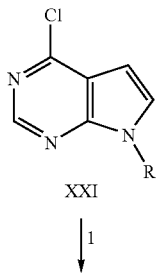

XXI

↓ 1

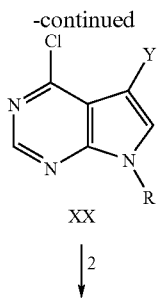

XX

↓ 2

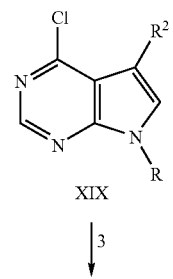

XIX

↓ 3

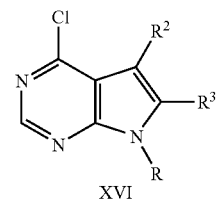

XVI

PREPARATION B

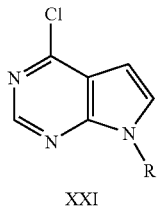

XXI

↓ 1

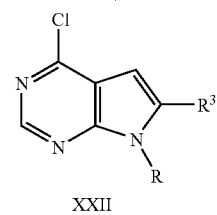

XXII

↓ 2

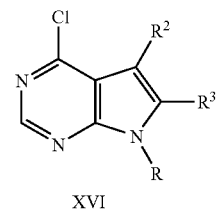

XVI

-continued
PREPARATION C
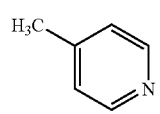
XXXI
↓ 1
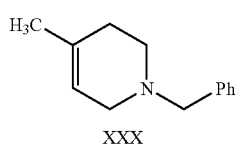
XXX
↓ 2
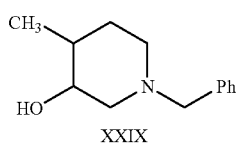
XXIX
↓ 3
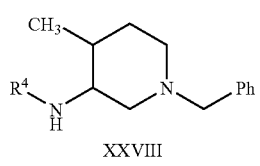
XXVIII
SCHEME 1
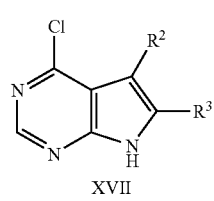
XVII
↓ 1
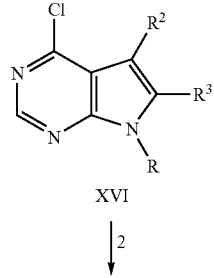
XVI
↓ 2
-continued
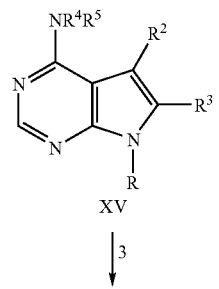
XV
↓ 3
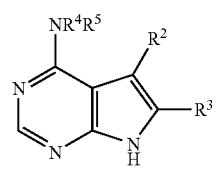
I
SCHEME 2
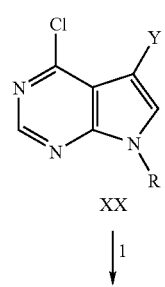
XX
↓ 1
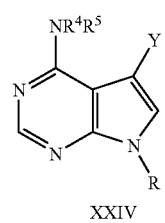
XXIV
↓ 2
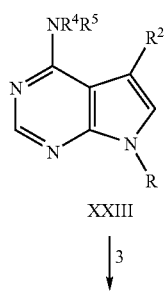
XXIII
↓ 3

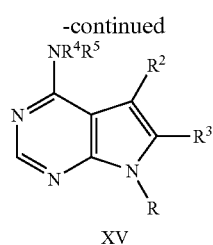

XV

SCHEME 3

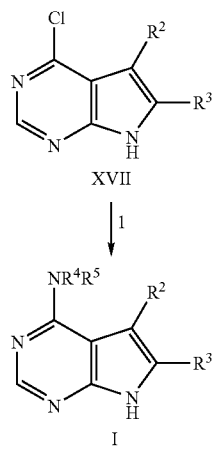

In reaction 1 of Preparation A, the 4-chloropyrrolo[2,3-d]pyrimidine compound of formula XXI, wherein R is hydrogen or a protecting group such as benzenesulfonyl or benzyl, is converted to the 4-chloro-5-halopyrrolo[2,3-d]pyrimidine compound of formula XX, wherein Y is chloro, bromo or iodo, by reacting XXI with N-chlorosuccinimide, N-bromosuccinimide or N-iodosuccinimide. The reaction mixture is heated to reflux, in chloroform, for a time period between about 1 hour to about 3 hours, preferably about 1 hour. Alternatively, in reaction 1 of Preparation A, the 4-chloropyrrolo[2,3-d]pyrimidine of formula XXI, wherein R is hydrogen, is converted to the corresponding 4-chloro-5-nitropyrrolo[2,3-d]pyrimidine of formula XX, wherein Y is nitro, by reacting XXI with nitric acid in sulfuric acid at a temperature between about −10° C. to about 10° C., preferably about 0° C., for a time period between about 5 minutes to about 15 minutes, preferably about 10 minutes. The compound of formula XXI, wherein Y is nitro, is converted to the corresponding 4-chloro-5-aminopyrrolo[2,3-d]pyrimidine of the formula XX, wherein Y is amino, by reacting XXI under a variety of conditions known to one skilled in the art such as palladium hydrogenolysis or tin(IV)chloride and hydrochloric acid.

In reaction 2 of Preparation A, the 4-chloro-5-halopyrrolo[2,3-d]pyrimidine compound of formula XX, wherein R is hydrogen, is converted to the corresponding compound of formula XIX, wherein $R^2$ is $(C_1–C_6)$alkyl or benzyl, by treating XX with N-butyllithium, at a temperature of about −78° C., and reacting the dianion intermediate so formed with an alkylhalide or benzylhalide at a temperature between about −78° C. to room temperature, preferably room temperature. Alternatively, the dianion so formed is reacted with molecular oxygen to form the corresponding 4-chloro-5-hydroxypyrrolo[2,3-d]pyrimidine compound of formula XIX, wherein $R^2$ is hydroxy. The compound of formula XX, wherein Y is bromine or iodine and R is benzenesulfonate, is converted to the compound of formula XIX, wherein $R^2$ is $(C_6–C_{12})$aryl or vinyl, by treating XX with N-butyllithium, at a temperature of about −78° C., followed by the addition of zinc chloride, at a temperature of about −78° C. The corresponding organo zinc intermediate so formed is then reacted with aryliodide or vinyl iodide in the presence of a catalytic quantity of palladium. The reaction mixture is stirred at a temperature between about 50° C. to about 80° C., preferably about 70° C., for a time period between about 1 hour to about 3 hours, preferably about 1 hour.

In reaction 3 of Preparation A, the compound of formula XIX is converted to the corresponding compound of formula XVI by treating XIX with N-butyllithium, lithium diisopropylamine or sodium hydride, at a temperature of about −78° C., in the presence of a polar aprotic solvent, such as tetrahydrofuran. The anionic intermediate so formed is further reacted with (a) alkylhalide or benzylhalide, at a temperature between about −78° C. to room temperature, preferably −78° C., when $R^3$ is alkyl or benzyl; (b) an aldehyde or ketone, at a temperature between about −78° C. to room temperature, preferably −78° C., when $R^3$ is alkoxy; and (c) zinc chloride, at a temperature between about −78° C. to room temperature, preferably −78° C., and the corresponding organozinc intermediate so formed is then reacted with aryliodide or vinyl iodide in the presence of a catalytic quantity of palladium. The resulting reaction mixture is stirred at a temperature between about 50° C. to about 80° C., preferably about 70° C., for a time period between about 1 hour to about 3 hours, preferably about 1 hour. Alternatively, the anion so formed is reacted with molecular oxygen to form the corresponding 4-chloro-6-hydroxypyrrolo[2,3-d]pyrimidine compound of formula XVI, wherein $R^3$ is hydroxy.

In reaction 1 of Preparation B, the 4-chloropyrrolo[2,3-d]pyrimidine compound of formula XXI is converted to the corresponding compound of formula XXII, according to a procedure analogous to that described above in reaction 3 of Preparation A.

In reaction 2 of Preparation B, the compound of formula XXII is converted to the corresponding compound of formula XVI, according to procedures analogous to that described above in reactions 1 and 2 of Preparation A.

In reaction 1 of Preparation C, the 4-methylpyridine compound of formula XXXI is converted to the corresponding compound of formula XXX by first alkylating XXXI with benzylchloride in the presence of a polar aprotic solvent, such as acetone. The reaction mixture is stirred at a temperature between about 40° C. to about 80° C. for a time period between about 4 hours to about 24 hours. The pyridinium intermediate so formed is then reduced with a reducing agent, such as sodium borohydride, in the presence of a polar protic solvent, such as methanol, ethanol, water or mixtures thereof. The reaction is stirred at a temperature between about 0° C. to a about room temperature, for a time period between about 18 hours to 24 hours.

In reaction 2 of Preparation C, the compound of formula XXX is converted to the corresponding compound of formula XXIX by treating XXX with borotrifluoride etherate in the presence of a reducing agent and an aprotic solvent, such as tetrahydrofuran. The reaction mixture is stirred at a temperature between about 0° C. to room temperature, for a time period between about 1 hour to about 3 hours. The intermediate complex so formed is then basified with aqueous sodium hydroxide and then treated with an oxidizing agent, such as hydrogen peroxide or Oxone®, at a temperature between about 0° C. to room temperature, for a time period between about 12 hours to about 24 hours.

In reaction 3 of Preparation C, the compound of formula XXIX is treated with an oxidizing agent, such as chromium oxide or dimethylsulfoxide, oxalylchloride or $SO_3$-pyridine complex, for a time period between about 1 hour to 3 hours, at ambient temperature. The ketone intermediate so formed, is then treated with an amine ($R^4$—$NH_2$) in the presence of an acid, such as acetic acid, at about room temperature, for a time period between about 2 to about 24 hours, in an organic solvent such as methanol, ethanol or tetrahydrofuran. The corresponding imine intermediate so formed is then treated with a reducing agent, such as sodium borohydride or sodium cyanoborohydride or sodium triacetoxyborohydride, at ambient temperature, for a time period about 2 to about 24 hours.

In reaction 1 of Scheme 1, the 4-chloropyrrolo[2,3-d]pyrimidine compound of formula XVII is converted to the corresponding compound of formula XVI, wherein R is benzenesulfonyl or benzyl, by treating XVII with benzenesulfonyl chloride, benzylchloride or benzylbromide in the presence of a base, such as sodium hydride or potassium carbonate, and a polar aprotic solvent, such as dimethylformamide or tetrahydrofuran. The reaction mixture is stirred at a temperature between about 0° C. to about 70° C., preferably about 30° C., for a time period between about 1 hour to about 3 hours, preferably about 2 hours.

In reaction 2 of Scheme 1, the 4-chloropyrrolo[2,3-d]pyrimidine compound of formula XVI is converted to the corresponding 4-aminopyrrolo[2,3-d]pyrimidine compound of formula XV by coupling XVI with an amine of the formula $HNR^4R^5$. The reaction is carried out in an alcohol solvent, such as tert-butanol, methanol or ethanol, or other high boiling organic solvents, such as dimethylformamide, triethylamine, 1,4-dioxane or 1,2-dichloroethane, at a temperature between about 60° C. to about 120° C., preferably about 80° C. Typical reaction times are between about 2 hours to about 48 hours, preferably about 16 hours. When $R^5$ is a nitrogen containing heterocycloalkyl group, each nitrogen must be protected by a protecting group, such a benzyl. Removal of the $R^5$ protecting group is carried out under conditions appropriate for that particular protecting group in use which will not affect the R protecting group on the pyrrolo[2,3-d]pyrimidine ring. Removal of the $R^5$ protecting group, when benzyl, is carried out in an alcohol solvent, such as ethanol, in the present of hydrogen and a catalyst, such as palladium hydroxide on carbon. The $R^5$ nitrogen containing hetrocycloalkyl group so formed may be further reacted with a variety of different electrophiles of formula II. For urea formation, electrophiles of formula II such as isocyanates, carbamates and carbamoyl chlorides are reacted with the $R^5$ nitrogen of the heteroalkyl group in a solvent, such as acetonitrile or dimethylformamide, in the presence of a base, such as sodium or potassium carbonate, at a temperature between about 20° C. to about 100° C. for a time period between about 24 hours to about 72 hours. For amide and sulfonamide formation, electrophiles of formula II, such as acylchlorides and sulfonyl chlorides, are reacted with the $R^5$ nitrogen of the heteroalkyl group in a solvent such as methylene chloride in the presence of a base such as pyridine at ambient temperatures for a time period between about 12 hours to about 24 hours. Amide formation may also be carried out by reacting a carboxylic acid with the heteroalkyl group in the presence of a carbodiimide such as 1-(3-dimethylaminopropyl)-3-ethylcarbodiimide in a solvent such as methylene chloride at ambient temperatures for 12–24 hours. For alkyl formation, electrophiles of formula II, such as α,β-unsaturated amides, acids, nitriles, esters, and α-halo amides, are reacted with the $R^5$ nitrogen of the heteroalkyl group in a solvent such as methanol at ambient temperatures for a time period between about 12 hours to about 18 hours. Alkyl formation may also be carried out by reacting aldehydes with the heteroalkyl group in the presence of a reducing agent, such as sodium cyanoborohydride, in a solvent, such as methanol, at ambient temperature for a time period between about 12 hours to about 18 hours.

In reaction 3 of Scheme 1, removal of the protecting group from the compound of formula XV, wherein R is benzenesulfonyl, to give the corresponding compound of formula I, is carried out by treating XV with an alkali base, such as sodium hydroxide or potassium hydroxide, in an alcohol solvent, such as methanol or ethanol, or mixed solvents, such as alcohol/tetrahydrofuran or alcohol/water. The reaction is carried out at room temperature for a time period between about 15 minutes to about 1 hour, preferably 30 minutes. Removal of the protecting group from the compound of formula XV, wherein R is benzyl, is conducted by treating XV with sodium in ammonia at a temperature of about −78° C. for a time period between about 15 minutes to about 1 hour.

In reaction 1 of Scheme 2, the 4-chloropyrrolo[2,3-d]pyrimidine compound of formula XX is converted to the corresponding 4-aminopyrrolo[2,3-d]pyrimidine compound of formula XXIV, according to a procedure analogous to that described above in reaction 2 of Scheme 1.

In reaction 2 of Scheme 2, the 4-amino-5-halopyrrolo[2,3-d]pyrimidine compound of formula XXIV, wherein R is benzenesulfonate and Z is bromine or iodine, is converted to the corresponding compound of formula XXIII by reacting XXIV with (a) arylboronic acid, when $R^2$ is aryl, in an aprotic solvent, such tetrahydrofuran or dioxane, in the presence of a catalytic quantity of palladium (0) at a temperature between about 50° C. to about 100° C., preferably about 70° C., for a time period between about 2 hours to about 48 hours, preferably about 12 hours; (b) alkynes, when $R^2$ is alkynyl, in the presence of a catalytic quantity of copper (I) iodide and palladium (0), and a polar solvent, such as dimethylformamide, at room temperature, for a time period between about 1 hour to about 5 hours, preferably about 3 hours; and (c) alkenes or styrenes, when $R^2$ is vinyl or styrenyl, in the presence of a catalytic quantity of palladium in dimethylformamide, dioxane or tetrahydrofuran, at a temperature between about 80° C. to about 100° C., preferably about 100° C., for a time period between about 2 hours to about 48 hours, preferably about 48 hours.

In reaction 3 of Scheme 2, the compound of formula XXIII is converted to the corresponding compound of formula XV, according to a procedure analogous to that described above in reaction 3 of Preparation A.

In reaction 1 of Scheme 3, the compound of formula XVII is converted to the corresponding compound of formula I, according to a procedure analogous to that described above in reaction 2 of Scheme 1.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

Aerosol formulations for treatment of the conditions referred to above (e.g., asthma) in the average adult human are preferably arranged so that each metered dose or "puff" of aerosol contains 20 µg to 1000 µg of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

A compound of formula (I) administered in a pharmaceutically acceptable form either alone or in combination with one or more additional agents which modulate a mammlian immune system or with antiinflammatory agents, agents which may include but are not limited to cyclosporin A (e.g. Sandimmune® or Neoral®), rapamycin, FK-506 (tacrolimus), leflunomide, deoxyspergualin, mycophenolate (e.g. Cellcept®, azathioprine (e.g. Imuran®), daclizumab (e.g. Zenapax®), OKT3 (e.g. Orthocolone®), AtGam, aspirin, acctaminophen, ibuprofen, naproxen, piroxicam, and antiinflmmatory steroids (e.g. prednisolone or dexamethasone); and such agents may be administered as part of the same or separate dosage forms, via the same or different routes of administration, and on the same or different administration schedules according to standard pharmaceutical practice.

FK506 (Tacrolimus) is given orally at 0.10–0.15 mg/kg body weight, every 12 hours, within first 48 hours postoperative. Does is monitored by serum Tacrolimus trough levels.

Cyclosporin A (Sandimmune oral or intravenous formulation, or Neoral®, oral solution or capsules) is given orally at 5 mg/kg body weight, every 12 hours within 48 hours postoperative. Dose is monitored by blood Cyclosporin A trough levels.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397.

The ability of the compounds of formula I or their pharmaceutically acceptable salts to inhibit Janus Kinase 3 and, consequently, demonstrate their effectiveness for treating disorders or conditions characterized by Janus Kinase 3 is shown by the following in vitro assay tests.

Biological Assay

JAK3 (JH1:GST) Enzymatic Assay

The JAK3 kinase assay utilizes a protein expressed in baculovirus-infected SF9 cells (a fusion protein of GST and the catalytic domain of human JAK3) purified by affinity chromatography on glutathione-Sepaharose. The substrate for the reaction is poly-Glutamic acid-Tyrosine (PGT (4:1), Sigma catalog # $PO_{275}$), coated onto Nunc Maxi Sorp plates at 100 μg/ml overnight at 37° C. The morning after coating, the plates are washed three times and JAK3 is added to the wells containing 100 μl of kinase buffer (50 mM HEPES, pH 7.3, 125 mM NaCl, 24 mM MgCl2)+0.2 uM ATP+1 mM Na orthovanadate.) The reaction proceeds for 30 minutes at room temperature and the plates is washed three more times. The level of phosphorylated tyrosine in a given well is quantitated by standard ELISA assay utilizing an anti-phosphotyrosine antibody (ICN PY20, cat. #69-151-1).

Inhibition of Human IL-2 Dependent T-Cell Blast Proliferation

This screen measures the inhibitory effect of compounds on IL-2 dependent T-Cell blast proliferation in vitro. Since signaling through the IL-2 receptor requires JAK-3, cell active inhibitors of JAK-3 should inhibit IL-2 dependent T-Cell blast proliferation.

The cells for this assay are isolated from fresh human blood. After separation of the mononuclear cells using Accuspin System-Histopaque-1077 (Sigma # A7054), primary human T-Cells are isolated by negative selection using Lympho-Kwik T (One Lambda, Inc., Cat # LK-50T). T-Cells are cultured at $1-2\times10^6$/ml in Media (RPMI+10% heat-inactivated fetal calf serum (Hyclone Cat # A-1111-L)+1% Penicillin/Streptomycin (Gibco)) and induce to proliferate by the addition of 10 ug/ml PHA (Murex Diagnostics, Cat # HA 16). After 3 days at 37° C. in 5% $CO_2$, cells are washed 3 times in Media, resuspended to a density of $1-2\times10^6$ cells/ml in Media plus 100 Units/ml of human recombinant IL-2 (R&D Systems, Cat # 202-IL). After 1 week the cells are IL-2 dependent and can be maintained for up to 3 weeks by feeding twice weekly with equal volumes of Media+100 Units/ml of IL-2.

To assay for a test compounds ability to inhibit IL-2 dependent T-Cell proliferation, IL-2 dependent cells are washed 3 times, resuspended in media and then plated (50,000 cells/well/0.1 ml) in a Flat-bottom 96-well microtiter plate (Falcon # 353075). From a 10 mM stock of test compound in DMSO, serial 2-fold dilutions of compound are added in triplicate wells starting at 10 uM. After one hour, 10 Units/ml of IL-2 is added to each test well. Plates are then incubated at 37° C., 5% $CO_2$ for 72 hours. Plates are then pulsed with $^3$H-thymidine (0.5 uCi/well) (NEN Cat # NET-027A), and incubated an additional 18 hours. Culture plates are then harvested with a 96-well plate harvester and the amount of $^3$H-thymidine incorporated into proliferating cells is determined by counting on a Packard Top Count scintillation counter. Data is analyzed by plotting the % inhibition of proliferation verses the concentration of test compound. An $IC_{50}$ value (uM) is determined from this plot.

The following Examples illustrate the preparation of the compounds of the present invention but it is not limited to the details thereof. Commercial reagents were utilized without further purification. THF refers to tetrahydrofuran. DMF refers to N,N-dimethylformamide. Low Resolution Mass Spectra (LRMS) were recorded on either a Hewlett Packard 5989®, utilizing chemical ionization (ammonium), or a Fisons (or Micro Mass) Atmospheric Pressure Chemical Ionization (APCI) platform which uses a 50/50 mixture of acetonitrile/water with 0.1% formic acid as the ionizing agent. Room or ambient temperature refers to 20–25° C.

EXAMPLE 1

Furan-2-yl-{4-methyl-3-[methyl-(7H-Pyrrolo[2,3-d]pyrimidin-4-yl)-amino]-piperidin-1-yl}-methanone Method A 1-Benzyl-4-methyl-pyridinium chloride To a stirred solution of 4-methylpyridine (26 mL/0.268 mol) in 70 mL of acetone was added 31 mL (0.268 mol) of benzylchloride. The resulting mixture was stirred at 50° C. for 18 hours. After cooling to room temperature, the reaction was filtered, washed with acetone and dried under reduced pressure affording 38 g of the title compound. The filtrate was concentrated under reduced pressure producing an additional 5.6 grams of the title compound (74% combined yield). LRMS: 184.

Method B

1-Benzyl-4-methyl-1,2,3,6-tetrahydro-pyridine

To a stirred solution of the product from Method A (38 grams/0.171 mol) dissolved in 140 mL of 10:1 ethanol/water at 0° C. was added 16 grams (0.427 mol) of sodium borohydride portion-wise over 25 minutes. The resulting mixture stirred for 18 hours at room temperature, at which time, the reaction was quenched upon addition of 100 mL of water. The reaction mixture was filtered, the filter cake washed with water and ethylacetate, and the combined filtrates concentrated under reduced pressure to remove the organics. The residue was diluted with water (100 mL) and extracted 3 times with 150 mL with ethylacetate. The combined ethylacetate extracts were dried over $Na_2SO_4$ and concentrated to dryness in vacuo affording 32 grams (100%) of the title compound as a yellow oil. LRMS: 188 (M+1).

Method C

1-Benzyl-4-methyl-piperidin-3-ol

To a solution of the product from Method B (72.45 grams/0.387 mol) dissolved in 240 mL of THF was added 21.4 grams of $NaBH_4$ and the mixture cooled to 0° C. A solution of borontrifluoride etherate (109.4 mL dissolved in 200 mL of THF) was then added dropwise over 1.5 hours. Once added, the reaction mixture was brought to room temperature and stirred for 2 hours. The reaction was again cooled to 0° C. and 29.3 mL of water were added dropwise over 15 minutes followed by dropwise addition of 2N sodium hydroxide (97.5 mL) over 20 minutes. The resulting mixture stirred at 0° C. for 40 minutes and was then brought to room temperature. Hydrogen peroxide (30%) (97.5 mL) was added dropwise at a rate so as not to exceed 50° C. in the reaction mixture (approximately 30 minutes). When the addition was complete, the reaction mixture stirred for 10 minutes, then was cooled to 0° C. Concentrated hydrochloric acid (97.5 mL) was added over 5 minutes, the reaction mixture was reduced to one third its volume in vacuo, and the pH adjusted to 9–10 with 6N sodium hydroxide (aq). The resulting mixture was extracted three times with ether, the combined ether layers dried over $MgSO_4$ and evaporated to dryness in vacuo affording 65.32 grams (79%) of the title compound as yellow oil. LRMS: 206.1 (M+1).

Alternative Method: To a solution of the product from Method B (18.7 grams/0.1 mol) in THF (150 mL) was added $NaBH_4$ (6.5 grams/0.170 mol) at room temperature under $N_2$. The slurry was cooled to 0° C., and $BF_3 \cdot OEt_2$ (15 mL, 16.8 grams/0.118 mol) in THF (25 mL) was slowly added through an addition funnel. The addition was kept slow enough to keep the temperature of the reaction mixture below 0° C. After the addition; the reaction mixture was stirred at 0° C. for 1 hour and room temperature for 1.5 hours. The reaction was re-cooled to 0° C. and water (50 mL) was added slowly to destroy the excess borane. The reaction was stirred at room temperature for 2 hours, followed by the addition of Oxone® (110 grams/0.343 mol) in water (500 mL) at 0° C. The reaction mixture was allowed to warm to room temperature and stirred overnight. The reaction was quenched upon addition of solid $NaHSO_3$ until all excess oxidant was destroyed (KI/starch test paper). The pH of the reaction mixture was 1–2. The reaction mixture was then extracted 3 times with 50 mL ethyl acetate, the aqueous layer adjusted to pH 12 with 6 N sodium hydroxide and extracted with ethyl acetate (4 times with 100 mL). The organic layer was washed with brine, dried over $Na_2SO_4$, and concentrated in vacuo affording 19.0 grams (92%) of the title compound as an oil. LRMS: 206.1 (M+1).

Method D

1-Benzyl-4-methyl-piperidin-3-ol-toluene-4-sulfonic acid salt

To a stirred solution of the product from Method C (65.32 grams/0.318 mol) dissolved in 175 mL of acetone and cooled to 0° C. was added a solution of para-toluenesulfonic acid monohydrate in 350 mL of acetone (dropwise) over 2 hours and the resulting mixture stirred at 0° C. for 1.5 hours. The precipitate was filtered and the filter cake washed with 90 mL of diisopropyl ether. The solid product was then dried in vacuo affording 58.55 grams (100%) of the title compound as a white solid. LRMS: 378.5 (M+1).

Method E

1-Benzyl-4-methyl-piperidin-3-one

To a solution of the product from Method D (9.8 grams/ 0.026 mol) and 31.7 mL of diisopropylethylamine dissolved in 250 mL of dichloromethane and cooled to 0° C. was added (dropwise) 12.4 grams of $SO_3$pyridine complex dissolved in 153 mL of dimethylsulfoxide over a 40 minute period. Once added, the reaction stirred for 1.5 hours at room temperature and was then quenched upon addition of 200 mL of saturated $NaHCO_3$ (aq). The dichloromethane was removed in vacuo and the remaining aqueous residue extracted four times with diisopropyl ether (150 mL). The combined ether layers were washed four times with water (100 mL), dried over $Na_2SO_4$ and concentrated to dryness in vacuo affording 3.81 grams (72.97%) of the title compound as yellow oil. LRMS: 204 (M+1).

Method F (1-Benzyl-4-methyl-piperidin-3-yl)-methyl-amine

To a stirred solution of the product from Method E (3.81 grams/0.019 mol) and 38 mL of 2.0 M methylamine in THF was added 2.2 mL of acetic acid and the resulting mixture stirred at room temperature for 1.5 hours. Triacetoxysodiumborohydride ($NaB(OAc)_3H$) (7.94 grams/0.038 mol) was added as a solid and the new mixture stirred at room temperature for 18 hours. The reaction was quenched with 2 N hydrochloric acid and the pH adjusted to 1. The reaction mixture was washed two times with ether, the aqueous layer then adjusted to pH of 12 with 6 N sodium hydroxide (aq) and extracted three times with dichloromethane The combined dichloromethane layers were dried over $Na_2SO_4$, filtered and evaporated to dryness in vacuo affording 3.51 grams (87.75%) of the title compound as dark yellow oil. LRMS: 219.1 (M+1).

Method G (1-Benzyl-4-methyl-piperidin-3-yl)-methyl-(7H-pyrrolo[2,3-d]pyrimidin-4-yl)-amine A mixture of 4-chloropyrrolo[2,3-d]pyrimidine (2.4 grams, 15.9 mmol), prepared by the method of Davoll, J. Am. Chem. Soc., (1960), 82, 131, the product from Method F (1.7 grams, 7.95 mmol) and 10 mL of triethylamine were heated in a sealed tube at 100° C. for 4 days. After cooling to room temperature and concentration under reduced pressure, the residue was purified by flash chromatography (silica; 3% methanol in dichloromethane) affording 1.0 grams (38%) of the title compound as a colorless oil. LRMS: 336.1 (M+1).

Method H

Methyl-(4-methyl-piperidin-3-yl)-(7H-pyrrolo[2,3-d]pyrimidin-4-yl)-amine

To the product from Method G (0.7 grams, 2.19 mmol) dissolved in 15 mL of ethanol was added 0.5 grams of 20% palladium hydroxide on carbon (50% water) (Aldrich) and the resulting mixture agitated (Parr-Shaker) under an atmosphere of hydrogen (50 psi) at room temperature for 2 days. The Celite filtered reaction mixture was concentrated to dryness in vacuo and the residue purified by flash chromatography (silica; 5% methanol in dichromethane) affording 0.48 grams (90%) of the title compound. LRMS: 246.1 (M+1).

Method I

[1-(4-Methoxy-benzenesulfonyl)-4-methyl-piperidin-3-yl]-methyl-(7H-pyrrolo[2,3-d]pyrimidin-4-yl)-amine To a stirred solution of 1 mL of pyridine and 9 ml of dichloromethane was added 40 mg (0.163 mmol) of the product from Method H and 20 L of 4-methoxy-benzenesulfonyl chloride and the resulting mixture stirred at room temperature for 18 hours. The reaction was then quenched upon addition of saturated $NaHCO_3$ (aq), the organic layer was removed and the aqueous layer extracted with dichloromethane.

The dichloromethane layer was dried over $Na_2SO_4$ and concentrated to dryness in vacuo. The residue was purified by PTLC (silica; 10:1 dichloromethane/methanol) affording 22 mg (32%) of the title compound as a light yellow solid. LRMS: 416.5 (M+1).

The title compounds for examples 2–297 were prepared by a method analogous to that described in Example 1.

EXAMPLE 2

[1-(4-Methoxy-benzenesulfonyl)-4-methyl-piperidin-3-yl]-methyl-(7H-pyrrolo[2,3-d]pyrimidin-4-yl)-amine

LRMS: 416.

EXAMPLE 3

(1-Benzenesulfonyl-4-methyl-piperidin-3-yl)-methyl-(7H-pyrrolo[2,3-d]pyrimidin-4-yl)-amine

LRMS: 386.

EXAMPLE 4

2-(2-{4-Methyl-3-[methyl-(7H-pyrrolo[2,3-d]pyrimidin-4-yl)-amino]-piperidine-1-sulfonyl}-ethyl)-isoindole-1,3-dione

LRMS: 483.

EXAMPLE 5

Cyclohexanecarboxylic acid (2-{4-methyl-3-[methyl-(7H-pyrrolo[2,3-d]pyrimidin-4-yl)-amino]-piperidine-1-sulfonyl}-ethyl)-amide

RMS: 463.

EXAMPLE 6

2-Chloro-N-(2-{4-methyl-3-[methyl-(7H-pyrrolo[2,3-d]pyrimidin-4-ylamino]-piperidine-1-sulfonyl}-ethyl)-benzamide

LRMS: 492.

EXAMPLE 7

4-Chloro-N-(2-{4-methyl-3-[methyl-(7H-pyrrolo[2,3-d]pyrimidin-4-yl)-amino]-piperidine-1-sulfonyl}-ethyl)-benzamide

LRMS: 492.

EXAMPLE 8

Furan-2-carboxylic acid (2-{4-methyl-3-[methyl-(7H-pyrrolo[2,3-d]pyrimidin-4-yl)-amino]-piperidine-1-sulfonyl}-ethyl)-amide

LRMS: 447.

EXAMPLE 9

3-Methoxy-N-(2-{4-methyl-3-[methyl-(7H-pyrrolo[2,3-d]pyrimidin-4-yl)-amino]-piperidine-1-sulfonyl}-ethyl)-benzamide

LRMS: 487.

EXAMPLE 10

Isoxazole-5-carboxylic acid (2-{4-methyl-3-[methyl-(7H-pyrrolo[2,3-d]pyrimidin-4-yl)-amino]-piperidine-1-sulfonyl}-ethyl)-amide

LRMS: 448.

EXAMPLE 11

2,4-Difluoro-N-(2-{4-methyl-3-[methyl-(7H-pyrrolo[2,3-d]pyrimidin-4-yl)-amino]-piperidine-1-sulfonyl}-ethyl)-benzamide

LRMS: 493.

EXAMPLE 12

3-Chloro-N-(2-{4-methyl-3-[methyl-(7H-pyrrolo[2,3-d]pyrimidin-4-yl)-amino]-piperidine-1-sulfonyl}-ethyl)-benzamide

LRMS: 492.

EXAMPLE 13

3-Fluoro-N-(2-{4-methyl-3-[methyl-(7H-pyrrolo[2,3-d]pyrimidin-4-yl)-amino]-piperidine-1-sulfonyl}-ethyl)-benzamid

LRMS: 475.

EXAMPLE 14

2-Fluoro-N-(2-{4-methyl-3-[methyl-(7H-pyrrolo[2,3-d]pyrimidin-4-yl)-amino]-piperidine-1-sulfonyl}-ethyl)-benzamide

LRMS: 475.

EXAMPLE 15

4-Fluoro-N-(2-{4-methyl-3-[methyl-(7H-pyrrolo[2,3-d]pyrimidin-4-yl)-amino]-piperidine-1-sulfonyl}-ethyl)-benzamide

LRMS: 475.

EXAMPLE 16

N-(2-{4-Methyl-3-[methyl-(7H-pyrrolo[2,3-d]pyrimidin-4-yl)-amino]-piperidine-1-sulfonyl}-ethyl)-benzamide

LRMS: 457.

EXAMPLE 17

Cyclopropanecarboxylic acid (2-{4-methyl-3-[methyl-(7H-pyrrolo[2,3-d]pyrimidin-4-yl)-amino]-piperidine-1-sulfonyl}-ethyl)-amide

LRMS: 421.

EXAMPLE 18

Cyclopentanecarboxylic acid (2-{4-methyl-3-[methyl-(7H-pyrrolo[2,3-d]pyrimidin-4-yl)-amino]-piperidine-1-sulfonyl}-ethyl)-amide

LRMS: 449.

EXAMPLE 19

Cyclopentyl-{4-methyl-3-[methyl-(7H-pyrrolo[2,3-d]pyrimidin-4-yl)-amino]-piperidin-1-yl}-methanone

LRMS: 342.

EXAMPLE 20

Tetrahydro-furan-2-carboxylic acid (2-{4-methyl-3-[methyl-(7H-pyrrolo[2,3-d]pyrimidin-4-yl)-amino]-piperidine-1-sulfonyl}-ethyl)-amide

LRMS: 451.

EXAMPLE 21

Tetrahydro-furan-3-carboxylic acid (2-{4-methyl-3-[methyl-(7H-pyrrolo[2,3-d]pyrimidin-4-yl)-amino]-piperidine-1-sulfonyl}-ethyl)-amide

LRMS: 451.

EXAMPLE 22

{4-Methyl-3-[methyl-(7H-pyrrolo[2,3-d]pyrimidin-4-yl)-amino]-piperidin-1-yl}-(tetrahydro-furan-2-yl)-methanone

LRMS: 344.

EXAMPLE 23

{4-Methyl-3-[methyl-(7H-pyrrolo[2,3-d]pyrimidin-4-yl)-amino]-piperidin-1-yl}-(tetrahydro-furan-3-yl)-methanone

LRMS: 344.

EXAMPLE 24

Cyclohexanecarboxylic acid (3-{4-methyl-3-[methyl-(7H-pyrrolo[2,3-d]pyrimidin-4-yl)-amino]-piperidin-1-yl}-3-oxo-propyl)-amide

LRMS: 427.

EXAMPLE 25

2-Cyclopropyl-1-{4-methyl-3-[methyl-(7H-pyrrolo[2,3-d]pyrimidin-4-yl)-amino]-piperidin-1-yl}-ethanone

LRMS: 328.

EXAMPLE 26

2-{4-Methyl-3-[methyl-(7H-pyrrolo[2,3-d]pyrimidin-4-yl)-amino]-piperidine-1-carbonyl}-pyrrolidine-1-carboxylic acid tert-butyl ester

LRMS: 443.

EXAMPLE 27

{4-Methyl-3-[methyl-(7H-pyrrolo[2,3-d]pyrimidin-4-yl)-amino]-piperidin-1-yl}-pyrrolidin-2-yl-methanone

LRMS: 343.

EXAMPLE 28

1-(2-{4-Methyl-3-[methyl-(7H-pyrrolo[2,3-d]pyrimidin-4-yl)-amino]-piperidine-1-carbonyl}-pyrrolidin-1-yl)-ethanone hydrochloride

LRMS: 385.

EXAMPLE 29

Furan-3-yl-{4-methyl-3-[methyl-(7H-pyrrolo[2,3-d]pyrimidin-4-yl)-amino]-piperidin-1-yl}-methanone

LRMS: 340.

EXAMPLE 30

{4-Methyl-3-[methyl-(7H-pyrrolo[2,3-d]pyrimidin-4-yl)-amino]-piperidin-1-yl}-pyridin-2-yl-methanone

LRMS: 351.

EXAMPLE 31

{4-Methyl-3-[methyl-(7H-pyrrolo[2,3-d]pyrimidin-4-yl)-amino]-piperidin-1-yl}-phenyl-methanone

LRMS: 350.

EXAMPLE 32

1-{4-Methyl-3-[methyl-(7H-pyrrolo[2,3-d]pyrimidin-4-yl)-amino]-piperidin-1-yl}-2-phenyl-ethanone

LRMS: 364.

EXAMPLE 33

2-Cyclopropyl-1-{4-methyl-3-[methyl-(7H-pyrrolo[2,3-d]pyrimidin-4-yl)-amino]-piperidin-1-yl}-ethanone hydrochloride

LRMS: 364.

EXAMPLE 34

2-{4-Methyl-3-[methyl-(7H-pyrrolo[2,3-d]pyrimidin-4-yl)-amino]-piperidine-1-carbonyl}-pyrrolidine-1-carboxylic acid tert-butyl ester

LRMS: 443.

EXAMPLE 35

4-Methyl-3-[methyl-(7H-pyrrolo[2,3-d]pyrimidin-4-yl)-amino]-piperidine-1-carboxylic acid benzylamide

LRMS: 379.

EXAMPLE 36

4-Methyl-3-[methyl-(7H-pyrrolo[2,3-d]pyrimidin-4-yl)-amino]-piperidine-1-carboxylic acid phenylamide

LRMS: 365.

EXAMPLE 37

4-Methyl-3-[methyl-(7H-pyrrolo[2,3-d]pyrimidin-4-yl)-amino]-piperidine-1-carboxylic acid tetrahydro-furan-3-yl ester

LRMS: 360.

EXAMPLE 38

1-(4-{4-Methyl-3-[methyl-(7H-pyrrolo[2,3-d]pyrimidin-4-yl)-amino]-piperidine-1-carbonyl}-piperidin-1-yl)-ethanone

LRMS: 399.

EXAMPLE 39

2-Cyclopentyl-1-{4-methyl-3-[methyl-(7H-pyrrolo[2,3-d]pyrimidin-4-yl)-amino]-piperidin-1-yl}-ethanone

LRMS: 356.

EXAMPLE 40

4-Methyl-3-[methyl-(7H-pyrrolo[2,3-d]pyrimidin-4-yl)-amino]-piperidine-1-carboxylic acid cyclohexylamide

LRMS: 371.

EXAMPLE 41

Azetidin-3-yl-{4-methyl-3-[methyl-(7H-pyrrolo[2,3-d]pyrimidin-4-yl)-amino]-piperidin-1-yl}-methanone trifluoroacetate

LRMS: 443.

EXAMPLE 42

{4-Methyl-3-[methyl-(7H-pyrrolo[2,3-d]pyrimidin-4-yl)-amino]-piperidin-1-yl}-pyrrolidin-1-yl-methanone

LRMS: 343.

EXAMPLE 43

4-Methyl-3-[methyl-(7H-pyrrolo[2,3-d]pyrimidin-4-yl)-amino]-piperidine-1-carboxylic acid methyl-phenyl-amide

LRMS: 379.

EXAMPLE 44

{4-Methyl-3-[methyl-(7H-pyrrolo[2,3-d]pyrimidin-4-yl)-amino]-piperidin-1-yl}-morpholin-4-yl-methanone

LRMS: 359.

EXAMPLE 45

Methyl-(4-methyl-3,4,5,6-tetrahydro-2H-[1,2']bipyridinyl-3-yl)-(7H-pyrrolo[2,3-d]pyrimidin-4-yl)-amine

LRMS: 323.

EXAMPLE 46

Methyl-(4-methyl-1-thiazol-2-yl-piperidin-3-yl)-(7H-pyrrolo[2,3-d]pyrimidin-4-yl)-amine

LRMS: 329.

EXAMPLE 47

4-Methyl-3-[methyl-(7H-pyrrolo[2,3-d]pyrimidin-4-yl)-amino]-piperidine-1-carboxylic acid pyridin-3-ylamide

LRMS: 366.

EXAMPLE 48

4-Methyl-3-[methyl-(7H-pyrrolo[2,3-d]pyrimidin-4-yl)-amino]-piperidine-1-carboxylic acid (4-fluoro-phenyl)-amide

LRMS: 383.

EXAMPLE 49

4-Methyl-3-[methyl-(7H-pyrrolo[2,3-d]pyrimidin-4-yl)-amino]-piperidine-1-carboxylic acid (4-nitro-phenyl)-amide

LRMS: 410.

EXAMPLE 50

4-Methyl-3-[methyl-(7H-pyrrolo[2,3-d]pyrimidin-4-yl)-amino]-piperidine-1-carboxylic acid (4-methoxy-phenyl)-amide

LRMS: 395.

EXAMPLE 51

4-({4-Methyl-3-[methyl-(7H-pyrrolo[2,3-d]pyrimidin-4-yl)-amino]-piperidine-1-carbonyl}-amino)-benzoic acid ethyl ester

LRMS: 437.

EXAMPLE 52

{4-Methyl-3-[methyl-(7H-pyrrolo[2,3-d]pyrimidin-4-yl)-amino]-piperidin-1-yl}-piperidin-1-yl-methanone

LRMS: 357.

EXAMPLE 53

Methyl-(4-methyl-5'-nitro-3,4,5,6-tetrahydro-2H-[1,2']bipyridinyl-3-yl)-(7H-pyrrolo[2,3-d]pyrimidin-4-yl)-amine

LRMS: 368.

EXAMPLE 54

4-Methyl-3-[methyl-(7H-pyrrolo[2,3-d]pyrimidin-4-yl)-amino]-piperidine-1-carboxylic acid (3-fluoro-phenyl)-amide

LRMS: 383.

EXAMPLE 55

4-Methyl-3-[methyl-(7H-pyrrolo[2,3-d]pyrimidin-4-yl)-amino]-piperidine-1-carboxylic acid (2,4-difluoro-phenyl)-amide

LRMS: 401.

EXAMPLE 56

Methyl-[4-methyl-1-(pyrrolidine-1-sulfonyl)-piperidin-3-yl]-(7H-pyrrolo[2,3-d]pyrimidin-4-yl)-amine

LRMS: 379.

EXAMPLE 57

4-Methyl-3-[methyl-(7H-pyrrolo[2,3-d]pyrimidin-4-yl)-amino]-piperidine-1-carboxylic acid (3-methoxy-phenyl)-amide

LRMS: 395.

EXAMPLE 58

4-Methyl-3-[methyl-(7H-pyrrolo[2,3-d]pyrimidin-4-yl)-amino]-piperidine-1-carboxylic acid (3-nitro-phenyl)-amide

LRMS: 410.

EXAMPLE 59

1-{4-Methyl-3-[methyl-(7H-pyrrolo[2,3-d]pyrimidin-4-yl)-amino]-piperidine-1-carbonyl}-pyrrolidine-2-carboxylic acid methyl ester

LRMS: 401.

EXAMPLE 60

Methyl-[4-methyl-1-(5-nitro-thiazol-2-yl)-piperidin-3-yl]-(7H-pyrrolo[2,3-d]pyrimidin-4-yl)-amine

LRMS: 374.

EXAMPLE 61

4-Methyl-3-[methyl-(7H-pyrrolo[2,3-d]pyrimidin-4-yl)-amino]-3,4,5,6-tetrahydro-2H-[1,2']bipyridinyl-5'-carboxylic acid methyl ester

LRMS: 381.

EXAMPLE 62

{4-Methyl-3-[methyl-(7H-pyrrolo[2,3-d]pyrimidin-4-yl)-amino]-3,4,5,6-tetrahydro-2H-[1,2']bipyridinyl-5'-yl}-methanol

LRMS: 353.

EXAMPLE 63

Methyl-[4-methyl-1-(piperidine-1-sulfonyl)-piperidin-3-yl]-(7H-pyrrolo[2,3-d]pyrimidin-4-yl)-amino

LRMS: 393.

EXAMPLE 64

4-Methyl-3-[methyl-(7H-pyrrolo[2,3-d]pyrimidin-4-yl)-amino]-piperidine-1-carboxylic acid (3-cyano-phenyl)-amide

LRMS: 390.

EXAMPLE 65

4-Methyl-3-[methyl-(7H-pyrrolo[2,3-d]pyrimidin-4-yl)-amino]-piperidine-1-carboxylic acid (3,4-difluoro-phenyl)-amide

LRMS: 401.

EXAMPLE 66

Methyl-[4-methyl-1-(morpholine-4-sulfonyl)-piperidin-3-yl]-(7H-pyrrolo[2,3-d]pyrimidin-4-yl)-amine

LRMS: 395.

EXAMPLE 67

4-Methyl-3-[methyl-(7H-pyrrolo[2,3-d]pyrimidin-4-yl)-amino]-piperidine-1-carboxylic acid (4-chloro-phenyl)-amide

LRMS: 399.

EXAMPLE 68

Methyl-[4-methyl-1-(6-methyl-pyridazin-3-yl)-piperidin-3-yl]-(7H-pyrrolo[2,3-d]pyrimidin-4-yl)-amine

LRMS: 338.

EXAMPLE 69

4-Methyl-3-[methyl-(7H-pyrrolo[2,3-d]pyrimidin 4-yl)-amino]-piperidine-1-carboxylic acid (4-cyanophenyl)-amide

LRMS: 390.

EXAMPLE 70

4-Methyl-3-[methyl-(7H-pyrrolo[2,3-d]pyrimidin-4-yl)-amino]-piperidine-1-carboxylic acid biphenyl-4-ylamide

LRMS: 441.

EXAMPLE 71

4-Methyl-3-[methyl-(7H-pyrrolo[2,3-d]pyrimidin-4-yl)-amino]-piperidine-1-carboxylic acid (4-trifluoromethyl-phenyl)-amide

LRMS: 433.

EXAMPLE 72

Methyl-(2-{4-methyl-3-[methyl-(7H-pyrrolo[2,3-d]pyrimidin-4-yl)-amino]-piperidine-1-sulfonyl}-ethyl)-carbamic acid benzyl ester

LRMS: 501.

EXAMPLE 73

Cyclopropyl-{4-methyl-3-[methyl-(7H-pyrrolo[2,3-d]pyrimidin-4-yl)-amino]-piperidin-1-yl}-methanone

LRMS: 314.

EXAMPLE 74

Cyclobutyl-{4-methyl-3-[methyl-(7H-pyrrolo[2,3-d]pyrimidin-4-yl)-amino]-piperidin-1-yl}-methanone

LRMS: 328.

EXAMPLE 75

Tetrahydro-furan-3-carboxylic acid methyl-(2-{4-methyl-3-[methyl-(7H-pyrrolo[2,3-d]pyrimidin-4-yl)-amino]-piperidine-1-sulfonyl}-ethyl)-amide

LRMS: 465.

EXAMPLE 76

Cyclohexanecarboxylic acid methyl-(2-{4-methyl-3-[methyl-(7H-pyrrolo[2,3-d]pyrimidin-4-yl)-amino]-piperidine-1-sulfonyl}-ethyl)-amide

LRMS: 477.

EXAMPLE 77

(5,7-Dichloro-1H-indol-2-yl)-{4-methyl-3-[methyl-(7H-pyrrolo[2,3-d]pyrimidin-4-yl)-amino]-piperidin-1-yl}-methanone

LRMS: 458.

EXAMPLE 78

4-({4-Methyl-3-[methyl-(7H-pyrrolo[2,3-d]pyrimidin-4-yl)-amino]-piperidine-1-carbonyl}-amino)-benzoic acid

LRMS: 409.

EXAMPLE 79

(1-Benzooxazol-2-yl-4-methyl-piperidin-3-yl)-methyl-(7H-pyrrolo[2,3-d]pyrimidin-4-yl)-amine

LRMS: 363.

EXAMPLE 80

(1H-Indol-2-yl)-{4-methyl-3-[methyl-(7H-pyrrolo[2,3-d]pyrimidin-4-yl)-amino]-piperidin-1-yl}-methanone

LRMS: 389.

EXAMPLE 81

(5-Fluoro-1H-indol-2-yl)-{4-methyl-3-[methyl-(7H-pyrrolo[2,3-d]pyrimidin-4-yl)-amino]-piperidin-1-yl}-methanone

LRMS: 407.

EXAMPLE 82

(5-Methoxy-3-methyl-benzofuran-2-yl)-{4-methyl-3-[methyl-(7H-pyrrolo[2,3-d]pyrimidin-4-yl)-amino]-piperidin-1-yl}-methanone

LRMS: 434.

EXAMPLE 83

(5-Chloro-benzofuran-2-yl)-{4-methyl-3-[methyl-(7H-pyrrolo[2,3-d]pyrimidin-4-yl)-amino]-piperidin-1-yl}-methanone

LRMS: 424.

EXAMPLE 84

{4-Methyl-3-[methyl-(7H-pyrrolo[2,3-d]pyrimidin-4-yl)-amino]-piperidin-1-yl}-(5-nitro-benzofuran-2-yl)-methanone

LRMS: 435.

EXAMPLE 85

(5-Chloro-2,3-dihydro-benzofuran-2-yl)-{4-methyl-3-[methyl-(7H-pyrrolo[2,3-d]pyrimidin-4-yl)-amino]-piperidin-1-yl}-methanone

LRMS: 426.

EXAMPLE 86

(4-Hydroxy-piperidin-1-yl)-{4-methyl-3-[methyl-(7H-pyrrolo[2,3-d]pyrimidin-4-yl)-amino]-piperidin-1-yl}-methanone

LRMS: 373.

EXAMPLE 87

1-(2-{4-Methyl-3-[methyl-(7H-pyrrolo[2,3-d]pyrimidin-4-yl)-amino]-piperidine-1-carbonyl}-benzofuran-5-yl)-ethanone

LRMS: 432.

EXAMPLE 88

1-(3-Methyl-2-{4-methyl-3-[methyl-(7H-pyrrolo[2,3-d]pyrimidin-4-yl)-amino]-piperidine-1-carbonyl}-1H-indol-5-yl)-ethanone

LRMS: 445.

EXAMPLE 89

[1-(5-Chloro-benzothiazol-2-yl)-4-methyl-piperidin-3-yl]-methyl-(7H-pyrrolo[2,3-d]pyrimidin-4-yl)-amine

LRMS: 413.

EXAMPLE 90

(3-{4-Methyl-3-[methyl-(7H-pyrrolo[2,3-d]pyrimidin-4-yl)-amino]-piperidine-1-carbonyl}-3-aza-bicyclo[3.1.0]hex-6-yl)-carbamic acid tert-butyl ester

LRMS: 470.

EXAMPLE 91

3-(4-Chloro-phenoxy)-1-{4-methyl-3-[methyl-(7H-pyrrolo[2,3-d]pyrimidin-4-yl)-amino]-piperidin-1-yl}-propan-1-one

LRMS: 428.

EXAMPLE 92

4-Methyl-3-[methyl-(7H-pyrrolo[2,3-d]pyrimidin-4-yl)-amino]-piperidine-1-carboxylic acid pyridin-2-ylamide

LRMS: 366.

EXAMPLE 93

1-{4-Methyl-3-[methyl-(7H-pyrrolo[2,3-d]pyrimidin-4-yl)-amino]-piperidine-1-carbonyl}-piperidine-4-carboxylic acid amide hydrochloride

LRMS: 436.

EXAMPLE 94

4-Methyl-3-[methyl-(7H-pyrrolo[2,3-d]pyrimidin-4-yl)-amino]-piperidine-1-carboxylic acid (5-chloro-pyridin-2-yl)-amide

LRMS: 400.

EXAMPLE 95

3-{4-Methyl-3-[methyl-(7H-pyrrolo[2,3-d]pyrimidin-4-yl)-amino]-piperidine-1-carbonyl}-cyclopentanone

LRMS: 356.

EXAMPLE 96

(3-Hydroxy-cyclopentyl)-{4-methyl-3-[methyl-(7H-pyrrolo[2,3-d]pyrimidin-4-yl)-amino]-piperidin-1-yl}-methanone

LRMS: 358.

EXAMPLE 97

4-{4-Methyl-3-[methyl-(7H-pyrrolo[2,3-d]pyrimidin-4-yl)-amino]-piperidine-1-carbonyl}-cyclohexanone

LRMS: 370.

EXAMPLE 98

3-{4-Methyl-3-[methyl-(7H-pyrrolo[2,3-d]pyrimidin-4-yl)-amino]-piperidine-1-carbonyl}-cyclohexanone

LRMS: 370.

EXAMPLE 99

4-Methyl-3-[methyl-(7H-pyrrolo[2,3-d]pyrimidin-4-yl)-amino]-piperidine-1-carboxylic acid (5-nitro-pyridin-2-yl)-amide

LRMS: 413.

EXAMPLE 100

[4-({4-Methyl-3-[methyl-(7H-pyrrolo[2,3-d]pyrimidin-4-yl)-amino]-piperidine-1-carbonyl}-amino)-phenyl]-acetic acid

LRMS: 423.

EXAMPLE 101

(4-Amino-piperidin-1-yl)-{4-methyl-3-[methyl-(7H-pyrrolo[2,3-d]pyrimidin-4-yl)-amino]-piperidin-1-yl}-methanone hydrochloride

LRMS: 408.

EXAMPLE 102

4-Methyl-3-[methyl-(7H-pyrrolo[2,3-d]pyrimidin-4-yl)-amino]-piperidine-1-carboxylic acid (6-methyl-pyridin-2-yl)-amide

LRMS: 380.

EXAMPLE 103

1-Methyl-4-{4-methyl-3-[methyl-(7H-pyrrolo[2,3-d]pyrimidin-4-yl)-amino]-piperidine-1-carbonyl}-pyrrolidin-2-one

LRMS: 371.

EXAMPLE 104

1-Benzyl-3-{4-methyl-3-[methyl-(7H-pyrrolo[2,3-d]pyrimidin-4-yl)-amino]-piperidine-1-carbonyl}-pyrrolidin-2-one

LRMS: 447.

EXAMPLE 105

4-Methyl-3-[methyl-(7H-pyrrolo[2,3-d]pyrimidin-4-yl)-amino]-piperidine-1-carboxylic acid (5-trifluoromethyl-pyridin-2-yl)-amide

LRMS: 434.

EXAMPLE 106

4-Methyl-3-[methyl-(7H-pyrrolo[2,3-d]pyrimidin-4-yl)-amino]-cyclohexanecarboxylic acid (4-cyano-phenyl)-amide

LRMS: 389.

EXAMPLE 107

4-Methyl-3-[methyl-(7H-pyrrolo[2,3-d]pyrimidin-4-yl)-amino]-piperidine-1-carboxylic acid (4-carbamoyl-phenyl)-amide

LRMS: 408.

EXAMPLE 108

4-Methyl-3-[methyl-(7H-pyrrolo[2,3-d]pyrimidin-4-yl)-amino]-piperidine-1-carboxylic acid (4-sulfamoyl-phenyl)-amide

LRMS: 444.

EXAMPLE 109

4-Methyl-3-[methyl-(7H-pyrrolo[2,3-d]pyrimidin-4-yl)-amino]-piperidine-1-carboxylic acid (5-methyl-thiazol-2-yl)-amide

LRMS: 386.

EXAMPLE 110

4-Methyl-3-[methyl-(7H-pyrrolo[2,3-d]pyrimidin-4-yl)-amino]-piperidine-1-carboxylic acid (5,6-dichloro-benzothiazol-2-yl)-amide

LRMS: 491.

EXAMPLE 111

4-Methyl-3-[methyl-(7H-pyrrolo[2,3-d]pyrimidin-4-yl)-amino]-piperidine-1-carboxylic acid (4-methyl-thiazol-2-yl)-amide

LRMS: 386.

EXAMPLE 112

Azetidin-1-yl-{4-methyl-3-[methyl-(7H-pyrrolo[2,3-d]pyrimidin-4-yl)-amino]-piperidin-1-yl}-methanone hydrochloride

LRMS: 365.

EXAMPLE 113

[2-({4-Methyl-3-[methyl-(7H-pyrrolo[2,3-d]pyrimidin-4-yl)-amino]-piperidine-1-carbonyl}-amino)-thiazol-4-yl]-acetic acid ethyl ester

LRMS: 458.

EXAMPLE 114

4-Methyl-3-[methyl-(7H-pyrrolo[2,3-d]pyrimidin-4-yl)-amino]-piperidine-1-carboxylic acid (4,5-dimethyl-thiazol-2-yl)-amide

LRMS: 400.

EXAMPLE 115

[2-({4-Methyl-3-[methyl-(7H-pyrrolo[2,3-d]pyrimidin-4-yl)-amino]-piperidine-1-carbonyl}-amino)-thiazol-4-yl]-acetic acid

LRMS: 430.

EXAMPLE 116

4-Methyl-3-[methyl-(7H-pyrrolo[2,3-d]pyrimidin-4-yl)-amino]-piperidine-1-carboxylic acid benzothiazol-2-ylamide

LRMS: 422.

EXAMPLE 117

4-Methyl-3-[methyl-(7H-pyrrolo[2,3-d]pyrimidin-4-yl)-amino]-piperidine-1-carboxylic acid thiazol-2-ylamide

LRMS: 372.

EXAMPLE 118

4-Methyl-3-[methyl-(7H-pyrrolo[2,3-d]pyrimidin-4-yl)-amino]-piperidine-1-carboxylic acid [6-(2-dimethylamino-ethylamino)-pyridin-3-yl]-amide

LRMS: 452.

EXAMPLE 119

N-(4-Chloro-phenyl)-2-{4-methyl-3-[methyl-(7H-pyrrolo[2,3-d]pyrimidin-4-yl)-amino]-piperidin-1-yl}-acetamide

LRMS: 413.

EXAMPLE 120

N,N-Dimethyl-2-{4-methyl-3-[methyl-(7H-pyrrolo[2,3-d]pyrimidin-4-yl)-amino]-piperidin-1-yl}-acetamide

LRMS: 331.

EXAMPLE 121

4-Methyl-3-[methyl-(7H-pyrrolo[2,3-d]pyrimidin-4-yl)-amino]-piperidine-1-carboxylic acid [6-(2-pyrrolidin-1-yl-ethylamino)-pyridin-3-yl]-amide

LRMS: 478.

EXAMPLE 122

{2-[5-({4-Methyl-3-[methyl-(7H-pyrrolo[2,3-d]pyrimidin-4-yl)-amino]-piperidine-1-carbonyl}-amino)-pyridin-2-yloxy]-ethyl}-carbamic acid tert-butyl ester

LRMS: 525.

EXAMPLE 123

4-Methyl-3-[methyl-(7H-pyrrolo[2,3-d]pyrimidin-4-yl)-amino]-piperidine-1-carboxylic acid [6-(2-amino-ethoxy)-pyridin-3-yl]-amide

LRMS: 425.

EXAMPLE 124

4-Methyl-3-[methyl-(7H-pyrrolo[2,3-d]pyrimidin-4-yl)-amino]-piperidine-1-carboxylic acid (4-methyl-sulfamoyl-phenyl)-amide

LRMS: 458.

EXAMPLE 125

4-Methyl-3-[methyl-(7H-pyrrolo[2,3-d]pyrimidin-4-yl)-amino]-piperidine-1-carboxylic acid (4-methane-sulfonyl-phenyl)-amide

LRMS: 443.

EXAMPLE 126

4-Methyl-3-[methyl-(7H-pyrrolo[2,3-d]pyrimidin-4-yl)-amino]-piperidine-1-carboxylic acid (5-methyl-[1,3,4]thiadiazol-2-yl)-amide

LRMS: 387.

EXAMPLE 127

4-Methyl-3-[methyl-(7H-pyrrolo[2,3-d]pyrimidin-4-yl)-amino]-piperidine-1-carboxylic acid (4-methyl-sulfamoyl-phenyl)-amide hydrochloride

LRMS: 495.

EXAMPLE 128

Methyl-[4-methyl-1-(1-phenyl-ethyl)-piperidin-3-yl]-(7H-pyrrolo[2,3-d]pyrimidin-4-yl)-amine

LRMS: 350.

EXAMPLE 129

(3-Hydroxy-pyrrolidin-1-yl)-{4-methyl-3-[methyl-(7H-pyrrolo[2,3-d]pyrimidin-4-yl)-amino]-piperidin-1-yl}-methanone

LRMS: 359.

EXAMPLE 130

4-Methyl-3-[methyl-(7H-pyrrolo[2,3-d]pyrimidin-4-yl)-amino]-piperidine-1-carboxylic acid tert-butyl ester

LRMS: 346.

EXAMPLE 131

4-Methyl-3-[methyl-(7H-pyrrolo[2,3-d]pyrimidin-4-yl)-amino]-piperidine-1-carboxylic acid [4-(2-dimethylamino-ethyl)-thiazol-2-yl]-amide

LRMS: 443.

EXAMPLE 132

4-Methyl-3-[methyl-(7H-pyrrolo[2,3-d]pyrimidin-4-yl)-amino]-piperidine-1-carboxylic acid 4-methane-sulfonyl-benzylamide

LRMS: 457.

EXAMPLE 133

4-Methyl-3-[methyl-(7H-pyrrolo[2,3-d]pyrimidin-4-yl)-amino]-piperidine-1-carboxylic acid (4-acetyl-sulfamoyl-phenyl)-amide

LRMS: 486.

EXAMPLE 134

1-{4-Methyl-3-[methyl-(7H-pyrrolo[2,3-d]pyrimidin-4-yl)-amino]-piperidin-1-yl}-2-phenyl-ethane-1,2-dione

LRMS: 378.

EXAMPLE 135

Methyl-[4-methyl-1-(6-methylamino-pyrimidin-4-yl)-piperidin-3-yl]-(7H-pyrrolo[2,3-d]pyrimidin-4-yl)-amine

LRMS: 353.

EXAMPLE 136

Methyl-[4-methyl-1-(6-pyrrolidin-1-yl-pyrimidin-4-yl)-piperidin-3-yl]-(7H-pyrrolo[2,3-d]pyrimidin-4-yl)-amine

LRMS: 393.

EXAMPLE 137

[1-(6-Benzylamino-pyrimidin-4-yl)-4-methyl-piperidin-3-yl]-methyl-(7H-pyrrolo[2,3-d]pyrimidin-4-yl)-amine

LRMS: 429.

EXAMPLE 138

N,N-Dimethyl-N'-(6-{4-methyl-3-[methyl-(7H-pyrrolo[2,3-d]pyrimidin-4-yl)-amino]-piperidin-1-yl}-pyrimidin-4-yl)-ethane-1,2-diamine

LRMS: 410.

EXAMPLE 139

[1-(6-Chloro-pyrimidin-4-yl)-4-methyl-piperidin-3-yl]-methyl-(7H-pyrrolo[2,3-d]pyrimidin-4-yl)-amine

LRMS: 358.

EXAMPLE 140

[1-(2-Fluoro-benzyl)-4-methyl-piperidin-3-yl]-methyl-(7H-pyrrolo[2,3-d]pyrimidin-4-yl)-amine

LRMS: 354

EXAMPLE 141

[1-(2-Chloro-pyrimidin-4-yl)-4-methyl-piperidin-3-yl]-methyl-(7H-pyrrolo[2,3-d]pyrimidin-4-yl)-amine

LRMS: 359.

EXAMPLE 142

[1-(4-Chloro-pyrimidin-2-yl)-4-methyl-piperidin-3-yl]-methyl-(7H-pyrrolo[2,3-d]pyrimidin-4-yl)-amine

LRMS: 359.

EXAMPLE 143

Methyl-[4-methyl-1-(2-methylamino-pyrimidin-4-yl)-piperidin-3-yl]-(7H-pyrrolo[2,3-d]pyrimidin-4-yl)-amine

LRMS: 353.

EXAMPLE 144

Methyl-[4-methyl-1-(4-pyrrolidin-1-yl-pyrimidin-2-yl)-piperidin-3-yl]-(7H-pyrrolo[2,3-d]pyrimidin-4-yl)-amine

LRMS: 353.

EXAMPLE 145

4-Methyl-3-[methyl-(7H-pyrrolo[2,3-d]pyrimidin-4-yl)-amino]-piperidine-1-carboxylic acid (3-methyl-isoxazol-5-yl)-amide

LRMS: 370.

EXAMPLE 146

4-Methyl-3-[methyl-(7H-pyrrolo[2,3-d]pyrimidin-4-yl)-amino]-piperidine-1-carboxylic acid (3-methyl-isoxazol-4-yl)-amide

LRMS: 370.

XAMPLE 147

4-Methyl-3-[methyl-(7H-pyrrolo[2,3-d]pyrimidin-4-yl)-amino]-piperidine-1-carboxylic acid (5-methyl-isoxazol-3-yl)-amide

LRMS: 370.

EXAMPLE 148

4-Methyl-3-[methyl-(7H-pyrrolo[2,3-d]pyrimidin-4-yl)-amino]-piperidine-1-carboxylic acid (5-tert-butyl-isoxazol-3-yl)-amide

LRMS: 412.

EXAMPLE 149

4-Methyl-3-[methyl-(7H-pyrrolo[2,3-d]pyrimidin-4-yl)-amino]-piperidine-1-carboxylic acid isoxazol-3-ylamide

LRMS: 356.

EXAMPLE 150

N-Methyl-3-{4-methyl-3-[methyl-(7H-pyrrolo[2,3-d]pyrimidin-4-yl)-amino]-piperidin-1-yl}-propionamide

LRMS: 331.

EXAMPLE 151

1-{4-Methyl-3-[methyl-(7H-pyrrolo[2,3-d]pyrimidin-4-yl)-amino]-piperidin-1-yl}-propan-2-one

LRMS: 302.

EXAMPLE 152

{4-Methyl-3-[methyl-(7H-pyrrolo[2,3-d]pyrimidin-4-yl)-amino]-piperidin-yl}-oxo-acetic acid methyl ester

LRMS: 332.

EXAMPLE 153

(1-Cyclohexylmethyl-4-methyl-piperidin-3-yl)-methyl-(7H-pyrrolo[2,3-d]pyrimidin-4-yl)-amine

LRMS: 342.

EXAMPLE 154

[1-(5-Amino-thiazol-2-yl)-4-methyl-piperidin-3-yl]-methyl-(7H-pyrrolo[2,3-d]pyrimidin-4-yl)-amine

LRMS: 344.

EXAMPLE 155

Methyl-(4-methyl-piperidin-3-yl)-(7H-pyrrolo[2,3-d]pyrimidin-4-yl)-amine

LRMS: 246.

EXAMPLE 156

3-{4-Methyl-3-[methyl-(7H-pyrrolo[2,3-d]pyrimidin-4-yl)-amino]-piperidin-1-yl}-3-oxo-propionic acid methyl ester

LRMS: 346.

EXAMPLE 157

(1-Benzenesulfonylmethyl-4-methyl-piperidin-3-yl)-methyl-(7H-pyrrolo[2,3-d]pyrimidin-4-yl)-amine

LRMS: 400.

EXAMPLE 158

(3-Hydroxy-pyrrolidin-1-yl)-{4-methyl-3-[methyl-(7H-pyrrolo[2,3-d]pyrimidin-4-yl)-amino]-piperidin-1-yl}-methanone

LRMS: 359.

EXAMPLE 159

1-{4-Methyl-3-[methyl-(7H-pyrrolo[2,3-d]pyrimidin-4-yl)-amino]-piperidin-1-yl}-propane-1,2-dione

LRMS: 316.

EXAMPLE 160

4-Methyl-3-[methyl-(7H-pyrrolo[2,3-d]pyrimidin-4-yl)-amino]-piperidine-1-carboxylic acid (6-sulfamoyl-pyridin-3-yl)-amide

LRMS: 445.

EXAMPLE 161

4-Methyl-3-[methyl-(7H-pyrrolo[2,3-d]pyrimidin-4-yl)-amino]-piperidine-1-carboxylic acid (6-acetylamino-pyridin-3-yl)-amide

LRMS: 423.

EXAMPLE 162

4-Methyl-3-[methyl-(7H-pyrrolo[2,3-d]pyrimidin-4-yl)-amino]-piperidine-1-carboxylic acid [4-(2-dimethylamino-ethylsulfamoyl)-phenyl]-amide

LRMS: 515.

EXAMPLE 163

4-Methyl-3-[methyl-(7H-pyrrolo[2,3-d]pyrimidin-4-yl)-amino]-piperidine-1-carboxylic acid (6-cyano-pyridin-3-yl)-amide

LRMS: 391.

EXAMPLE 164

4-Methyl-3-[methyl-(7H-pyrrolo[2,3-d]pyrimidin-4-yl)-amino]-3,4,5,6-tetrahydro-2H-[1,2']bipyridinyl-5'-sulfonic acid pyridin-2-ylamide

LRMS: 479.

EXAMPLE 165

4-Methyl-3-[methyl-(7H-pyrrolo[2,3-d]pyrimidin-4-yl)-amino]-piperidine-1-carboxylic acid [6-(pyrrolidine-1-carbonyl)-pyridin-3-yl]-amide

LRMS: 463.

EXAMPLE 166

2-Imidazol-1-yl-1-{4-methyl-3-[methyl-(7H-pyrrolo[2,3-d]pyrimidin-4-yl)-amino]-piperidin-1-yl}-ethanone

LRMS: 354.

EXAMPLE 167

4-Methyl-3-[methyl-(7H-pyrrolo[2,3-d]pyrimidin-4-yl)-amino]-3,4,5,6-tetrahydro-2H-[1,2']bipyridinyl-5'-carboxylic acid methylamide

LRMS: 380.

EXAMPLE 168

{4-Methyl-3-[methyl-(7H-pyrrolo[2,3-d]pyrimidin-4-yl)-amino]-3,4,5,6-tetrahydro-2H-r[1,2']bipyridinyl-5'-yl}-morpholin-4-yl-methanone

LRMS: 436.

EXAMPLE 169

5-({4-Methyl-3-[methyl-(7H-pyrrolo[2,3-d]pyrimidin-4-yl)-amino]-piperidine-1-carbonyl}-amino)-pyridine-2-carboxylic acid propylamide

LRMS: 451.

EXAMPLE 170

4-Methyl-3-[methyl-(7H-pyrrolo[2,3-d]pyrimidin-4-yl)-amino]-3,4,5,6-tetrahydro-2H-[1,2']bipyridinyl-5'-carboxylic acid amide

LRMS: 366.

EXAMPLE 171

4-Methyl-3-[methyl-(7H-pyrrolo[2,3-d]pyrimidin-4-yl)-amino]-3,4,5,6-tetrahydro-2H-[1,2']bipyridinyl-5'-carbonitrile

LRMS: 348.

EXAMPLE 172

4-Methyl-3-[methyl-(7H-pyrrolo[2,3-d]pyrimidin-4-yl)-amino]-piperidine-1-carboxylic acid [4-(pyrrolidine-1-sulfonyl)-phenyl]-amide

LRMS: 498.

EXAMPLE 173

4-Methyl-3-[methyl-(7H pyrrolo[2,3-d]pyrimidin-4-yl)-amino]-piperidine-1-carboxylic acid [4-(morpholine-4-sulfonyl)-phenyl]-amide

LRMS: 514.

EXAMPLE 174

(3-Hydroxy-pyrrolidin-1-yl)-{4-methyl-3-[methyl-(7H-pyrrolo[2,3-d]pyrimidin-4-yl)-amino]-piperidin-1-yl}-methanone

LRMS: 359.

EXAMPLE 175

4-Methyl-3-[methyl-(7H-pyrrolo[2,3-d]pyrimidin-4-yl)-amino]-piperidine-1-carboxylic acid [6-(morpholine-4-carbonyl)-pyridin-3-yl]-amide

LRMS: 479.

EXAMPLE 176

4-Methyl-3-[methyl-(7H-pyrrolo[2,3-d]pyrimidin-4-yl)-amino]-piperidine-1-carboxylic acid [6-(morpholine-4-carbonyl)-pyridin-3-yl]-amide

LRMS: 479.

EXAMPLE 177

2-Imidazol-1-yl-1-{4-methyl-3-[methyl-(7H-pyrrolo[2,3-d]pyrimidin-4-yl)-amino]-piperidin-1-yl}-ethanone

LRMS: 354.

EXAMPLE 178

4-Methyl-3-[methyl-(7H-Pyrrolo[2,3-d]pyrimidin-4-yl)-amino]-piperidine-1-carboxylic acid isoxazol-3-ylamide

LRMS: 356.

EXAMPLE 179

4-Methyl-3-[methyl-(7H-pyrrolo[2,3-d]pyrimidin-4-yl)-amino]-piperidine-1-carboxylic acid (2,5-dimethyl-2H-pyrazol-3-yl)-amide

LRMS: 383.

EXAMPLE 180

4-Methyl-3-[methyl-(7H-pyrrolo[2,3-d]pyrimidin-4-yl)-amino]-piperidine-1-carboxylic acid (5-cyclopropyl-2-methyl-2H-pyrazol-3-yl)-amide

LRMS: 409.

EXAMPLE 181

4-Methyl-3-[methyl-(7H-pyrrolo[2,3-d]pyrimidin-4-yl)-amino]-piperidine-1-carboxylic acid (3-methyl-isothiazol-5-yl)-amide

LRMS: 386.

EXAMPLE 182

4-{4-Methyl-3-[methyl-(7H-pyrrolo[2,3-d]pyrimidin-4-yl)-amino]-piperidin-1-ylmethyl}-benzoic acid

LRMS: 380.

EXAMPLE 183

Methyl-[4-methyl-5'-(pyrrolidine-1-sulfonyl)-3,4,5,6-tetrahydro-2H-[1,2']bipyridinyl-3-yl]-(7H-pyrrolo[2,3-d]pyrimidin-4-yl)-amine

LRMS: 456.

EXAMPLE 184

4-Methyl-3-[methyl-(7H-pyrrolo[2,3-d]pyrimidin-4-yl)-amino]-3,4,5,6-tetrahydro-2H-[1,2']bipyridinyl-5'-sulfonic acid methylamide

LRMS: 416.

EXAMPLE 185

4-{4-Methyl-3-[methyl-(7H-pyrrolo[2,3-d]pyrimidin-4-yl)-amino]-piperidin-1-ylmethyl}-benzenesulfonamide

LRMS: 415.

EXAMPLE 186

N-tert-Butyl-4-{4-methyl-3-[methyl-(7H-pyrrolo[2,3-d]pyrimidin-4-yl)-amino]-piperidin-1-ylmethyl}-benzenesulfonamide

LRMS: 472.

EXAMPLE 187

1-{4-Methyl-3-[methyl-(7H-pyrrolo[2,3-d]pyrimidin-4-yl)-amino]-piperidin-1-yl}-2-pyrazol-1-yl-ethanone

LRMS: 354.

EXAMPLE 188

Methyl-[4-methyl-1-(5-nitro-benzooxazol-2-yl)-piperidin-3-yl]-(7H-pyrrolo[2,3-d]pyrimidin-4-yl)-amine

LRMS: 408.

EXAMPLE 189

4-Methyl-3-[methyl-(7H-pyrrolo[2,3-d]pyrimidin-4-yl)-amino]-3,4,5,6-tetrahydro-2H-[1,2']bipyridinyl-5'-sulfonic acid (2-hydroxy-ethyl)-amide

LRMS: 446.

EXAMPLE 190

N-tert-Butyl-4-{4-methyl-3-[methyl-(7H-pyrrolo[2,3-d]pyrimidin-4-yl)-amino]-piperidin-1-ylmethyl}-benzenesulfonamide

LRMS: 471.

EXAMPLE 191

N-Methyl-2-{4-methyl-3-[methyl-(7H-pyrrolo[2,3-d]pyrimidin-4-yl)-amino]-piperidin-1-yl}-2-oxo-acetamide

LRMS: 331.

EXAMPLE 192

[1-(5-Ethanesulfonyl-benzooxazol-2-yl)-4-methyl-piperidin-3-yl]-methyl-(7H-pyrrolo[2,3-d]pyrimidin-4-yl)-amine

LRMS: 455.

EXAMPLE 193

Methyl-[4-methyl-1-(5-methyl-benzooxazol-2-yl)-piperidin-3-yl]-(7H-pyrrolo[2,3-d]pyrimidin-4-yl)-amine

LRMS: 377.

EXAMPLE 194

4-Methyl-3-[methyl-(7H-pyrrolo[2,3-d]pyrimidin-4-yl)-amino]-piperidine-1-carboxylic acid (6-chloro-pyridin-3-yl)-amide

LRMS: 400.

EXAMPLE 195

Methyl-(4-methyl-1-quinolin-2-yl-piperidin-3-yl)-(7H-pyrrolo[2,3-d]pyrimidin-4-yl)-amine

LRMS: 373.

EXAMPLE 196

4-Methyl-3-[methyl-(7H-pyrrolo[2,3-d]pyrimidin-4-yl)-amino]-3,4,5,6-tetrahydro-2H-[1,2']bipyridinyl-5'-sulfonic acid amide

LRMS: 402.

EXAMPLE 197

1-{4-Methyl-3-[methyl-(7H-pyrrolo[2,3-d]pyrimidin-4-yl)-amino]-piperidin-1-yl}-2-pyrrolidin-1-yl-ethane-1,2-dione

LRMS: 371.

EXAMPLE 198

Methyl-[4-methyl-1-(4-methyl-benzooxazol-2-yl)-piperidin-3-yl]-(7H-pyrrolo[2,3-d]pyrimidin-4-yl)-amine

LRMS: 377.

EXAMPLE 199

1-{4-Methyl-3-[methyl-(7H-pyrrolo[2,3-d]pyrimidin-4-yl)-amino]-piperidin-1-yl}-2-morpholin-4-yl-ethane-1,2-dione

LRMS: 387.

EXAMPLE 200

4-Methyl-3-[methyl-(7H-pyrrolo[2,3-d]pyrimidin-4-yl)-amino]-piperidine-1-carboxylic acid (6-methanesulfonyl-pyridin-3-yl)-amide

LRMS: 444.

EXAMPLE 201

4-Methyl-3-[methyl-(7H-pyrrolo[2,3-d]pyrimidin-4-yl)-amino]-piperidine-1-carboxylic acid (6-methanesulfonyl-pyridin-3-yl)-amide

LRMS: 444.

EXAMPLE 202

Methyl-[4-methyl-1-(6-nitro-benzooxazol-2-yl)-piperidin-3-yl]-(7H-pyrrolo[2,3-d]pyrimidin-4-yl)-amine

LRMS: 408.

EXAMPLE 203

4-Methyl-3-[methyl-(7H-pyrrolo[2,3-d]pyrimidin-4-yl)-amino]-piperidine-1-carboxylic acid (6-methanesulfonyl-pyridin-3-yl)-amide

LRMS: 444.

EXAMPLE 204

4-Methyl-3-[methyl-(7H-pyrrolo[2,3-d]pyrimidin-4-yl)-amino]-piperidine-1-carboxylic acid (6-methanesulfonyl-pyridin-3-yl)-amide

LRMS: 444.

EXAMPLE 205

Methyl-[4-methyl-1-(6-nitro-benzooxazol-2-yl)-piperidin-3-yl]-(7H-pyrrolo[2,3-d]pyrimidin-4-yl)-amine

LRMS: 408.

EXAMPLE 206

Methyl-[4-methyl-1-(toluene-3-sulfonyl)-piperidin-3-yl]-(7H-pyrrolo[2,3-d]pyrimidin-4-yl)-amine

LRMS: 400.

EXAMPLE 207

Methyl-[4-methyl-1-(4-trifluoromethyl-benzenesulfonyl)-piperidin-3-yl]-(7H-pyrrolo[2,3-d]pyrimidin-4-yl)-amine

LRMS: 454.

EXAMPLE 208

(1-Benzothiazol-2-yl-4-methyl-piperidin-3-yl)-methyl-(7H-pyrrolo[2,3-d]pyrimidin-4-yl)-amine

LRMS: 379.

EXAMPLE 209

[1-(5,7-Dimethyl-benzooxazol-2-yl)-4-methyl-piperidin-3-yl]-methyl-(7H-pyrrolo[2,3-d]pyrimidin-4-yl)-amine

LRMS: 391.

EXAMPLE 210

2-{4-Methyl-3-[methyl-(7H-pyrrolo[2,3-d]pyrimidin-4-yl)-amino]-piperidin-1-yl}-benzooxazole-6-carboxylic acid methyl ester

LRMS: 421.

EXAMPLE 211

Methyl-[4-methyl-1-(6-methyl-benzooxazol-2-yl)-piperidin-3-yl]-(7H-pyrrolo[2,3-d]pyrimidin-4-yl)-amine

LRMS: 377.

EXAMPLE 212

[1-(6-Methoxy-benzooxazol-2-yl)-4-methyl-piperidin-3-yl]-methyl-(7H-pyrrolo[2,3-d]pyrimidin-4-yl)-amine

LRMS: 393.

EXAMPLE 213

Methyl-[4-methyl-1-(5-trifluoromethyl-benzothiazol-2-yl)-piperidin-3-yl]-(7H-pyrrolo[2,3-d]pyrimidin-4-yl)-amine

LRMS: 447.

EXAMPLE 214

[1-(5,7-Dichloro-benzooxazol-2-yl)-4-methyl-piperidin-3-yl]-methyl-(7H-pyrrolo[2,3-d]pyrimidin-4-yl)-amine

LRMS: 432.

EXAMPLE 215

[1-(6-Chloro-pyridine-3-sulfonyl)-4-methyl-piperidin-3-yl]-methyl-(7H-pyrrolo[2,3-d]pyrimidin-4-yl)-amine

LRMS: 422.

EXAMPLE 216

[1-(4-Chloro-benzenesulfonyl)-4-methyl-piperidin-3-yl]-methyl-(7H-pyrrolo[2,3-d]pyrimidin-4-yl)-amine

LRMS: 421.

EXAMPLE 217

[1-(4-Fluoro-benzenesulfonyl)-4-methyl-piperidin-3-yl-methyl-(7H-pyrrolo[2,3-d]pyrimidin-4-yl)-amine

LRMS: 404.

EXAMPLE 218

4-{4-Methyl-3-[methyl-(7H-pyrrolo[2,3-d]pyrimidin-4-yl)-amino]-piperidine-1-sulfonyl}-benzonitrile

LRMS: 411.

EXAMPLE 219

4-{4-Methyl-3-[methyl-(7H-pyrrolo[2,3-d]pyrimidin-4-yl)-amino]-piperidine-1-sulfonyl}-benzenesulfonyl fluoride

LRMS: 468.

EXAMPLE 220

2-{4-Methyl-3-[methyl-(7H-pyrrolo[2,3-d]pyrimidin-4-yl)-amino]-piperidine-1-sulfonyl}-benzonitrile

LRMS: 411.

EXAMPLE 221

1-{4-Methyl-3-[methyl-(7H-pyrrolo[2,3-d]pyrimidin-4-yl)-amino]-piperidin-1-yl}-2-tetrazol-1-yl-ethanone

LRMS: 356.

EXAMPLE 222

Methyl-[4-methyl-1-(2,2,2-trifluoro-ethanesulfonyl)-piperidin-3-yl]-(7H-pyrrolo[2,3-d]pyrimidin-4-yl)-amine

LRMS: 392.

EXAMPLE 223

[1-(2,6-Difluoro-benzenesulfonyl)-4-methyl-piperidin-3-yl]-methyl-(7H-pyrrolo[2,3-d]pyrimidin-4-yl)-amine

LRMS: 422.

EXAMPLE 224

[1-(4-tert-Butyl-benzenesulfonyl)-4-methyl-piperidin-3-yl]-methyl-(7H-pyrrolo[2,3-d]pyrimidin-4-yl)-amine

LRMS: 442.

EXAMPLE 225

[1-(2,4-Difluoro-benzenesulfonyl)-4-methyl-piperidin-3-yl]-methyl-(7H-pyrrolo[2,3-d]pyrimidin-4-yl)-amine

LRMS: 422.

EXAMPLE 226

Methyl-[4-methyl-1-(2-trifluoromethyl-benzenesulfonyl)-piperidin-3-yl]-(7H-pyrrolo[2,3-d]pyrimidin-4-yl)-amine

LRMS: 454.

EXAMPLE 227

[1-(3,5-Bis-trifluoromethyl-benzenesulfonyl)-4-methyl-piperidin-3-yl]-methyl-(7H-pyrrolo[2,3-d]pyrimidin-4-yl)-amine

LRMS: 522.

EXAMPLE 228

[1-(3,5-Dichloro-benzenesulfonyl)-4-methyl-piperidin-3-yl]-methyl-(7H-pyrrolo[2,3-d]pyrimidin-4-yl)-amine

LRMS: 455.

EXAMPLE 229

4-{4-Methyl-3-[methyl-(7H-pyrrolo[2,3-d]pyrimidin-4-yl)-amino]-piperidine-1-sulfonyl}-benzoic acid

LRMS: 431.

EXAMPLE 230

[1-(6-Chloro-pyridine-3-sulfonyl)-4-methyl-piperidin-3-yl]-methyl-(7H-pyrrolo[2,3-d]pyrimidin-4-yl)-amine

LRMS: 422.

EXAMPLE 231

[1-(4-Chloro-benzenesulfonyl)-4-methyl-piperidin-3-yl]-methyl-(7H-pyrrolo[2,3-d]pyrimidin-4-yl)-amine

LRMS: 421.

EXAMPLE 232

[1-(4-Fluoro-benzenesulfonyl)-4-methyl-piperidin-3-yl]-methyl-(7H-pyrrolo[2,3-d]pyrimidin-4-yl)-amine

LRMS: 404.

EXAMPLE 233

4-{4-Methyl-3-[methyl-(7H-pyrrolo[2,3-d]pyrimidin-4-yl)-amino]-piperidine-1-sulfonyl}-benzonitrile

LRMS: 411.

EXAMPLE 234

4-{4-Methyl-3-[methyl-(7H-pyrrolo[2,3-d]pyrimidin-4-yl)-amino]-piperidine-1-sulfonyl}-benzenesulfonyl fluoride

LRMS: 468.

EXAMPLE 235

2-{4-Methyl-3-[methyl-(7H-pyrrolo[2,3-d]pyrimidin-4-yl)-amino]-piperidine-1-sulfonyl}-benzonitrile

LRMS: 411.

EXAMPLE 236

1-{4-Methyl-3-[methyl-(7H-pyrrolo[2,3-d]pyrimidin-4-yl)-amino]-piperidin-1-yl}-2-tetrazol-1-yl-ethanone

LRMS: 356.

EXAMPLE 237

Methyl-[4-methyl-1-(2,2,2-trifluoro-ethanesulfonyl)-piperidin-3-yl]-(7H-pyrrolo[2,3-d]pyrimidin-4-yl)-amine

LRMS: 392.

EXAMPLE 238

[1-(2,6-Difluoro-benzenesulfonyl)-4-methyl-piperidin-3-yl]-methyl-(7H-pyrrolo[2,3-d]pyrimidin-4-yl)-amine

LRMS: 422.

EXAMPLE 239

[1-(4-tert-Butyl-benzenesulfonyl)-4-methyl-piperidin-3-yl]-methyl-(7H-pyrrolo[2,3-d]pyrimidin-4-yl)-amine

LRMS: 442.

EXAMPLE 240

[1-(2,4-Difluoro-benzenesulfonyl)-4-methyl-piperidin-3-yl]-methyl-(7H-pyrrolo[2,3-d]pyrimidin-4-yl)-amine

LRMS: 422.

EXAMPLE 241

Methyl-[4-methyl-1-(2-trifluoromethyl-benzenesulfonyl)-piperidin-3-yl]-(7H-pyrrolo[2,3-d]pyrimidin-4-yl)-amine

LRMS: 454.

EXAMPLE 242

[1-(3,5-Bis-trifluoromethyl-benzenesulfonyl)-4-methyl-piperidin-3-yl]-methyl-(7H-pyrrolo[2,3-d]pyrimidin-4-yl)-amine

LRMS: 522.

EXAMPLE 243

[1-(3,5-Dichloro-benzenesulfonyl)-4-methyl-piperidin-3-yl]-methyl-(7H-pyrrolo[2,3-d]pyrimidin-4-yl)-amine

LRMS: 455.

EXAMPLE 244

4-{4-Methyl-3-[methyl-(7H-pyrrolo[2,3-d]pyrimidin-4-yl)-amino]-piperidine-1-sulfonyl}-benzoic acid

LRMS: 431.

EXAMPLE 245

(3-Fluoro-phenyl)-{4-methyl-3-[methyl-(7H-pyrrolo[2,3-d]pyrimidin-4-yl)-amino]-piperidin-1-yl}-methanone

LRMS: 368.

EXAMPLE 246

Isothiazol-4-yl-{4-methyl-3-[methyl-(7H-pyrrolo[2,3-d]pyrimidin-4-yl)-amino]-piperidin-1-yl-methanone

LRMS: 357.

EXAMPLE 247

{4-Methyl-3-[methyl-(7H-pyrrolo[2,3-d]pyrimidin-4-yl)-amino]-piperidin-1-yl}-thiophen-3-yl-methanone

LRMS: 356.

EXAMPLE 248

{4-Methyl-3-[methyl-(7H-pyrrolo[2,3-d]pyrimidin-4-yl)-amino]-piperidin-1-yl}-(5-methyl-1H-pyrazol-3-yl)-methanone

LRMS: 354.

EXAMPLE 249

(5-Methyl-isoxazol-3-yl)-(4-methyl-3-[methyl-(7H-pyrrolo[2,3-d]pyrimidin-4-yl)-amino]-piperidin-1-yl}-methanone

LRMS: 355.

EXAMPLE 250

{4-Methyl-3-[methyl-(7H-pyrrolo[2,3-d]pyrimidin-4-yl)-amino]-piperidin-1-yl}-(5-methyl-thiophen-2-yl)-methanone

LRMS: 371.

EXAMPLE 251

(4-Fluoro-phenyl)-{4-methyl-3-[methyl-(7H-pyrrolo[2,3-d]pyrimidin-4-yl)-amino]-piperidin-1-yl}-methanone

LRMS: 368.

EXAMPLE 252

Methyl-[4-methyl-1-(3-nitro-benzenesulfonyl)-piperidin-3-yl]-(7H-pyrrolo[2,3-d]pyrimidin-4-yl)-amine

LRMS: 431.

EXAMPLE 253

[1-(3-Fluoro-benzenesulfonyl)-4-methyl-piperidin-3-yl]-methyl-(7H-pyrrolo[2,3-d]pyrimidin-4-yl)-amine

LRMS: 404.

EXAMPLE 254

(2-Fluoro-phenyl)-{4-methyl-3-[methyl-(7H-pyrrolo[2,3-d]pyrimidin-4-yl)-amino]-piperidin-1-yl}-methanone

LRMS: 368.

EXAMPLE 255

(1,5-Dimethyl-1H-pyrazol-3-yl)-{4-methyl-3-[methyl-(7H-pyrrolo[2,3-d]pyrimidin-4-yl)-amino]-piperidin-1-yl}-methanone

LRMS: 368.

EXAMPLE 256

{4-Methyl-3-[methyl-(7H-pyrrolo[2,3-d]pyrimidin-4-yl)-amino]-piperidin-1-yl}-(2-methyl-thiazol-4-yl)-methanone

LRMS: 371.

EXAMPLE 257

{4-Methyl-3-[methyl-(7H-pyrrolo[2,3-d]pyrimidin-4-yl)-amino]-piperidin-1-yl}-thiazol-4-yl-methanone

LRMS: 357.

EXAMPLE 258

(4-Methyl-isothiazol-5-yl)-{4-methyl-3-[methyl-(7H-pyrrolo[2,3-d]pyrimidin-4-yl)-amino]-piperidin-1-yl}-methanone

LRMS: 371.

EXAMPLE 259

2,2-Dimethyl-5-(2-{4-methyl-3-[methyl-(7H-pyrrolo[2,3-d]pyrimidin-4-yl)-amino]-piperidin-1-yl}-2-oxo-ethyl)-[1,3]dioxolan-4-one

LRMS: 403.

EXAMPLE 260

2-Cyclopropyl-N-(2-{4-methyl-3-[methyl-(7H-pyrrolo[2,3-d]pyrimidin-4-yl)-amino]-piperidine-1-sulfonyl}-ethyl)-acetamide

LRMS: 436.

EXAMPLE 261

N-(2-{4-Methyl-3-[methyl-(7H-pyrrolo[2,3-d]pyrimidin-4-yl)-amino]-piperidine-1-sulfonyl}-ethyl)-methanesulfonamide

LRMS: 432.

EXAMPLE 262

(3-Hydroxy-pyrrolidin-1-yl)-{4-methyl-3-[methyl-(7H-pyrrolo[2,3-d]pyrimidin-4-yl)-amino]-piperidin-1-yl}-methanone

LRMS: 359.

EXAMPLE 263

4-{4-Methyl-3-[methyl-(7H-pyrrolo[2,3-d]pyrimidin-4-yl)-amino]-piperidin-1-ylmethyl}-benzonitrile

LRMS: 362.

EXAMPLE 264

3-{4-Methyl-3-[methyl-(7H-pyrrolo[2,3-d]pyrimidin-4-yl)-amino]-piperidine-1-sulfonyl}-benzenesulfonyl fluoride

LRMS: 469.

EXAMPLE 265

2,2-Dimethyl-5-(2-{4-methyl-3-[methyl-(7H-pyrrolo[2,3-d]pyrimidin-4-yl)-amino]-piperidin-1-yl}-2-oxo-ethyl)-[1,3]dioxolan-4-one

LRMS: 402.

EXAMPLE 266

4-Methyl-3-[methyl-(7H-pyrrolo[2,3-d]pyrimidin-4-yl)-amino]-piperidine-1-carboxylic acid benzyl ester

LRMS: 381.

EXAMPLE 267

4-{4-Methyl-3-[methyl-(7H-pyrrolo[2,3-d]pyrimidin-4-yl)-amino]-piperidin-1-ylmethyl}-benzenesulfonamide

LRMS: 416.

EXAMPLE 268

[1-(1H-Imidazol-2-ylmethyl)-4-methyl-piperidin-3-yl]-methyl-(7H-pyrrolo[2,3d]pyrimidin-4-yl)-amine

LRMS: 326.

EXAMPLE 269

4-Methyl-3-[methyl-(7H-pyrrolo[2,3-d]pyrimidin-4-yl)-amino]-piperidine-1-carboxylic acid 2-chloro-benzyl ester

LRMS: 415.

EXAMPLE 270

Methyl-[4-methyl-1-(1-methyl-1H-imidazol-2-ylmethyl)-piperidin-3-yl]-(7H-pyrrolo[2,3-d]pyrimidin-4-yl)-amine

LRMS: 340.

EXAMPLE 271

1-{4-Methyl-3-[methyl-(7H-pyrrolo[2,3-d]pyrimidin-4-yl)-amino]-piperidin-1-yl}-2-phenoxy-ethanone

LRMS: 380.

EXAMPLE 272

2-(4-Fluoro-phenoxy)-1-{4-methyl-3-[methyl-(7H-pyrrolo[2,3-d]pyrimidin-4-yl)-amino]-piperidin-1-yl}-ethanone

LRMS: 381.

EXAMPLE 273

4-Methyl-3-[methyl-(7H-pyrrolo[2,3-d]pyrimidin-4-yl)-amino]-piperidine-1-carboxylic acid 2,2,2-trichloro-ethyl ester

LRMS: 420.

EXAMPLE 274

2-(2-Chloro-phenoxy)-1-{4-methyl-3-[methyl-(7H-pyrrolo[2,3-d]pyrimidin-4-yl)-amino]-piperidin-1-yl}-ethanone

LRMS: 415.

EXAMPLE 275

2-(3-Chloro-phenoxy)-1-{4-methyl-3-[methyl-(7H-pyrrolo[2,3-d]pyrimidin-4-yl)-amino]-piperidin-1-yl}-ethanone

LRMS: 415.

EXAMPLE 276

2-Methanesulfonyl-1-{4-methyl-3-[methyl-(7H-pyrrolo[2,3-d]pyrimidin-4-yl)-amino]-piperidin-1-yl}-ethanone

LRMS: 367.

EXAMPLE 277

2-(1,1-Dioxo-tetrahydro-1$I%6&-thiophen-3-yl)-1-{4-methyl-3-[methyl-(7H-pyrrolo[2,3-d]pyrimidin-4-yl)-amino]-piperidin-1-yl}-ethanone

LRMS: 407.

EXAMPLE 278

Methyl-[4-methyl-1-(1-phenyl-ethyl)-piperidin-3-yl]-(7H-pyrrolo[2,3-d]pyrimidin-4-yl)-amine

LRMS: 351.

EXAMPLE 279

1-{4-Methyl-3-[methyl-(7H-pyrrolo[2,3-d]pyrimidin-4-yl)-amino]-piperidin-1-yl}-2-(toluene-4-sulfonyl)-ethanone

LRMS: 443.

EXAMPLE 280

2-Hydroxy-1-{4-methyl-3-[methyl-(7H-pyrrolo[2,3-d]pyrimidin-4-yl)-amino]-piperidin-1-yl}-ethanone

LRMS: 304.

EXAMPLE 281

1-{4-Methyl-3-[methyl-(7H-pyrrolo[2,3-d]pyrimidin-4-yl)-amino]-piperidin-1-yl}-3-nitro-propan-1-one

LRMS: 347.

EXAMPLE 282

5-(2-{4-Methyl-3-[methyl-(7H-pyrrolo[2,3-d]pyrimidin-4-yl)-amino]-piperidin-1-yl}-2-oxo-ethyl)-thiazolidine-2,4-dione

LRMS: 404.

EXAMPLE 283

3-Hydroxy-1-{4-methyl-3-[methyl-(7H-pyrrolo[2,3-d]pyrimidin-4-yl)-amino]-piperidin-1-yl}-propan-1-one

LRMS: 318.

EXAMPLE 284

N-(4-{4-Methyl-3-[methyl-(7H-pyrrolo[2,3-d]pyrimidin-4-yl)-amino]-piperidin-1-yl}-4-oxo-butyl)-methanesulfonamide

LRMS: 410.

EXAMPLE 285

4-Methyl-3-[methyl-(7H-pyrrolo[2,3-d]pyrimidin-4-yl)-amino]-piperidine-1-carboxylic acid 2,2-dimethyl-propyl ester

LRMS: 360.

EXAMPLE 286

1-{4-Methyl-3-methyl-(7H-pyrrolo[2,3-d]pyrimidin-4-yl)-amino]-piperidin-yl}-2-(thiazolidine-3-sulfonyl)-ethanone

LRMS: 440.

EXAMPLE 287

(3,4-Dihydroxy-pyrrolidin-1-yl)-{4-methyl-3-[methyl-(7H-pyrrolo[2,3-d]pyrimidin-4-yl)-amino]-piperidin-1-yl}-methanone

LRMS: 376.

EXAMPLE 288

4-{4-Methyl-3-[methyl-(7H-pyrrolo[2,3-d]pyrimidin-4-yl)-amino]-piperidine-1-carbonyl}-thiazolidin-2-one

LRMS: 376

EXAMPLE 289

4-Methyl-3-[methyl-(7H-pyrrolo[2,3-d]pyrimidin-4-yl)-amino]-piperidine-1-carboxylic acid prop-2-ynyl ester

LRMS: 328.

EXAMPLE 290

4-Methyl-3-[methyl-(7H-pyrrolo[2,3-d]pyrimidin-4-yl)-amino]-piperidine-1-carboxylic acid (2-cyano-ethyl)-amide

LRMS: 342.

EXAMPLE 291

4-Methyl-3-[methyl-(7H-pyrrolo[2,3-d]pyrimidin-4-yl)-amino]-piperidine-1-carboxylic acid (2-cyano-ethyl)-amide

LRMS: 342.

EXAMPLE 292

1-{4-Methyl-3-[methyl-(7H-pyrrolo[2,3-d]pyrimidin-4-yl)-amino]-cyclohexyl}-ethanone oxime

LRMS: 302.

EXAMPLE 293

4-Methyl-3-[methyl-(7H-pyrrolo[2,3-d]pyrimidin-4-yl)-amino]-piperidine-1-carboxylic acid cyanomethyl-methyl-amide

LRMS: 342.

EXAMPLE 294

4-Methyl-3-[methyl-(7H-pyrrolo[2,3-d]pyrimidin-4-yl)-amino]-piperidine-1-carboxylic acid isopropyl ester

LRMS: 332.

EXAMPLE 295

4-Methyl-3-[methyl-(7H-pyrrolo[2,3-d]pyrimidin-4-yl)-amino]-piperidine-1-carboxylic acid (2-cyano-ethyl)-methyl-amide

LRMS: 356.

EXAMPLE 296

4-{4-Methyl-3-[methyl-(7H-pyrrolo[2,3-d]pyrimidin-4-yl)-amino]-piperidin-1-ylmethyl}-pyridin-1-ol

LRMS: 355.

EXAMPLE 297

{4-Methyl-3-[methyl-(7H-pyrrolo[2,3-d]pyrimidin-4-yl)-amino]-piperidin-1-yl}-acetonitrile

LRMS: 285.

EXAMPLE 298

[1-(2-Fluoro-benzyl)-4-methyl-piperidin-3-yl]-methyl-(7H-pyrrolo[2,3-d]pyrimidin-4-yl)-amine Method J To a solution of the product from Method H (50 mg, mmols?) dissolved in 5 mL of methanol was added 154 ul (mmols?) of 2-fluoro-benzaldehyde. The resulting mixture stirred at room temperature for 4 hours, at which time, x mg (y mmol) of sodium cyanoborohydride were added and the new mixture stirred at room temperature for 18 hours. The reaction was quenched upon addition of 2 drops of 1N NaOH (aq) and the mixture concentrated under reduced pressure to remove the methanol. The residue was dissolved in chloroform and washed with water. The aqueous layer was back washed three times with chloroform, the combined chloroform extracts dried over $MgSO_4$ and concentrated to dryness in vacuo. The crude product was then purified by flash chromatography (silica; 2.5% methanol in chloroform) affording 36 mg (47.5%) of the title compound as a white solid. LRMS: 372.4 (M+1).

The title compounds for examples 299–324 were prepared by the method analogous to that described in Example 298.

EXAMPLE 299

(1-Benzyl-4-methyl-piperidin-3-yl)-methyl-(7H-pyrrolo[2,3-d]pyrimidin-4-yl)-amine

LRMS: 336.

EXAMPLE 300

(1-Furan-2-ylmethyl-4-methyl-piperidin-3-yl)-methyl-(7H-pyrrolo[2,3-d]pyrimidin-4-yl)-amine

LRMS: 326.

EXAMPLE 301

[1-(4-Methoxy-benzyl)-4-methyl-piperidin-3-yl]-methyl-(7H-pyrrolo[2,3-d]pyrimidin-4-yl)-amine

LRMS: 366.

EXAMPLE 302

[1-(4-Fluoro-benzyl)-4-methyl-piperidin-3-yl]-methyl-(7H-pyrrolo[2,3-d]pyrimidin-4-yl)-amine

LRMS: 354.

EXAMPLE 303

Methyl-(4-methyl-1-pyridin-3-ylmethyl-piperidin-3-yl)-(7H-pyrrolo[2,3-d]pyrimidin-4-yl)-amine

LRMS: 337.

EXAMPLE 304

Methyl-(4-methyl-1-thiazol-2-ylmethyl-piperidin-3-yl)-(7H-pyrrolo[2,3-d]pyrimidin-4-yl)-amine

LRMS: 343.

EXAMPLE 305

Methyl-(4-methyl-1-pyridin-2-ylmethyl-piperidin-3-yl)-(7H-pyrrolo[2,3-d]pyrimidin-4-yl)-amine

LRMS: 337.

EXAMPLE 306

Methyl-[4-methyl-1-(1-phenyl-ethyl)-piperidin-3-yl]-(7H-pyrrolo[2,3-d]pyrimidin-4-yl)-amine

LRMS: 350.

EXAMPLE 307

(1-Benzyl-4-methyl-piperidin-3-yl)-methyl-(7H-pyrrolo[2,3-d]pyrimidin-4-yl)-amine

LRMS: 336.

EXAMPLE 308

(1-Benzyl-4-methyl-Piperidin-3-yl)-methyl-(7H-pyrrolo[2,3-d]pyrimidin-4-yl)-amine

LRMS: 336.

EXAMPLE 309

3-{4-Methyl-3-[methyl-(7H-pyrrolo[2,3-d]pyrimidin-4-yl)-amino]-piperidin-1-ylmethyl}-benzonitrile

LRMS: 361.

EXAMPLE 310

[1-(3-Fluoro-benzyl)-4-methyl-piperidin-3-yl]-methyl-(7H-pyrrolo[2,3-d]pyrimidin-4-yl)-amine

LRMS: 354.

EXAMPLE 311

[1-(3-Methoxy-benzyl)-4-methyl-piperidin-3-yl]-methyl-(7H-pyrrolo[2,3-d]pyrimidin-4-yl)-amine

LRMS: 366.

EXAMPLE 312

3-{4-Methyl-3-[methyl-(7H-pyrrolo[2,3-d]pyrimidin-4-yl)-amino]-piperidin-1-ylmethyl}-benzoic acid

LRMS: 380.

EXAMPLE 313

[1-(2-Fluoro-benzyl)-4-methyl-piperidin-3-yl]-methyl-(7H-pyrrolo[2,3-d]pyrimidin-4-yl)-amine

LRMS: 354.

EXAMPLE 314

[1-(2,6-Difluoro-benzyl)-4-methyl-piperidin-3-yl]-methyl-(7H-pyrrolo[2,3-d]pyrimidin-4-yl)-amine

LRMS: 372.

EXAMPLE 315

Methyl-(4-methyl-1-phenethyl-piperidin-3-yl)-(7H-pyrrolo[2,3-d]pyrimidin-4-yl)-amine

LRMS: 350.

EXAMPLE 316

[1-(2,3-Difluoro-benzyl)$_4$-methyl-piperidin-3-yl]-methyl-(7H-pyrrolo[2,3-d]pyrimidin-4-yl)-amine

LRMS: 372.

EXAMPLE 317

[1-(3,4Difluoro-benzyl)-4-methyl-piperidin-3-yl]-methyl-(7H-pyrrolo[2,3-d]pyrimidin-4-yl)-amine

LRMS: 372.

EXAMPLE 318

[1-(4-Methanesulfonyl-benzyl)-4-methyl-piperidin-3-yl]-Methyl-(7H-pyrrolo[2,3-d]pyrimidin-4-yl)-amine

LRMS: 414.

EXAMPLE 319

Methyl-{4-methyl-1-[4-(piperidine-1-sulfonyl)-benzyl]-piperidin-3-yl}-(7H-pyrrolo[2,3-d]pyrimidin-4-yl)-amine

LRMS: 483.

EXAMPLE 320

[1-(3,5-Difluoro-benzyl)$_4$-methyl-piperidin-3-yl]-methyl-(7H-pyrrolo[2,3-d]pyrimidin-4-yl)-amine

LRMS: 372.

EXAMPLE 321

[1-(3-Chloro-benzyl)-4-methyl-piperidin-3-yl]-methyl-(7H-pyrrolo[2,3-d]pyrimidin-4-yl)-amine

LRMS: 371.

EXAMPLE 322

[1-(3,5-Difluoro-benzyl)-4-methyl-piperidin-3-yl]-methyl-(7H-pyrrolo[2,3-d]pyrimidin-4-yl)-amine

LRMS: 372.

EXAMPLE 323

[1-(3-Chloro-benzyl)-4-methyl-piperidin-3-yl]-methyl-(7H-pyrrolo[2,3-d]pyrimidin-4-yl)-amine

LRMS: 371.

EXAMPLE 324

[1-(3,5-Dichloro-benzyl)-4-methyl-piperidin-3-yl]-methyl-(7H-pyrrolo[2,3-d]pyrimidin-4-yl)-amine

LRMS: 405.

The invention claimed is:

1. A method for the inhibition of Janus kinase 3 (JAK 3) in a mammal, comprising administering to said mammal an effective amount of a compound of the formula

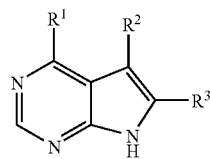

I or a pharmaceutically acceptable salt thereof; wherein $R^1$ is a group of the formula

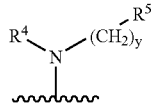

wherein y is 0, 1 or 2;

$R^4$ selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^5$ is $(C_2-C_9)$heterocycloalkyl wherein the heterocycloalkyl groups must be substituted by one to five groups consisting of carboxy, cyano, amino, deuterium, hydroxy, $(C_1-C_6)$alkyl, $(C_1-C_6)$alkoxy, halo, $(C_6C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$ alkynyl, $(C_1-C_6)$ alkylkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acyl amino, amino $(C_1-C_6)$acyl, amino$(C_1-C_6)$acyl$(C_1-C_6)$alkyl, $(C_1-C_6)$alkylamino$(C_1-C_6)$acyl, $((C_1-C_6)$acyl$)_2$amino$(C_1-C_6)$ acyl, $R^{15}R^{16}N$—CO—O—, $R^{15}R^{16}N$—CO—$(C_1C_6)$alkyl, $(C_1-C_6)$alkyl-S $(O)_m$, $R^{15}R^{16}NS(O)_m$, $R_{15}R^{16}NS(O)_m$ $(C_1-C_6)$alkyl, $R^{15}S(O)_m$ $R^{16}N$, $R^{15}S(O)_m R^{16}N$ $(C_1-C_6)$alkyl, and a group of the formula II

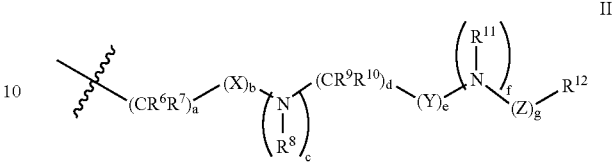

II wherein:

m is 0, 1 or 2;

$R^{15}$ and $R^{16}$ are each independently selected from hydrogen or $(C_1-C_6)$alkyl;

a is 0, 1,2,3or 4;

b, c, e, f and g are each independently 0 or 1;

d is 0, 1, 2, or 3;

X is $S(O)_n$ wherein n is 0, 1 or 2; oxygen, carbonyl or —C(=N-cyano)-;

Y is $S(O)_n$ wherein n is 0, 1 or 2; or carbonyl; and

Z is carbonyl, C(O)O—, C(O)NR— wherein R is hydrogen or $(C_1-C_6)$alkyl; or Z is $S(O)_n$ wherein n is 0, 1 or 2;

$R^6$, $R^7$, $R^8$, $R^9$, $R^{10}$ and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkyiamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^{12}$ is $(C_6-C_{10})$aryl, $(C_2-C_9)$heteroaryl, tetrazolyl, or $(C_2-C_9)$heterocycloalkyl, wherein the aryl, heteroaryl, terrazolyl, and heterocycloalkyl groups are optionally substituted by one to four groups consisting of hydrogen, deuterium, amino, halo, oxo, hydroxy, nitro, carboxy, $(C_2-C_6)$alkenyl, $(C_2-C_6)$alkynyl, trifluoromahyl, trifluoromethoxy, $(C_1-C_6)$alkyl, $(C_1-C_6)$alkoxy, $(C_3-C_{10})$cycloalkyl, $(C_1-C_6)$alkyl-CO—NH—, $(C_1-C_6)$alkoxy-CO—NH—, $(C_1-C_6)$alkyl-CO—NH—$(C_1-C_6)$alkyl, $(C_1-C_6)$alkoxy-CO—NH—$(C_1-C_6)$alkyl, $(C_1-C_6)$alkoxy-CO—NH—$(C_1-C_6)$alkoxy, carboxy, carboxy$(C_1-C_6$alkyi, carboxy$(C_1-C_6)$alkoxy, benzyloxycarbonyl$(C_1-C_6)$alkoxy, $(C_1-C_6)$alkoxycarbonyl$(C_1-C_6)$alkoxy, $(C_6-C_{10})$aryl, amino, amino$(C_1-C_6)$alkyl, $(C_1-C_6)$alkoxycarbonylamino, $(C_6-C_{10})$aryl$(C_1-C_6)$alkoxycarbonylamino, $(C_1-C_6)$alkylamino, $((C_1-C_6)$alkyl$)_2$amino, $(C_1-C_6)$ alkylamino$(C_1-C_6)$alkyl, $((C_1-C_6)$alkyl$)_2$amino$(C_1-C_6)$alkyl, hydroxy, $(C_1-C_6)$alkoxy, carboxy, $(C_1)$alkyl, $(C_1-C_6)$alkoxycarbonyl, $(C_{12}-C_6)$alkoxycarbonyl $(C_1-C_6)$alkyl, $(C_1-C_6)$alkoxy -CO—NH—, $(C_1-C_6)$alkyl -CO—NH—, cyano, $(C_5-C_9)$heterocycloalkyl, amino-CO—NH—, $(C_1-C_6)$alkylamino-CO—NH—, $((C_1-C_6)$alkyl$)_2$amino-CO—NH—, $(C_6-C_{10})$arylamino-CO—NH—, $(C_5-C_9)$heteroarylamino-CO—NH—, $(C_1-C_6)$alkylamino-CO—NH—$(C_1-C_6)$alkyl, $((C_1-C_6)$alkyl$)_2$amino-CO—NH—$(C_1-C_6)$alkyl, $(C_6-C_{10})$arylamino-CO—NH—$(C_1-C_6)$alkyl, $(C_5-C_9)$heteroarylamino-CO—NH—$(C_1-C_6)$ alkyl, cyano $(C_1-C_6)$alkyl, carboxy$(C_1-C_6)$alkyl$(C_1-C_6)$alkoxy, carboxy$(C_1-C_6)$alkyl, sulfonylamino, aminosulfonyl, sulfonylamino$(C_1-C_6)$alkyl, sulfonylaminocarboxy ($C_1$–$C_6$)alkyl, ($C_1$–$C_6$)alkylsulfonyl, ($C_1$–$C_6$)alkylsulfonylamino, ($C_1$–$C_6$)alkylsulfonylamino($C_1$–$C_6$)alkyl, ($C_6$–$C_{10}$)arylsulfonyl, ($C_6$–$C_{10}$)arylsulfonylamino, ($C_6$$C_{10}$)arylsulfonylamino($C_1$–$C_6$)alkyl, ($C_1$–$C_6$)alkylsulfonylamino, ($C_1$–$C_6$)alkylsulfonylamino($C_1$–$C_6$) alkyl, ($C_3$–$C_{10}$)cycloalkyl, ($C_3$–$C_{10}$)cycloalkoxy, ($C_1$–$C_6$)alkylamino, (($C_1$–$C_6$)alkyl)$_2$amino, ($C_6$–$C_6$)arylamino, ($C_1$–$C_6$)alkylthio, ($C_6$–$C_{10}$) arylthio, ($C_1$–$C_6$)alkylsulfinyl, ($C_6$–$C_{10}$)arylsulfinyl, ($C_1$–$C_6$) alkylsulfonyl, ($C_6$–$C_{10}$)arylsulfonyl, ($C_1$–$C_6$) acyl, ($C_1$–$C_6$)alkoxy-CO—NH—, ($C_1$–$C_6$)alkylamino-CO—, ($C_5$–$C_9$)heteroaryl, ($C_2$–$C_9$)heterocycloalkyl or ($C_6$–$C_{10}$)aryl wherein the heteroaryl, tetrazolyl, heterocycloalkyl and aryl groups which are optionally substituted on $R^{12}$ may be further substituted by one to three groups consisting of halo, ($C_1$–$C_6$)alkyl, ($C_1$–$C_6$) alkyl-CO—NH—, ($C_1$–$C_6$)alkoxy-CO—NH—, ($C_1$–$C_6$)alkyl-CO—NH—($C_1$–$C_6$)alkyl, $C_1$–$C_6$) alkoxy-CO—NH—($C_1$–$C_6$)alkyl, ($C_1$–$C_6$)alkoxy-CO—NH—($C_1$–$C_6$)alkoxy, carboxy, carboxy($C_1$–$C_6$) alkyl, carboxy($C_1$–C6)alkoxy, benzyloxycarbonyl ($C_1$–$C_6$)alkoxy, ($C_1$–$C_6$)alkoxycarbonyl($C_1$–$C_6$) alkoxy, ($C_6$–$C_{10}$)aryl, amino, amino($C_1$–$C_6$)alkyl, ($C_1$–$C_6$)alkoxycarbonylamino, ($C_6$–$C_{10}$)aryl($C_1$–$C_6$) alkoxycarbonylaniino, ($C_1$–$C_3$alkylamino, (($C_1$–$C_6$) alkyl )$_2$amino, ($C_1$–$C_6$)alkylamino($C_1$–$C_6$)alkyl, (($C_1$–$C_6$)$_2$amino($C_1$–$C_6$)alkyl, hydroxy, ($C_1$–$C_6$) alkoxy, carboxy, carboxy($C_1$–$C_6$)alkyl, ($C_1$–$C_6$) alkoxycarbonyl, ($C_1$–$C_6$)alkoxycarbonyl($C_1$–$C_6$)alkyl, ($C_1$–$C_6$)alkoxy-CO—NH—, ($C_1$–$C_6$)alkyl-CO—NH —, cyano, ($C_5$–$C_9$)heterocycloalkyl, amino-CO—NH—, ($C_1$–$C_6$)alkylamino-CO—NH—, (($C_1$–$C_6$) alkyl)$_2$amino-CO—NH—, ($C_6$–$C_{10}$)arylamino-CO—NH—, ($C_5$–$C_9$)heteroarylamino-CO—NH—, ($C_1$–$C_6$) alkylamino-CO—NH—($C_1$–$C_6$)alkyl, (($C_1$–$C_6$)alkyl)$_2$ amino-CO—NH—($C_1$–$C_6$)alkyl, ($C_6$–$C_{10}$)arylamino-C O—NH—($C_1$–$C_6$)alkyl, ($C_5$–$C_9$)heteroarylamino-CO—NH—($C_1$–$C_6$)alkyl, ($C_1$–$C_6$)alkylsulfonyl, ($C_1$–$C_6$) alkylsulfonylamino, ($C_1$–$C_6$) alkylsulfonylamino($C_1$–$C_6$)alkyl, ($C_6$–$C_{10}$) arylsulfonyl, ($C_6$–$C_{10}$)arylsulfonylamino, ($C_6$–$C_{10}$) arylsulfonylamino($C_1$–$C_6$)alkyl, ($C_1$–$C_6$) alkylsulfonylamino, ($C_1$–$C_6$) alkylsulfonylamino ($C_1$–$C_6$)alkyl, ($C_5$–$C_9$)heteroaryl and ($C_2$–$C_9$) heterocycloalkyl;

$R^2$ and $R^3$ are each independently selected from the group consisting of hydrogen, deuterium, amino, halo, hydroxy, nitro, carboxy, ($C_2$–$C_6$)alkenyl, ($C_2$–$C_6$)alkynyl, trifluoromethyl, trifluoromethoxy, ($C_1$–$C_6$)alkyl, ($C_1$–$C_6$)alkoxy, ($C_3$–$C_{10}$)cycloalkyl wherein the alkyl, alkoxy or cycloalkyl groups are optionally substituted by one to three groups selected from halo, hydroxy, carboxy, amino ($C_1$–$C_6$)alkylthio, ($C_1$–$C_6$)alkylamino, (($C_1$–$C_6$)alkyl)$_2$amino, ($C_5$–$C_9$)heteroaryl, ($C_2$–$C_9$)heterocycloalkyl, ($C_3$–$C_9$)cycloalkyl or ($C_6$–$C_{10}$)aryl; or $R^2$ and $R^3$ are each independently ($C_3$–$C_{10}$)cycloalkyl, ($C_3$–$C_{10}$)cycloalkoxy, ($C_1$–$C_6$)alkylamino, (($C_1$–$C_6$) alkyl)$_2$amino, ($C_6$–$C_{10}$)arylamino, ($C_1$–$C_6$)alkylthio, ($C_6$–$C_{10}$)arylthio, ($C_1$–$C_6$)alkylsulfinyl, ($C_6$–$C_{10}$) arylsulfinyl, ($C_1$–$C_6$)alkylsulfonyl, ($C_6$–$C_{10}$)arylsulfony, ($C_1$–$C_6$)acyl, ($C_1$–$C_6$)alkoxy-CO—NH—, ($C_1$–$C_6$) alkylamino-CO—, ($C_5$–$C_9$)heteroaryl, ($C_2$–$C_9$)heterocycloalkyl or ($C_6$–$C_{10}$)aryl wherein the heteroaryl, heterocycloalkyl and aryl groups are optionally substituted by one to three halo, ($C_1$–$C_6$)alkyl, ($C_1$–$C_6$)alkyl-CO—NH—, ($C_1$–$C_6$)alkoxy-CO—NH—, ($C_1$–$C_6$)alkyl-CO—NH—($C_{12}$–$C_6$)alkyl, ($C_1$$C_6$)alkoxy-CO—NH—($C_1$–$C_6$)alkyl, ($C_1$–$C_9$)alkoxy-CO—NH—($C_1$–$C_6$) alkoxy, carboxy, carboxy($C_1$–$C_6$)alkyl, carboxy($C_1$$C_6$) alkoxy, benzyloxycarbonyl($C_1$–$C_6$)alkoxy, ($C_1$–$C_6$) alkoxycarbonyl($C_1$–$C_6$)alkoxy, ($C_6$–$C_{10}$aryl, amino, amino($C_1$–$C_6$)alkyl, ($C_1$–$C_6$)alkoxycarbonylamino, ($C_6$–$C_{10}$)aryl($C_1$–$C_6$) alkoxycarbonylamino, ($C_1$–$C_6$) alkylamino, (($C_1$–$C_6$)alkyl)$_2$amino, ($C_1$–$C_6$)alkylamino($C_1$–$C_6$)alkyl, (($C_1$C6)alkyl)$_2$amino($C_1$–$C_6$) alkyl, hydroxy, ($C_1$–$C_6$)alkoxy, carboxy, carboxy ($C_1$–$C_6$)alkyl, ($C_1$–$C_6$)alkoxycarbonyl, ($C_1$–$C_6$) alkoxycarbonyl($C_1$–$C_6$)alkyl, ($C_1$–$C_6$)alkoxy-CO—NH—, ($C_1$–$C_6$)alkyl-CO—NH—, cyano, ($C_5$–$C_9$) heterocycloalkyl, amino-CO—NH—, ($C_1$–$C_6$) alkylamino-CO—NH—, (($C_1$–$C_6$)alkyl)$_2$amino-CO—NH—, ($C_6$–$C_{10}$)arylamino-CO—NH—, ($C_5$–$C_9$) heteroarylamino-CO—NH—, ($C_1$–$C_6$)alkylamino-CO—NH—($C_1$–$C_6$)alkyl, (($C_1$–$C_6$)alkyl)$_2$amino-CO—NH—($C_1$–$C_6$)alkyl, ($C_6$–$C_{10}$) arylarnino-CO—NH—($C_1$–$C_6$)alkyl, ($C_5$–$C_9$)heteroarylamino-CO—NH—($C_1$–$C_6$)alkyl, ($C_1$–$C_6$)alkylsulfonyl, ($C_1$–$C_6$) alkylsulfonylamino, ($C_1$–$C_6$)alkylsulfonylamino ($C_1$–$C_6$)alkyl, ($C_6$–$C_{10}$)arylsulfonyl, ($C_6$–$C_{10}$)arylsulfonylamino, ($C_6$–$C_{10}$)arylsulfonyiamino($C_1$–$C_6$)alkyl, ($C_1$–$C_6$)alkylsulfonylamino, ($C_1$–$C_6$)alkylsulfonylamino, ($C_1$–$C_6$)alkyl, ($C_5$–$C_9$)heteroaryl or ($C_2$–$C_9$) heterocycloalkyl;

with the proviso that $R^5$ must be substituted by the group of formula II;

alone or in combination with one or more additional agents which modulate a mammalian immune system or with anti-inflammatory agents.

2. The method according to claim 1, wherein $R^5$ is ($C_2$–$C_9$)heterocycioalkyl optionally substituted by one to three groups selected from deuterium, hydroxy, ($C_1$–$C_6$) alkyl, halo, ($C_1$–$C_6$)alkoxy and a group of formula II.

3. The method according to claim 1, wherein a is 0; b is 1; X is carbonyl; c is 0; d is 0; e is 0; f is 0; and g is 0.

4. The method according to claim 1, wherein a is 0; b is 1; X is carbonyl; c is 0; d is 1; e is 0; f is 0, and g is 0.

5. The method according to claim 1, wherein a is 0; b is 1; X is carbonyl; c is 1; d is 0; e is 0; f is 0; and g is 0.

6. The method according to claim 1, wherein a is 0; b is 1; X is C(=N=cyano)-; c is 1; d is 0; e is 0; f is 0; and g is 0.

7. The method according to claim 1, wherein a is 0; b is 0; c is 0; d is 0; e is 0; f is 0; g is 1; and Z is —C(O)—O—.

8. The method according to claim 1, wherein a is 0; b is 1; X is S(O)$_n$: n is 2; c is 0; d is 0; e is 0; f is 0; and g is 0.

9. The method according to claim 1, wherein a is 0; b is 1; X is S(O)$_n$; n is 2; c is 0; d is 2; e is 0; f is 1;g is 1; and Z is carbonyl.

10. The method according to claim 1, wherein a is 0; b is 1; X is S(O)$_n$; n is 2; c is 0; d is 2; e is 0; f is 1; and g is 0.

11. The method according to claim 1, wherein a is 0; b is 1; X is carbonyl; c is 1; d is 0; e is 1; Y is S(O)$_n$; H is 2; f is 0; and g is 0.

12. The method according to claim 1, wherein a is 0; b is 1; X is S(O)$_n$; n is 2; c is 1; d is 0; c is 0; f is 0; and g is 0.

13. The method according to claim 1, wherein a is 1; b is 1; X is carbonyl; c is 1; d is 0; c is 0; f is 0; and g is 0.

14. The method according to claim 1, wherein a is 0; b is 1; X is S(O)$_n$; c is 0; d is 1; e is 1; Y is S(O)$_n$; n is 2; f is 0; and g is 0.

15. The method according to claim 1, wherein a is 0; b is 1; X is S(O)$_n$; c is 0; d is 1; e is 1; Y is S(O)$_n$; n is 2; f is 1; and g is 0.

16. The method according to claim 1, wherein a is 0; b is 1; X is oxygen; c is 0; d is 1; e is 1; Y is $S(O)_n$; n is 2; f is 1; and g is 0.

17. The method according to claim 1, wherein a is 0; h is 1; X is oxygen; c is 0; d is 1; e is 1; Y is $S(O)_n$; n is 2; f is 0; and g is 0.

18. The method according to claim 1, wherein a is 0; h is 1; X is carbonyl; c is 1; d is 1; e is 1; Y is $S(O)_n$; f is 0; and g is 0.

19. The method according to claim 1, wherein a is 0; b is 1; X is carbonyl; c is 1; d is 1; e is 1; Y is $S(O)_n$; n is 2; f is 1; and g is 0.

20. The method according to claim 1, wherein $R^{12}$ is $(C_6–C_{10})$aryl or $(C_2–C_9)$heteroaryl or tetrazolyl wherein the aryl or heteroaryl or tetrazolyl group is optionally substituted by one to four groups consisting of hydrogen, halo, hydroxy, carboxy, trifluoromethyl, $(C_6)$alkyl, $(C_1–C_6)$ alkoxy, $(C_1–C_6)$alkyl-CO—NH—, amino, amino$(C_1–C_6)$ alkyl, $(C_1–C_6)$alkylamino, $((C_1–C_6)$alkyl$)_2$ amino, cyano, amino-CO—NH—, $(C_1–C_6)$alkylamino-CO—NH—, $((C_1–C_6)$alkyl$)_2$amino-CONH—, $(C_5–C_9)$heteroarylamino-CO—NH—, $(C_1–C_6)$alkylsulfonyl, $(C_1–C_6)$alkylsuifonylamino, $(C_6–C_{10})$arylsulfonylamino, $(C_1–C_6)$alkylsulfonylamino, and $C_1–C_6)$alkoxy-CO—NH—.

21. A method for the inhibition of Janus Kinase 3 (JAK3) in a mammal comprising administering to said mammal an effective amount of a compound selected from the group consisting of:

4-{4-Methyl-3-[methyl-(7H-pyrrolo[2,3-d]pyrimidin-4-yl)-amino]-piperidin-1-ylmethyl}-benzenesulfonamide;

4-Methyl-3-[methyl-(7H-pyrrolo[2,3-d]pyrimidin-4-yl)-amino]-piperidine-1-carboxylic acid (4-sulfamoyl-phenyl )-amide;

4-Methyl-3-[methyl-(7H-pyrrolo[2,3-d]pyrimidin-4-yl)-amino]-piperidine-1-carboxylic acid (4-nitro-phenyl)-amide;

1-{4-Methyl-3-[methyl-(7H-pyrrolo[2,3-d]pyrimidin-4-yl)-amino]-piperidin-1yl}-2-tetrazol-1-yl-ethanone;

4-Methyl -3[methyl-(7H-pyrrolo[2,3-d]pyrimidin-4-yl)-amino]-piperidine-1-carboxylic acid (4-methylsulfamoyl-phenyl)-amide;

(3-Hydroxy-pyrrolidin-1-yl)-{4-methyl-3-[methyl-(7H-pyrrolo[2,3-d]pyrimidin-4-yl)-amino]-piperidin-1-yl }-methanone;

[2-({4-Methyl-3-[methyl-(7H-pyrrolo[2,3-d]pyrimidin-4-yl)-amino]-piperidine-1-carbonyl}-amino)-thiazol-4-yl]-acetic acid;

5-(2-{4-Methyl-3-[methyl-(7H-pyrrolo[2,3-d]pyrimidin-4-yl)-amino]piperidin-1-yl}-2-oxo-ethyl)-thiazolidine-2,4-dione;

{4-Methyl-3-[methyl-(7H-pyrrolo[2,3-d]pyrimidin-4-yl)-amino]-piperidin-1yl}-thiazolidin-3-yl-methanone;

Methyl-[4-methyl-1-(5-nitro-thiazol-2-yl)-piperidin-3-yl]-(7H-pyrrolo[2,3-d]pyrimidin-4-yl)-amine;

[2-({4-Methyl-3-[methyl-(7H-pyrrolo[2,3-d]pyrimidin-4-yl)-amino]-piperidine-1-carbonyl}-amino)-thiazol-4-yl]-acetic acid ethyl ester;

4-Methyl-3-[methyl-(7H-pyrrolo[2,3-d]pyrimidin-4-yl)-amino]-piperidine-1-carboxylic acid (4-methanesulfonyl-phenyl)-amide;

4-Methyl-3-[methyl-(7H-pyrrolo[2,3-d]pyrimidin-4-yl)-amino]-piperidine-1-carboxylic acid (4-cyano-phenyl)-amide;

{4-Methyl-3-[methyl-(7H-pyrrolo[2,3-d]pyrimidin-4-yl)-amino]-piperidin-1-yl}-pyrrolidin-1-yl-methanone;

Furan-2-carboxylic acid (2-{4-methyl-3-[methyl-(7H-pyrrolo[2,3-d]pyrimidin-4-yl)-amino]-piperidine-1-sulfonyl}-ethyl)-amide;

{4-Methyl-3-[methyl-(7H-pyrrolo[2,3-d]pyrimidin-4-yl)-amino]-piperidin-1-yl}(tetrahydro-furan-3-yl)-methanone;

4-Methyl-3-[methyl-(7H-pyrrolo[2,3-d]pyrimidin-4-yl)-amino]-piperidine-1-carboxylic acid isoxazol-3-ylamide;

4-Methyl-3-[methyl-(7H-pyrrolo[2,3-d]pyrimidin-4-yl )-amino]-piperidine-1-carboxylic acid (6-cyano-pyridin-3-yl)-amide;

4-Methyl-3-[methyl-(7H-pyrrolo[2,3-d]pyrimidin-4-yl)-amino]-piperidine-1-carboxylic acid (4-methyl-thiazol-2-yl)-amide;

2-Cyclopropyl-1-{4-methyl-3-[methyl-(7H-pyrrolo[2,3-d]pyrimidin-4yl)-amino]-piperidin-1-yl}-ethanone;

Cyclopentyl-{4-methyl-3-[methyl-(7H-pyrrolo[2,3-d]pyrimidin-4-yl)-amino]-piperidin-1-yl}-Methanone;

4-Methyl-3-[methyl-(7H-pyrrolo[2,3-d]pyrimidin-4-yl)-amino]-piperidine-1-carboxylic acid (3-methyl-isoxazol-4-yl)-amide;

[4-({4-Methyl-3-[methyl-(7H-pyrrolo[2,3-d]pyrimidin-4-yl)-amino]-piperidine-1-carbonyl}-amino)-phenyl]-acetic acid;

[1-(5-Amino-thiazol-2-yl)-4-methyl-piperidin-3-yl]-methyl-(7H-pyrrolo[2,3-d]pyrimidin-4yl)-amine;

4-Methyl-3-[methyl-(7H-pyrrolo[2,3-d]pyrimidin-4-yl)-amino]-piperidine-1carboxylic acid (3-methyl-isothiazol-5-yl)-amide;

3-{4-Methyl-3-[methyl-(7H-pyrrolo[2,3-d]pyrimidin-4-yl)-amino]-piperidine-1-carbonyl}cyclopentanone; and 4-Methyl-3-[methyl-(7H-pyrrolo[2,3-d]pyrimidin-4-yl)-amino]-piperidine-1-carboxylic acid benzyl-methylamide; or a pharmaceutically acceptable salt thereof.

22. A method for treating organ transplant rejection comprising administering to a mammal an effective amount of a compound of the formula

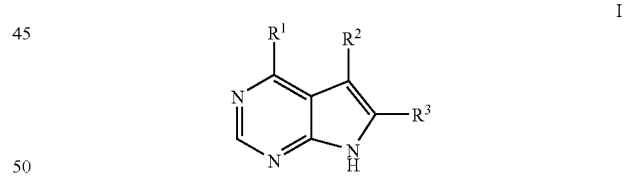

I or a pharmaceutically acceptable salt thereof; wherein
$R^1$ is a group of the formula

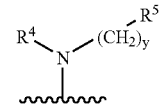

wherein y is 0, 1 or 2;
$R^4$ is selected from the group consisting of hydrogen, $(C_1–C_6)$alkyl, $(C_1–C_6)$alkylsulfonyl, $(C_2–C_6)$alkenyl, $(C_2–C_6)$alkynyl wherein the alkyl, alkenyl and alkynyl groups are optionally substituted by deuterium, hydroxy, amino, trifluoromethyl, $(C_1–C_4)$alkoxy, ($C_1$–$C_6$)acyloxy, ($C_1$–$C_6$)alkylamino, (($C_1$–$C_6$)alkyl)$_2$amino, cyano, nitro, ($C_2$–$C_6$)alkenyl, ($C_2$–$C_6$)alkynyl or ($C_1$–$C_6$)acylamino; or $R^4$ is ($C_3$–$C_{10}$)cycloalkyl wherein the cycloalkyl group is optionally substituted by deuterium, hydroxy, amino, trifluoromethyl, ($C_1$–$C_6$)acyloxy, ($C_1$–$C_6$)acylamino, ($C_1$–$C_6$)alkylamino, (($C_1$–$C_6$)alkyl)$_2$amino, cyano, cyano($C_1$–$C_6$)alkyl, trifluoromethyl($C_1$–$C_6$)alkyl, nitro, nitro($C_1$–$C_6$)alkyl or ($C_1$–$C_6$)acylamino;

$R^5$ is ($C_2$–$C_9$)heterocycloalkyl wherein the heterocycloalkyl groups must be substituted by one to five groups consisting of carboxy, cyano, amino, deuterium, hydroxy, ($C_1$–$C_6$)alkyl, ($C_1$–$C_6$)alkoxy, halo, ($C_1$–$C_6$)acyl, ($C_1$–$C_6$)alkylamino, amino($C_1$–$C_6$)alkyl, ($C_1$–$C_6$)alkoxy-CO—NH, ($C_1$–$C_6$)alkylamino-CO—, ($C_2$–$C_6$)alkenyl, ($C_2$–$C_6$)alkynyl, ($C_1$–$C_6$)alkylamino, amino($C_1$–$C_6$)alkyl, hydroxy($C_1$–$C_6$)alkyl, ($C_1$–$C_6$)alkoxy($C_1$–$C_6$)alkyl, ($C_1$–$C_6$)acyloxy($C_1$–$C_6$)alkyl, nitro, cyano($C_1$–$C_6$)alkyl, halo($C_1$–$C_6$)alkyl, nitro($C_1$–$C_6$)alkyl, trifluoromethyl, trifluoromethyl($C_1$–$C_6$)alkyl, ($C_1$–$C_6$)acylamino, ($C_1$–$C_6$)acylamino($C_1$–$C_6$)alkyl, ($C_1$–$C_6$)alkoxy($C_1$–$C_6$)acylamino, amino($C_1$–$C_6$)acyl, amino($C_1$–$C_6$)acyl($C_1$–$C_6$)alkyl, ($C_1$–$C_6$)alkylamino($C_1$–$C_6$)acyl, (($C_1$–$C_6$)alkyl)$_2$amino($C_1$–$C_6$)acyl, $R^{15}R^{16}$N—CO—O—, $R^{15}R^{16}$N—CO—($C_1$–$C_6$)alkyl, ($C_1$–$C_6$)alkyl-S(O)$_m$, $R^{15}R^{16}$NS(O)$_m$, $R^{15}R^{16}$NS(O)$_m$($C_1$–$C_6$)alkyl, $R^{15}$S(O)$_m$$R^{16}$N, $R^{15}$S(O)$_m$$R^{16}$N($C_1$–$C_6$)alkyl, and a group of the formula II

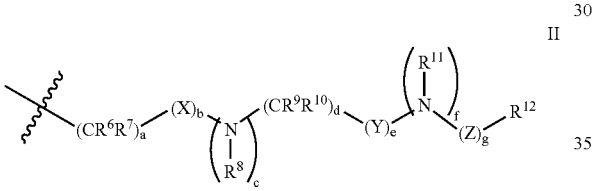

wherein:
m is 0, 1 or 2;
$R^{15}$ and $R^{16}$ are each independently selected from hydrogen or ($C_1$–$C_6$)alkyl;
a is 0, 1, 2, 3 or 4;
b, c, e, f and g are each independently 0 or 1;
d is 0, 1, 2, or 3;
X is S(O)$_n$ wherein n is 0, 1 or 2; oxygen, carbonyl or C(=N-cyano)-;
Y is S(O)$_n$ wherein n is 0, 1 or 2; or carbonyl; and
Z is carbonyl, C(O)O—, C(O)NR— wherein R is hydrogen or ($C_1$–$C_6$)alkyl; or Z is S(O)$_n$ wherein n is 0, 1 or 2;
$R^6$, $R^7$, $R^8$, $R^9$, $R^{10}$ and $R^{11}$ are each independently selected from the group consisting of hydrogen or ($C_1$–$C_6$)alkyl optionally substituted by deuterium, hydroxy, amino, trifluoromethyl, ($C_1$–$C_6$)acyloxy, ($C_1$–$C_6$)acylamino, ($C_1$–$C_6$)alkylamino, (($C_1$–$C_6$)$_2$amino, cyano, cyano($C_1$–$C_6$)alkyl, trifluoromethyl($C_1$–$C_6$)alkyl, nitro, nitro($C_1$–$C_6$)alkyl or ($C_1$–$C_6$)acylamino;
$R^{12}$ is ($C_6$–$C_{10}$)aryl, ($C_2$–$C_9$)heteroaryl, tetrazolyl, or ($C_2$–$C_9$) heterocycloalkyl, wherein the aryl, heteroaryl, tetrazolyl, and heterocycloalkyl groups are optionally substituted by one to four groups consisting of hydrogen, deuterium, amino, halo, oxo, hydroxy, nitro, carboxy, ($C_2$–$C_6$)alkenyl, ($C_2$–$C_6$)alkynyl, trifluoromethyl, trifluoromethoxy, ($C_1$–$C_6$)alkyl, ($C_1$–$C_6$)alkoxy, ($C_3$–$C_{10}$)cycloalkyl, ($C_1$–$C_6$)alkyl-CO—NH—, ($C_1$–$C_6$)alkoxy-CO—NH—, ($C_1$–$C_6$)alkyl -CO—NH—($C_1$–$C_6$)alkyl, ($C_1$–$C_6$)alkoxy-CO—NH—($C_1$–$C_6$)alkyl, ($C_1$–$C_6$)alkoxy-CO—NH-($C_1$–$C_6$)alkoxy, carboxy, carboxy($C_1$–$C_6$)alkyl, carboxy($C_1$–$C_6$)alkoxy, benzyloxycarbonyl($C_1$–$C_6$)alkoxy, ($C_1$–$C_6$) alkoxycarbonyl($C_1$–$C_6$)alkoxy, ($C_6$–$C_{10}$)aryl, amino, amino($C_1$–$C_6$)alkyl, ($C_1$–$C_6$)alkoxycarbonylamino, ($C_6$–$C_{10}$)aryl($C_1$–$C_6$)alkoxycarbonylamino, ($C_1$–$C_6$)alkylamino, (($C_1$–$C_6$)alkyl)$_2$amino, ($C_1$–$C_6$)alkylamino($C_1$–$C_6$)alkyl, (($C_1$–$C_6$)alkyl)$_2$amino($C_1$–$C_6$)alkyl, hydroxy, ($C_1$–$C_6$)alkoxy, carboxy, carboxy($C_1$–$C_6$)alkyl, ($C_1$–$C_6$)alkoxycarbonyl, ($C_1$–$C_6$)alkoxycarbonyl($C_1$–$C_6$)alkyl, ($C_1$–$C_6$)alkoxy-CO—NH—, ($C_1$–$C_6$)alkyl-CO—NH—, cyano, ($C_5$–$C_9$)heterocycloalkyl, amino-CO—NH—, ($C_1$–$C_6$)alkylamino-CO—NH—, (($C_1$–$C_6$)alkyl)$_2$amino-CO—NH—, ($C_6$–$C_{10}$)arylamino-CO—NH—, ($C_5$–$C_9$)heteroarylamino-CO—NH—, ($C_1$–$C_6$)alkylamino-CO—NH—($C_1$–$C_6$)alkyl, (($C_1$–$C_6$)alkyl)$_2$amino-CO—NH—($C_1$–$C_6$alkyl, ($C_6$–$C_{10}$)arylamino-CO—NH—($C_1$–$C_6$)alkyl, ($C_5$–$C_9$)heteroarylamino-CO—NH—($C_1$–$C_6$), cyano($C_1$–$C_6$)alkyl, carboxy($C_1$–$C_6$)alkyl($C_1$–$C_6$)alkoxy, carboxy($C_1$–$C_6$)alkyl, sulfonylamino, aminosulfonyl, sulfonylamino($C_1$–$C_6$)alkyl, sulfonylaminocarboxy($C_1$–$C_6$)alkyl, ($C_1$–$C_6$)alkylsulfonyl, ($C_1$–$C_6$)alkylsulfonylamino, ($C_1$–$C_6$)alkylsulfonylamino($C_1$–$C_6$)alkyl, ($C_6$–$C_{10}$)arylsulfonyl, ($C_6$–$C_{10}$)arylsulfonylamino, ($C_6$–$C_{10}$)arylsulfonylamino($C_1$–$C_6$)alkyl, ($C_1$–$C_6$)alkylsulfonylamino, $C_1$–$C_6$)alkylsulfonylamino($C_1$–$C_6$)alkyl, ($C_3$–$C_{10}$)cycloalkyl, ($C_3$–$C_{10}$)cycloalkoxy, ($C_1$–$C_6$)alkylamino, (($C_1$–$C_6$)alkyl)$_2$amino, ($C_6$–$C_{10}$)arylamino, ($C_1$–$C_6$)alkylthio, ($C_6$–$C_{10}$)arylthio, ($C_1$–$C_6$)alkylsulfinyl, ($C_6$–$C_{10}$)arylsulfinyl, ($C_1$–$C_6$)alkylsulfonyl, ($C_6$–$C_{10}$)arylsulfonyl, ($C_1$–$C_6$)acyl, ($C_1$–$C_6$)alkoxy-CO—NH—, ($C_1$–$C_6$)alkylamino-CO—, ($C_5$–$C_9$)heteroaryl, ($C_2$–$C_9$)heterocycloalkyl or ($C_6$–$C_{10}$)aryl wherein the heteroaryl, tetrazolyl, herocycloalkyl and aryl groups which are optionally substituted on $R^{12}$ may be further substituted by one to three groups consisting of halo, ($C_1$–$C_6$)alkyl, ($C_1$–$C_6$)alkyl-CO—NH—, $C_1$–$C_6$)alkoxy-CO—NH—, ($C_1$–$C_6$)alkyl-CO—NH—($C_1$–$C_6$)alkyl, ($C_1$–$C_6$)alkoxy-CO—NH—($C_1$–$C_6$)alkyl, ($C_1$–$C_6$)alkoxy-CO—NH—($C_1$–$C_6$)alkoxy, carboxy, carboxy($C_1$–$C_6$)alkyl, carboxy($C_1$–$C_6$)alkoxy, benzyloxycarbonyl ($C_1$–$C_6$)alkoxy, ($C_1$–$C_6$)alkoxycarbonyl($C_1$–$C_6$)alkoxy, ($C_6$–$C_{10}$)aryl, amino, amino($C_1$–$C_6$)alkyl, ($C_1$–$C_6$)alkoxycarbonylamino, ($C_6$–C 10)aryl($C_1$–$C_6$)alkoxycarbonylamino, ($C_1$–$C_6$)alkylamino, (($C_1$–$C_6$)alkyl )$_2$amino, ($C_1$–$C_6$)alkylamino($C_1$–$C_6$) alkyl, (($C_1$–$C_6$)alkyl)$_2$amino($C_1$–$C_6$)alkyl, hydroxy, ($C_1$–$C_6$)alkoxy, carboxy, carboxy($C_1$–$C_6$)alkyl, ($C_1$–$C_6$)alkoxycarbonyl, ($C_1$–$C_6$)alkoxycarbonyl($C_1$–$C_6$)alkyl, ($C_1$–$C_6$)alkoxy-CO—NH—, ($C_1$–$C_6$)alkyl-CO—NH—, cyano, ($C_5$–$C_9$)heterocycloaikyl, amino-CO—NH—, ($C_1$–$C_6$)alkylamino-CO—NH—, (($C_1$–$C_6$)$_2$amino-CO—NH—, ($C_1$–$C_{10}$)arylamino-CO—NH—, ($C_5$–$C_9$)heteroarylamino-CO—NH—, ($C_1$–$C_6$)alkylamino-CO—NH—($C_1$–$C_6$)alkyl, (($C_1$–$C_6$)alkyl)$_2$amino-CO—NH—($C_1$–$C_6$)alkyl, ($C_6$–$C_{10}$)arylamino-CO —NH—($C_1$–$C_6$)alkyl, ($C_5$–$C_9$)heteroarylamino-CO—NH—($C_1$–$C_6$)alkyl, ($C_1$–$C_6$)alkylsulfonyl, ($C_1$–$C_6$) alkylsulfonylamino, ($C_1$–$C_6$)alkylsulfonylamino($C_1$–$C_6$)alkyl, ($C_6$–$C_{10}$)arylsulfonyl, ($C_6$–$C_{10}$)arylsulfonylamino, ($C_6$–$C_{10}$)arylsulfonylamino ($C_1$–$C_6$)alkyl, ($C_1$–$C_6$)alkylsulfonylamino, ($C_1$–$C_6$)

alkylsulfonylamino($C_1$–$C_6$)alkyl, ($C_5$–$C_9$)heteroaryl and ($C_2$–$C_9$)heterocycloalkyl;

$R^2$ and $R^3$ are each independently selected from the group consisting of hydrogen, deuterium, amino, halo, hydroxy, nitro, carboxy, ($C_2$–$C_6$)alkenyl, ($C_2$–$C_6$)alkynyl, trifluoromethyl, trifluoromethoxy, ($C_1$–$C_6$)alkyl, ($C_1$–$C_6$)alkoxy, ($C_3$–$C_{10}$)cycloalkyl wherein the alkyl, alkoxy or cycloalkyl groups are optionally substituted by one to three groups selected from halo, hydroxy, carboxy, amino ($C_1$–$C_6$)alkylthio, ($C_1$–$C_6$)alkylamino, (($C_1$–$C_6$)alkyl)$_2$amino, ($C_5$–$C_9$)heteroaryl, ($C_2$–$C_9$)heterocycloalkyl, ($C_3$–$C_9$)cycloalkyl or ($C_6$–$C_{10}$)aryl; or $R^2$ and $R^3$ are each independently ($C_3$–$C_{10}$)cycloalkyl, ($C_3$–$C_{10}$)cycloalkoxy, ($C_1$–$C_6$)alkylamino, (($C_1$–$C_6$)alkyl)$_2$amino, ($C_6$–$C_{10}$)arylamino, ($C_1$–$C_6$)alkylthio, ($C_6$–$C_{10}$)arylthio, ($C_1$–$C_6$)alkylsulfinyl, ($C_6$–$C_{10}$)arylsulfinyl, ($C_1$–$C_6$)alkylsulfonyl, ($C_6$–$C_{10}$)arylsulfonyl, ($C_1$–$C_6$)acyl, ($C_1$–$C_6$)alkoxy-CO—NH—, ($C_1$–$C_6$)alkylamino-CO—, ($C_5$–$C_9$)heteroaryl, ($C_2$–$C_9$)heterocycloalkyl or ($C_6$–$C_{10}$)aryl wherein the heteroaryl, heterocycloalkyl and aryl groups are optionally substituted by one to three halo, ($C_1$–$C_6$)alkyl, ($C_1$–$C_6$)alkyl-CO—NH—, ($C_1$–$C_6$)alkoxy-CO—NH—, ($C_1$–$C_6$)alkyl-CO—NH—($C_1$–$C_6$)alkyl, ($C_1$–$C_6$)alkoxy-CO—NH—($C_1$–$C_6$)alkyl, ($C_1$–$C_6$)alkoxy-CO—NH—($C_1$–$C_6$)alkoxy, carboxy, carboxy($C_1$–$C_6$)alkyl, carboxy($C_1$–$C_6$)alkoxy, benzyloxycarbonyl($C_1$–$C_6$)alkoxy, ($C_1$–$C_6$)alkoxycarbonyl($C_1$–$C_6$)alkoxy, ($C_6$–$C_{10}$)aryl, amino, amino($C_1$–$C_6$)alkyl, ($C_1$–$C_6$)alkoxycarbonylamino, ($C_6$–$C_{10}$)aryl ($C_1$–$C_6$)alkoxycarbonylamino, ($C_1$–$C_6$)alkylamino, (($C_1$–$C_6$)alkyl)$_2$amino, ($C_1$–$C_6$)alkylamino($C_1$–$C_6$)alkyl, (($C_1$–$C_6$)alkyl)$_2$amino($C_1$–$C_6$)alkyl, hydroxy, ($C_1$–$C_6$)alkoxy, carboxy, carboxy($C_1$–$C_6$)alkyl, ($C_1$–$C_6$)alkoxycarbonyl, ($C_1$–$C_6$)alkoxycarbonyl($C_1$–$C_6$)alkyl, ($C_1$–$C_6$)alkoxy-CO—NH—, ($C_1$–$C_6$)alkyl-CO—NH—, cyano, ($C_5$–$C_9$)heterocycloalkyl, amino-CO—NH—, ($C_1$–$C_6$)alkylamino-CO—NH—, (($C_1$–$C_6$)alkyl)$_2$amino-C—NH—, ($C_6$–$C_{10}$)arylamino-CO—NH—, ($C_5$–$C_9$)heteroarylamino-CO—NH—, ($C_1$–$C_6$)alkylamino-CO—NH—($C_1$–$C_6$)alkyl, (($C_1$–$C_6$)alkyl)$_2$amino-CO—NH—($C_1$–$C_6$)alkyl, ($C_6$–$C_{10}$)arylamino-CO—NH—($C_1$–$C_6$)alkyl, ($C_5$–$C_9$)heteroarylamino-CO—NH—($C_1$–$C_6$)alkyl, ($C_1$–$C_6$)alkylsulfonyl, ($C_1$–$C_6$)alkylsulfonylamino. ($C_1$–$C_6$)alkylsulfonylamino($C_1$–$C_6$)al kyl, ($C_6$–$C_{10}$)arylsulfonyl, ($C_6$–$C_{10}$)arylsulfonylamino, ($C_6$–$C_{10}$)arylsulfonylamino($C_1$–$C_6$)alkyl, ($C_1$–$C_6$)alkylsulfonylamino, ($C_1$–$C_6$)alkylsulfonylamino($C_1$–$C_6$)alkyl, ($C_5$–$C_9$)heteroaryl or ($C_2$–$C_9$)heterocycloalkyl;

with the proviso that $R^5$ must be substituted by the group of formula II;

alone or in combination with one or more additional agents which modulate a mammalian immune system or with anti-inflammatory agents.

23. The method according to claim 22, wherein $R^5$ is ($C_2$–$C_9$)heterocycloalkyl optionally substituted by one to three groups selected from deuterium, hydroxy, ($C_1$–$C_6$)alkyl, halo, ($C_1$–$C_6$)alkoxy and a group of formula II.

24. The method according to claim 22, wherein a is 0; b is 1; X is carbonyl; e is 0; d is 0; e is 0; f is 0; and g is 0.

25. The method according to claim 22, wherein a is 0; b is 1; X is carbonyl; c is 0; d is 1; e is 0; f is 0, and g is 0.

26. The method according to claim 22, wherein a is 0; b is 1; X is carbonyl; c is 1; d is 0; e is 0; f is 0; and g is 0.

27. The method according to claim 22, wherein a is 0; b is 1; X is —C(=N=cyano); c is 1; d is 0; e is 0; f is 0; and g is 0.

28. The method according to claim 22, wherein a is 0; b is 0; c is 0; d is 0; e is 0; f is 0; g is 1; and Z is —C(O)—O—.

29. The method according to claim 22, wherein a is 0; b is 1; X is S(O)$_n$; n is 2; c is 0; d is 0; e is 0; f is 0; and g is 0.

30. The method according to claim 22, wherein a is 0; b is 1; X is S(O)$_n$; n is 2; c is 0; d is 2; e is 0; f is 1; g is 1; and Z is carbonyl.

31. The method according to claim 22, wherein a is 0; b is 1; X is S(O)$_n$; n is 2; c is 0; d is 2; e is 0; f is 1; and g is 0.

32. The method according to claim 22, wherein a is 0; b is 1; X is carbonyl; c is 1; d is 0; e is 1; Y is S(O)$_n$; n is 2; f is 0; and g is 0.

33. The method according to claim 22, wherein a is 0; b is 1; X is S(O)$_n$; n is 2; c is 1; d is 0; e is 0; f is 0; and g is 0.

34. The method according to claim 22, wherein a is 1; b is 1; X is carbonyl; c is 1; d is 0; e is 0; f is 0; and g is 0.

35. The method according to claim 22, wherein a is 0; b is 1; X is S(O)$_n$; c is 0; d is 1; e is 1; Y is S(O)$_n$; n is 2; f is 0; and g is 0.

36. The method according to claim 22, wherein a is 0; b is 1; X is S(O)$_n$; c is 0; d is 1; e is 1; Y is S(O)$_n$; n is 2; f is 1; and g is 0.

37. The method according to claim 22, wherein a is 0; b is 1; X is oxygen; c is 0; d is 1; e is 1; Y is S(O)$_n$; n is 2; f is 1; and g is 0.

38. The method according to claim 22, wherein a is 0; b is 1; X is oxygen; c is 0; d is 1; e is 1; Y is S(O)$_n$; n is 2; f is 0; and g is 0.

39. The method according to claim 22, wherein a is 0; b is 1; X is carbonyl; c is 1; d is 1; e is 1; Y is S(O)$_n$; f is 0; and g is 0.

40. The method according to claim 22, wherein a is 0; b is 1; X is carbonyl; c is 1; d is 1; e is 1; Y is S(O)$_n$; n is 2; f is 1; and g is 0.

41. The method according to claim 22, wherein $R^{12}$ is ($C_6$–$C_{10}$)aryl or ($C_2$–$C_9$)heteroaryl or tetrazolyl wherein the aryl or heteroaryl or tetrazolyl group is optionally substituted by one to four groups consisting of hydrogen, halo, hydroxy, carboxy, trifluoromethyl, $C_1$–$C_6$)alkyl, ($C_1$–$C_6$)alkoxy, $C_1$–$C_6$)alkyl-CO—NH—, amino, amino($C_1$–$C_6$)alkyl, ($C_1$–$C_6$)alkylamino, (($C_1$–$C_6$)alkyl)$_2$amino, cyano, amino-CO—NH—, ($C_1$–$C_6$)alkylamino-CO—NH—, (($C_1$–$C_6$)alkyl)$_2$amino-CO—NH—, ($C_5$–$C_9$)heteroarylamino-CO—NH—, ($C_1$–$C_6$)alkylsulfonyl, $C_1$–$C_6$)alkylsulfonylamino, ($C_6$–$C_{10}$)arylsulfonylamino, ($C_1$–$C_6$)alkylsulfonylamino, and ($C_1$–$C_6$)alkoxy-CO—NH—.

42. A method for treating organ transplant rejection, comprising administering to a mammal an effective amount of a compound selected from the group consisting of 4-{4-Methyl-3-[methyl-(7H-pyrrolo[2,3-d]pyrimidin-4-yl)-amino]-piperidin-1-ylmethyl}-benzenesulfonamide;

4-Methyl-3-[methyl-(7H-pyrrolo[2,3-d]pyrimidin-4-yl)-amino]-piperidine-1-carboxylic acid (4-sulfamoyl-phenyl)-amide;

4-Methyl-3-[methyl-(7H-pyrrolo[2,3-d]pyrimidin-4yl)-amino]-piperidine-1-carboxylic acid (4-nitro-phenyl)-amide;

1-{4-Methyl-3-[methyl-(7H-pyrrolo[2,3-d]pyrimidin-4-yl)-aminol]-piperidin-1-yl}-2-tetrazol-1-yl-ethanone;

4-Methy1-3-methyl-(7H-pyrrolo[2,3-d[pyrimidin-4-yl)-amino]-piperidine-1-carboxylic acid (4-methylsulfamoyl-phenyl)-amide;

(3-Hydroxy-pyrrolidin-1-yl)-{4-methyl-3-[methyl-(7H-pyrrololo[2,3-d]pyrimidin-4-yl)-amino]-piperidin-1-yl}-methanone;

[2-{4-Methyl-3-[methyl -(7H-pyrrolo[2,3-d]pyrimidin-4-yl)-amino]-piperidine-1-carbonyl}-amino)-thiazol-4-yl]-acetic acid;

5-(2-{4-Methyl-3-[methyl-(7H-pyrrolo[2,3-d]pyrimidin-4-yl)-amino]-piperidin-1-yl}-2-oxo-ethyl)-thiazolidine-2,4-dione;

{4-Methyl-3-methyl-(7H-pyrrolo[2,3-d]pyrimidin-4-yl)-amino]-piperidin-1-yl}-thiazolidin-3-yl-methanone;

Methyl-[4-methyl-1-(5-nitro-thiazol-2-yl)-piperidin-3-yl]-(7H-pyrrolo[2,3-d]pyrimidin-4-yl)-amine;

[2-{4-Methyl-3-[methyl-(7H-pyrrolo[2,3-d]pyrimidin-4-yl)-amino]-piperidine-1-carbonyl}-amino)-thiazol-4-y]-acetic acid ethyl ester;

4-Methyl-3-[methyl-(7H-pyrrolo[2,3-d]pyrimidin-4-yl)-amino]-piperidine-1-carboxylic acid (4-methanesulfonyl-phenyl)-amide;

4-Methyl-3-[methyl-(7H-pyrrolo[2,3-d]pyrimidin-4-yl)-amino]-piperidine-1-carboxylic acid thiazol-2-ylamide;

4-Methyl-3-[methyl-(7H-pyrrolo[2,3-d]pyrimidin-4-yl)-amino]-piperidine-1-carboxylic acid (4-cyano-phenyl)-amide;

{4-Methyl-3-[methyl-(7H-pyrrolo[2,3-d]pyrimidin-4-yl)-amino]-piperidin-1yl)}-pyrrolidin-1-yl-methanone;

Furan-2-carboxylic acid (2-{4-methyl-3-[methyl-(7H-pyrrolo[2,3-d]pyrimidin-4-yl)-amino]-piperidine-1-sulfonyl}-ethyl)-amide;

{4-Methyl-3-[methyl-(7H-pyrrolo[2,3-d]pyrimidin-4-yl)-amino]-piperidin-1-yl}(tetrahydro-furan3-yl)-methanone;

4-Methyl-3-[methyl-(7H-pyrrolo[2,3-d]pyrimidin-4-yl)-amino]-piperidine-1-carboxylic acid isoxazol-3-ylamide;

4-Methyl-3-[methyl-(7H-pyrrolo[2,3-d]pyrimidin-4-yl)-amino]-piperidine-1-carboxylic acid (6-cyano-pyridin-3-yl)-amide;

4-Methyl-3-[methyl-(7H-pyrrolo[2,3-d]pyrimidin-4-yl)-amino]-piperidine-1-carboxylic acid (4-methyl-thiazol-2-yl)-amide;

2-Cyclopropyl-1-{4-methyl-3[methyl-(7H-pyrrolo[2,3-d]pyrimidin-4-yl)-amino]-piperidin-1-yl}-ethanone;

Cyclopentyl-{4-methyl-3-[methyl-(7H-pyrrolo[2,3-d]pyrimidin-4-yl)-amino]-piperidin-1-yl}-Methanone;

4-Methyl-3-[methyl-(7H-pyrrolo[2,3-d]pyrimidin-4-yl)-amino]-piperidine-1-carboxylic acid (3-methyl-isoxazol-4-yl)-amide;

[4-({4-Methyl-3-[methyl-(7H-pyrrolo[2,3-d]pyrimidin-4-yl)-amino]-piperidine-1-carbonyl}-amino)-phenyl]4-acetic acid;

[1-(5-Amino-thiazol-2-yl)-4-methyl-piperidin-3-yl]-methyl-(7H-pyrrolo[2,3-d]pyrimidin-4-yl)-amine;

4-Methyl-3-[methyl-(7H-pyrrolo[2,3-d]pyrimidin-4-yl)-amino]-piperidine-1-carboxylic acid (3-methyl-isothiazol-5-yl)-amide;

3-{4-Methyl-3-[methyl-(7H-pyrrolo[2,3-d]pyrimidin-4-yl)-amino]-piperidine-1-carbonyl}-cyclopentanone; and 4-Methyl-3-[methyl-(7H-pyrrolo[2,3-d]pyrimidin-4-yl)-amino]-piperidine-1-carboxylic acid benzyl-methyl-amide;

or a pharmaceutically acceptable salt thereof.

43. The method according to claim 1, wherein said one or more additional agents is selected from the group consisting of cyclosporin A, rapamycin, tacrolimus, leflunomide, deoxyspergualin, mycophenolate, azathioprine, daclizumab, muromonab-CD3, antithymocyre globulin, aspirin, acetaminophen, ibuprofen, naproxen, piroxicam, prednisolone and dexamethasone.

44. The method according to claim 22, wherein said one or more additional agents is selected from the group consisting of cyciosporin A, rapamycin, tacrolimus, leflunomide, deoxyspergualin, mycophenol ate, azathioprine, daclizumab, muromonab-CD3, antithymocyte globulin, aspirin, acetaminophen, ibuprofen, naproxen, piroxicam, prednisolone and dexamethasone.

45. The method according to claim 21 further comprising administering one or more additional agents which modulate a mammalian immune system or with antiinflamatory agents.

46. The method according to claim 45, wherein said one or more additional agents is selected from the group consisting of cyclosporin A, rapamycin, tacrolimus, leflunomide, deoxyspergualin, mycophenolate, azathioprine, daclizumab, muromonab-CD3, antithymocyte globulin, aspirin, acetaminophen, ibuprofen, naproxen, piroxicam, prednisolone and dexamethasone.

47. The method according to claim 42 further comprising administering one or more additional agents which modulate a mammalian immune system or with antiinflamatory agents.

48. The method according to claim 47, wherein said one or more additional agents is selected from the group consisting of cyclosporin A, rapamycin, tacrolimus, leflunomide, deoxyspergualin, mycophenolate, azathioprine, daclizumab, muromonab-CD3, antithymocyte globulin, aspirin, acetaminophen, ibuprofen, naproxen, piroxicam, prednisolone and dexamethasone.

* * * * *